(12) United States Patent
Lee et al.

(10) Patent No.: US 9,879,059 B2
(45) Date of Patent: Jan. 30, 2018

(54) TAILORING MULTIVALENT INTERACTIONS OF BIOPOLYMERS WITH A POLYPROLINE SCAFFOLD

(71) Applicant: Agency for Science, Technology and Research, Singapore (SG)

(72) Inventors: Song-Gil Lee, Singapore (SG); Su Seong Lee, Singapore (SG); Jaehong Lim, Singapore (SG); Jian Liang Cheong, Singapore (SG); Teck Chuan Lim, Singapore (SG); Shuting Cai, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 14/787,138

(22) PCT Filed: Apr. 28, 2014

(86) PCT No.: PCT/SG2014/000191
§ 371 (c)(1),
(2) Date: Oct. 26, 2015

(87) PCT Pub. No.: WO2014/175838
PCT Pub. Date: Oct. 30, 2014

(65) Prior Publication Data
US 2016/0075746 A1 Mar. 17, 2016

(30) Foreign Application Priority Data

Apr. 26, 2013 (SG) .............................. 201303240-4

(51) Int. Cl.
| | | |
|---|---|---|
| A61K 31/16 | (2006.01) | |
| C07K 14/435 | (2006.01) | |
| C07K 9/00 | (2006.01) | |
| C07K 14/00 | (2006.01) | |
| A61K 38/00 | (2006.01) | |

(52) U.S. Cl.
CPC ............ *C07K 14/435* (2013.01); *C07K 9/003* (2013.01); *C07K 14/001* (2013.01); *A61K 38/00* (2013.01)

(58) Field of Classification Search
CPC .... A61K 38/00; C07K 14/001; C07K 14/435; C07K 9/003
See application file for complete search history.

(56) References Cited

U.S. PATENT DOCUMENTS

| | | | | |
|---|---|---|---|---|
| 6,790,942 B1* | 9/2004 | Schiavon | ......... | A61K 47/48169 424/198.1 |
| 8,383,125 B2* | 2/2013 | Cocks | ................. | C07K 14/47 424/134.1 |
| 2009/0312248 A1* | 12/2009 | Cocks | ................. | C07K 14/47 514/2.9 |
| 2013/0281646 A1* | 10/2013 | Korzekwa | ............ | A61K 47/32 526/264 |

FOREIGN PATENT DOCUMENTS

WO WO-2014/175838 10/2014

OTHER PUBLICATIONS

Parrill. Amino Acid Structures and Amino Acid PKa Values. 1997. accessed online at http://www.cem.msu.edu/~cem252/sp97/ch24/ch24aa.html on Mar. 8, 2017. 2 pages.*
"International Application No. PCT/SG2014/000191, International Preliminary Report on Patentability dated Aug. 21, 2015", (Aug. 21, 2015), 30 pgs.
"International Application No. PCT/SG2014/000191, International Search Report and Written Opinion dated Aug. 15, 2014", (Aug. 15, 2014), 14 pgs.
Belot, Frederic, et al., "Syntheses of chondroitin 4- and 6-sulfate pentasaccharide derivatives having a methyl b-D-glucopyranosiduronic acid at the reducing end", Carbohydrate Research 326 (2000) 88-97, (Jan. 13, 2000), 88-97.
Cairo, Christopher W., et al., "Control of Multivalent Interactions by Binding Epitope Density", J. Am. Chem. Soc. 9 Vol. 124, No. 8, 2002, (Feb. 2, 2002), 1615-1619.
Cowman, Mary K., et al., "Preparation and Circular Dichroism Analysis of Sodium Hyaluronate Oligosaccharides and Chondroitin", Biochemistry (1981), 20, 1379-1385, (1981), 1379-1385.
Crane, Erika A., et al., "Enantioselective Synthesis of (ÿ)-Exiguolide by Iterative Stereoselective Dioxinone-Directed Prins Cyclizations", Angew. Chem. Int. Ed. 2011, 50, 9112-9115; DOI: 10.1002/anie.201102790, (2011), 9112-9115.
Fillon, Yannick A., et al., "Cell Penetrating Agents Based on a Polyproline Helix Scaffold", J. Am. Chem. Soc. 2005, 127, 11798-11803, (Jul. 30, 2005), 11798-11803.
Gestwicki, Jason E., et al., "Influencing Receptor-Ligand Binding Mechanisms with Multivalent Ligand Architecture", J. Am. Chem. Soc. 2002, 124, 14922-14933, (Nov. 22, 2002), 14922-14933.
Jay, Julie I., et al., "Multivalent Benzoboroxole Functionalized Polymers as gp120 Glycan Targeted Microbicide Entry Inhibitors", Molecular Pharmaceutics Vol. 7, No. 1, 116-129, (Nov. 23, 2009), 116-129.
Karlsson, Robert, et al., "Experimental design for kinetic analysis of protein—protein interactions with surface plasmon resonance biosensors", Journal of Immunological Methods 200 (1997) 121-133, (Oct. 1, 1996), 121-133.
Kizhakkedathu, Jayachandran N., et al., "High Molecular Weight Polyglycerol-Based Multivalent Mannose Conjugates", Biomacromolecules 2010, 11, 2567-2575, (Aug. 10, 2010), 2567-2575.
Kumin, Michael, et al., "Azidoproline Containing Helices: Stabilization of the Polyproline II Structure by a Functionalizable Group", J. Am. Chem. Soc. 2007, 129, 466-467, (Dec. 29, 2006), 466-467.
Lipschultz, Claudia A., et al., "Experimental Design for Analysis of Complex Kinetics Using Surface Plasmon Resonance", Methods 20, 310-318 (2000); doi:10.1006/meth.1999.0924, (2000), 310-318.
Lucas, H., et al., "Syntheses of Heparin-Like Pentamers Containing "Opened" Uronic Acid Moities", Tetrahedron, vol. 46, No. 24, pp. 8207-8228, 1990, (Sep. 10, 1990), 8207-8228.

(Continued)

*Primary Examiner* — Marcela M Cordero Garcia
(74) *Attorney, Agent, or Firm* — Schwegman Lundberg & Woessner, P.A.

(57) ABSTRACT

A glycopeptide, comprising a polyproline backbone and one or more carbohydrate molecules.

20 Claims, 37 Drawing Sheets

(56) References Cited

OTHER PUBLICATIONS

Nagel, Lilly, et al., "Influence of Sequential Modifications and Carbohydrate Variations in Synthetic AFGP Analogues on Conformation and Antifreeze Activity", Chem. Eur. J. 2012, 18, 12783-12793, (Aug. 28, 2012), 12783-12793.
Owens, Neil W., et al., "Contiguous O-Galactosylation of 4(R)-Hydroxy-L-proline Residues Forms Very Stable Polyproline II Helices", J. Am. Chem. Soc. 2010, 132, 5036-5042, (Mar. 24, 2010), 5036-5042.
Pathigoolla, Atchutarao, et al., "Topochemical Click Reaction: Spontaneous Self-Stitching of a Monosaccharide to Linear Oligomers through Lattice-Controlled Azide-Alkyne Cycloaddition", Angew. Chem. Int. Ed. 2012, 51, 4362-4366, (2012), 4362-4366.
Polizzotti, Brian D., et al., "Effects of Saccharide Spacing and Chain Extension on Toxin Inhibition by Glycopolypeptides of Well-Defined Architecture", Macromolecules 2007, 40, 7103-7110, (Jul. 16, 2007), 7103-7110.
Richards, Sarah-Jane, et al., "Probing Bacterial-Toxin Inhibition with Synthetic Glycopolymers Prepared by Tandem Post-Polymerization Modification: Role of Linker Length and Carbohydrate Density", Angew. Chem. Int. Ed. 2012, 51, 7812-7816, (2012), 7812-7816.
Rogers, Claude J., et al., "Elucidating glycosaminoglycan-protein-protein interactions using carbohydrate microarray and computational approaches", PNAS, vol. 108, No. 24, 9747-9752, Jun. 14, 2011, (Jun. 14, 2011), 9747-9752.
Tsvetkov, Yury E., et al., "Synthesis and Molecular Recognition Studies of the HNK-1 Trisaccharide and Related Oligosaccharides. The Specificity of Monoclonal Anti-HNK-1 Antibodies as Assessed by Surface Plasmon Resonance and STD NMR", J. Am. Chem. Soc. 2012, 134, 426-435; dx.doi.org/10.1021/ja2083015, (Nov. 16, 2011), 426-435.
Zhou, Qing-Han, et al., "Synthesis and Hierarchical Self-Assembly of Rod-Rod Block Copolymers via Click Chemistry between Mesogen-Jacketed Liquid Crystalline Polymers and Helical Polypeptides", Macromolecules 2010, 43, 5637-5646, (Jun. 1, 2010), 5637-5646.
"Chinese Application No. 201480035505.X, First Office Action dated Dec. 15, 2016", (Dec. 15, 2016), 16 pgs.
Corcilius, Leo, et al., "Synthesis of peptides and glycopeptides with polyproline II helical topology as potential antifreeze molecules", Bioorganic & Medicinal Chemistry, vol. 21, Issue 12, Jun. 15, 2013, pp. 3569-3581, (Feb. 21, 2013), 3569-3581.
Erdmann, Roman S., et al., "Functionalizable Collagen Model Peptides", J. Am. Chem. Soc., 2010, 132 (40), pp. 13957-13959, (Sep. 17, 2010), 13957-13959.
Naziga, Emmanuel B., et al., "Solvent Interactions Stabilize the Polyproline II Conformation of Glycosylated Oligoprolines", J. Phys. Chem. B, 2013, 117 (9), pp. 2671-2681, (Jan. 30, 2013), 2671-2681.

"European Application Serial No. 14788196.5, Further Submissions filed Aug. 2, 2017", 19 pgs.
"European Application Serial No. 14788196.5, Office Action dated Nov. 22, 2016", 1 pg.
"European Application Serial No. 14788196.5, Response filed May 19, 2017 in reply to Office Action dated Nov. 22, 2016", 21 pgs.
"Tailoring Multivalent Interactions of Glycosaminoglycan Mimetics with a Polyproline Scaffold", (2017), 4 pgs.
Huang, Eric J., et al., "Trk Receptors: Roles in Neuronal Signal Transduction", Annu. Rev. Biochem., 72, (2003), 609-642.
Kroll, Carsten, et al., "Hybrid Bombesin Analogues: Combining an Agonist and an Antagonist in Defined Distances for Optimized Tumor Targeting", Journal of the American Chemical Society135, (2013), 16793-16796.
Liu, Pei, et al., "Tailored chondroitin sulfate glycomimetics via a tunable multivalent scaffold for potentiating NGF/TrkA-induced neurogenesis", Chem. Sci., 6, (2015), 450-456.
Liu, Pei, et al., "Tailored Chondroitin Sulfate Glycomimetics via a Tunable Multivalent Scaffold for Potentiating NGF/TrkA-Induced Neurogensis", Supplementary Information, Chem. Sci., 6, (2015), S1-S39.
Peiró, Sandra, et al., "PC12 Cells Have Caveolae That Contain TrkA", The Journal of Biological Chemistry, 275(48), (2000), 37846-37852.
Rydén, Mikael, et al., "Differential Modulation of Neuron Survival during Development by Nerve Growth Factor Binding to the p74 Neurotrophin Receptor", The Journal of Biological Chemistry, 272(26), (1997), 16322-16328.
Vambutas, Vida, et al., "Nerve Growth Factor Stimulates Tyrosine Phosphorylation and Activation of Src Homology-containing Protein-tyrosine Phosphatas 1 in PC12 Cells", The Journal of Biological Chemistry, 270(42), (1995), 25629-25633.
Wiesmann, Christian, et al., "Crystal structure of nerve growth factor in complex with the ligand-binding domain of the TrkA receptor", d, (1999), 184-187.
Wyman, T. C., et al., "Promoter-Activated Expression of Nerve Growth Factor for Treatment of Neurodegenerative Diseases", Gene Therapy, 6, (1999), 1648-1660.
"European Application Serial No. 14788196.5, Extended European Search Report dated Nov. 3, 2016", 8 pgs.
"Singapore Application Serial No. 11201508803R, Search Report dated Sep. 22, 2016", 3 pgs.
"Singapore Application Serial No. 11201508803R, Written Opinion dated Mar. 20, 2017", 9 pgs.
Bonger, Kimberly M., et al., "Oligoproline helices as structurally defined scaffolds for oligomeric G protein-coupled receptor ligands", Organic & biomolecular chemistry 8.8, (2010), 1881-1884.
Kroll, Carsten, et al., "Hybrid Bombesin Analogues—Combining an Agonist and an Antagonist in Defined Distances for Optimized Tumor Targeting", Supporting Information, Journal of the American Chemical Society, 135(45), (2013), S1-S13.

\* cited by examiner

TAILORING MULTIVALENT INTERACTIONS OF BIOPOLYMERS WITH A POLYPROLINE SCAFFOLD

PRIORITY CLAIM TO RELATED APPLICATIONS

This application is a U.S. national stage application filed under 35 U.S.C. § 371 from International Application Serial No. PCT/SG2014/000191, which was filed 28 Apr. 2014, and published as WO2014/175838 on 30 Oct. 2014, and which claims priority to Singapore Application No. 201303240-4, filed 26 Apr. 2013, which applications and publication are incorporated by reference as if reproduced herein and made a part hereof in their entirety, and the benefit of priority of each of which is claimed herein.

TECHNICAL FIELD

The present invention generally relates to a method of modulating and controlling the binding affinity of a biopolymer to its target binding molecules. The present invention also relates to a biopolymer having improved binding affinity for its target binding molecule, methods for preparing such a biopolymer, and its uses thereof.

BACKGROUND

Carbohydrates are involved in many important biological processes. Natural polysaccharides are often able to perform complex functions via well-controlled multivalent interactions of key functional motifs with corresponding binding proteins. To date, there have been many attempts to design glycomimetics that are capable of recapitulating some of these binding events that take place in nature.

While some structural guidelines to the design of glycomimetics are available, precise control of the polymer backbone conformations of these glycomimetics is still lacking. This has hampered efforts to understand or mimic the binding of these natural polysaccharides to their binding molecules. Studies with α-helical glycopeptides, for example, have revealed that the variation in α-helicities of these glycopeptides stem from relatively low thermodynamic stabilities, pendant group dependencies and complementary interactions with proteins. This makes it particularly difficult to design binding or functional motifs at desired positions on glycomimetics to facilitate binding to their corresponding binding molecules.

There is a need to provide glycomimetics that overcome, or at least ameliorate, one or more of the disadvantages described above.

There is a need to provide glycomimetics that not only maintain key properties of natural polysaccharides, but also adopt a predictable, well-defined and stable conformation that enable binding or functional motifs to be more accurately and optimally positioned on its backbone and therefore, improved control of their multivalent interactions with binding molecules.

SUMMARY

According to a first aspect, there is provided a glycopeptide, comprising a polyproline backbone and one or more carbohydrate molecules. Advantageously, the polyproline backbone provides conformational stability to the glycopeptide, and has 3-fold repeating units of the polyproline type II (PPII) helix that allows for the precise orientation of functional groups at desired sites along a rigid backbone.

The polyproline backbone may comprise (4R)-azidoproline (Azp). Advantageously, incorporation of Azp into polyproline stabilizes its PPII helix conformation via an azido gauche effect, and enables the polyproline to be efficiently functionalized by Cu(I)-catalyzed coupling reaction with alkyne (click reaction) without affecting its PPII conformation.

The carbohydrate molecules may be attached at pre-determined positions along the polyproline backbone. The carbohydrate molecules may be attached at equal distances from each other along the polyproline backbone, or along the same face of the polyproline backbone. Advantageously, such pre-determined positioning of the carbohydrate molecules along the polyproline backbone improves the binding affinity of the glycopeptide to its target molecule(s).

According to a second aspect, there is provided a method of synthesizing a glycopeptide as defined above, comprising attaching one or more carbohydrate molecules to a polyproline backbone.

According to a third aspect, there is provided a glycopeptide as defined above for use in therapy.

According to a fourth aspect, there is provided a method of treating a patient in need of a target-specific therapy, comprising the administration of a glycopeptide as defined above.

According to a fifth aspect, there is provided a target-specific therapeutic agent comprising a glycopeptide as defined above.

According to a sixth aspect, there is provided a glycopeptide as defined above for use as target-specific biopolymers.

According to a seventh aspect, there is provided a glycopeptide as defined above for use in glycosaminoglycans (GAG)-based pharmaceutics.

According to an eighth aspect, there is provided a glycopeptide as defined above for use as diagnostic tools.

According to a ninth aspect, there is provided a method of controlling the binding affinity of a glycopeptide to one or more binding molecules, comprising attaching one or more carbohydrate molecules at pre-determined positions along a polyproline backbone.

According to a tenth aspect, there is provided a polyproline backbone, comprising (4R)-azidoproline (Azp).

DEFINITIONS

The following words and terms used herein shall have the meaning indicated:

The term "glycomimetic" as used herein refers to a molecule that has a structure, and typically biological properties, that are similar to carbohydrates.

The term "glycopeptide" as used herein refers to a peptide that has one or more carbohydrate moieties attached thereto. A glycopeptide is typically a fragment of a glycoprotein, and may be obtained by chemical or enzymatic synthesis, or by chemical or enzymatic cleavage of a glycoprotein. Exemplary glycoproteins include, but are not limited to, collagens, mucins, transferrins, ceruloplasmin, immunoglobulins, histocompatibility antigens, human chorionic gonadotropin (HCG), thyroid-stimulating hormone (TSH), lectin, selectins, cell receptor proteins, calnexin, calreticulin, notch proteins, or the like, while exemplary glycopeptides include, but are not limited to, antibiotics such as vancomycin, teicoplanin, telavancin, bleomycin, ramoplanin, and decaplanin.

The terms "polypeptide" and "protein" are used interchangeably and refer to any polymer of amino acids (dipeptide or greater) linked through peptide bonds or modified peptide bonds, whether produced naturally or synthetically.

The term "pendant group" refers to any functional group that may be attached to, and forms a side-chain of a macromolecule. Typically, the pendant group is attached to the backbone of the macromolecule. For example, in the case of a glycopeptide, the carbohydrate molecule may form the pendant group that is attached to the polypeptide backbone of the glycopeptide, via linkages such as O-glycosidic or N-glycosidic bonds. Exemplary pendant groups on the polypeptide backbone of a glycopeptide include, but are not limited to, monosaccharides, disaccharides, oligosaccharides and polysaccharides.

The term "pre-determined," for example, when used with reference to positions along the polyproline backbone of the glycopeptide of the present disclosure, refers to any position along the polyproline backbone that has been selected for attachment of one or more carbohydrate molecules. The position(s) may, for example, have been selected for attachment of one or more carbohydrate molecules to modulate one or more biological functions of the glycopeptide, for example improved molecular stability, improved selectivity or specificity, improved binding affinity, or the like.

The term "attach," and variations of that term including "attaching" and "attachment," refers to any form of association of one molecule to another, either directly or indirectly (such as via a linker), via any means including but not limited to a covalent bond, via hybridization, via non-covalent interactions, such as receptor-ligand interactions.

The term "alkyne-functionalised" refers to the incorporation of an alkyne functional group into a molecule, typically to facilitate subsequent chemical reaction to take place with or via the alkyne functional group.

The term "treatment" includes any and all uses which remedy a disease state or symptoms, prevent the establishment of disease, or otherwise prevent, hinder, retard, or reverse the progression of disease or other undesirable symptoms in any way whatsoever. Hence, "treatment" includes prophylactic and therapeutic treatment.

The term "patient" refers to patients of human or other mammal and includes any individual it is desired to examine or treat using the methods of the disclosure. However, it will be understood that "patient" does not imply that symptoms are present. Suitable mammals that fall within the scope of the disclosure include, but are not restricted to, primates, livestock animals (e.g. sheep, cows, horses, donkeys, pigs), laboratory test animals (e.g. rabbits, mice, rats, guinea pigs, hamsters), companion animals (e.g. cats, dogs) and captive wild animals (e.g. foxes, deer, dingoes).

The term "administering" and variations of that term including "administer" and "administration", includes contacting, applying, delivering or providing a compound or composition of the disclosure to an organism, or a surface by any appropriate means.

The term "target-specific" when used in relation to therapy such as in "target-specific therapy," it is meant the administration of a compound, for example a drug (such as a glycopeptide of the present disclosure), to a patient in need of therapy, that is capable of binding to a particular biological target to cause a desired biological or therapeutic effect on the patient in order to treat the patient. Similarly, "target-specific therapeutic agent" refers to a therapeutic agent that is specific to a particular target molecule or disease (for example a target-specific drug), while "target-specific biopolymer" refers to a biopolymer that binds to a particular biological target.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF EMBODIMENTS

Exemplary, non-limiting embodiments of a glycopeptide, a method for synthesizing the glycopeptide, and uses of the glycopeptide, as well as a method of controlling the binding affinity of a glycopeptide to its binding molecules will now be disclosed.

In a first aspect, there is provided a glycopeptide, comprising a polyproline backbone and one or more carbohydrate molecules. The polyproline backbone of the glycopeptide may comprise (4R)-azidoproline (Azp). In other words, the polyproline backbone may be azido-functionalised.

In one embodiment, the polyproline backbone has the following general formula (I):

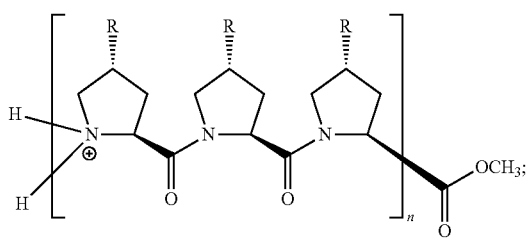

(I)

wherein R is H or N₃, and n is a positive integer. In one embodiment, n is at least 1. Alternatively, n may be at least 2, at least 3, at least 4 or at least 5. For example, n may be 1, 2, 3, 4, 5, 6, 7, 8, 9, 10, 11, 12, 13, 14, 15, 20, 30, 40, 50, or more. In one embodiment, n is 4. In another embodiment, n is 8. In yet another embodiment, n is 12.

The carbohydrate molecules may be attached at predetermined positions along the polyproline backbone. The type of carbohydrate may be selected based on the biological target (for example, a protein) to be bound. For example, where the biological target is nerve growth factor (NGF), a suitable carbohydrate for forming the glycopeptide may be chondroitin sulfate (CS). Other suitable carbohydrates may be used in place of CS. The person skilled in the art would be able to determine the type of carbohydrate that is suitable for forming the glycopeptide in order to bind a desired biological target. The positioning of the carbohydrate(s) on the polyproline backbone may be determined based on factors such as the type and/or structure of the carbohydrate molecules used, and also the type and/or structure (e.g. the crystal structure) of the desired biological target.

In one embodiment, the carbohydrate molecules are attached at equal distances from each other along the polyproline backbone. The inventors have advantageously found that increasing the distance between the carbohydrate molecules and maintaining a minimum spacer length between proline and sugar units allow maximal positional control of the carbohydrate units and enhance binding affinity of the glycopeptide to its binding molecule(s). For example, a carbohydrate molecule may be present on every proline unit on the polyproline backbone, or it may be present on every second proline unit on the polyproline backbone, or it may be present on every third proline unit on the polyproline backbone. In one embodiment, a carbohydrate molecule is present on every third proline unit on the polyproline backbone. A person skilled in the art would be also able to determine the optimal minimum spacer length based on the biological target to be bound by the glycopeptide.

The carbohydrate molecules may be attached along all faces of the polyproline backbone. Alternatively, the carbohydrate molecules may be attached along the same face of the polyproline backbone. The inventors have advantageously found that arranging the carbohydrate molecules along a single face of the polyproline backbone enhances the binding affinity of the glycopeptide to its binding molecule(s).

Binding molecules of a glycoprotein may include molecules such as, but not limited to, cell surface receptors, hormones, proteins, other glycoproteins, peptides, carbohydrates such as lectins or selectins, or may include targets such as viruses, cells, bacteria, or the like.

The polyproline backbone may be rigid, or semi-flexible.

In one embodiment, the one or more carbohydrate molecules may be alkyne-functionalized. Alkyne-functionalization enables the one or more carbohydrate molecules to be incorporated into the PPII helix of the polyproline backbone. Other functional groups known in the art may be used for this purpose. For example, amine-functionalized carbohydrate molecules may be used, which can be conjugated to the polyproline backbone via an amide coupling reaction.

The one or more carbohydrate molecules may be selected from the group consisting of a monosaccharide, a disaccharide, an oligosaccharide and a polysaccharide. Exemplary monosaccharides include, but are not limited to, β-D-Glucose, β-D-galactose, β-D-mannose, α-L-fucose, N-acetylgalactosamine, N-acetylglucosamine, N-acetylneuraminic acid, xylose, or the like. Exemplary disaccharides include, but are not limited to, sucrose, lactulose, lactose, maltose, trehalose, cellobiose chondroitin sulfate, heparin, heparin sulfate, dermatan sulfate, hyaluronan, keratan sulfate, or the like. Exemplary oligosaccharides include, but are not limited to, raffinose, stachyose, fructooligosaccharides, galactooligosaccharides isomaltotriose, maltotriose, melezitose. Exemplary polysaccharides include, but are not limited to, cellulose, chitin, starch, glycogen, pectin, callose or laminarin, chrysolaminarin, xylan, arabinoxylan, mannan, fucoidan and galactomannan.

In one embodiment, the one or more carbohydrate molecule is a disaccharide. For example, the disaccharide may be a chondroitin sulfate, a heparin, a heparin sulfate, a dermatan sulfate, a hyaluronan, or a keratan sulfate. The chondroitin sulfate may be selected from the group consisting of chondroitin sulfate A, chondroitin sulfate C, chondroitin sulfate D and chondroitin sulfate E. In one embodiment, the chondroitin sulfate is chondroitin sulfate E.

The glycopeptide may further comprise one or more polyethylene glycol (PEG) units at one end of the polyproline backbone. Advantageously, incorporation of one or more PEG units enables introduction of the desired functionalities to facilitate conjugation of one or more reporter molecules to the PEG-glycopeptide complex, or to facilitate immobilization of the glycopeptide to a surface. For example, about 1, 2, 3, 4, 5, 6, 7, 8, 9, 10, 11, 12, 13, 14, 15, or more PEG units may be incorporated at one end of the polyproline backbone. In one embodiment, 12 PEG units are incorporated at one end of the polyproline backbone. The PEG may be biotin-conjugated to facilitate immobilization of the glycopeptide to a surface, for example for use in analysis (such as for immobilizing the glycopeptide onto streptavidin-coated plates in ELISA analysis, or onto streptavidin coated chips for surface plasmon resonance), and to facilitate purification of glycopeptide by techniques such as affinity chromatography or affinity pull-down assays. Biotinylation may also facilitate the labeling of the glycopeptide such as with an enzyme reporter or a fluorescent probe for use as an in vivo diagnostic reagent.

In one embodiment, the glycopeptide has the following general formula (II):

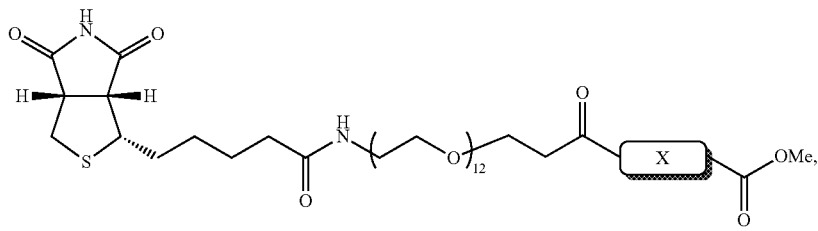

II wherein X is a glycopeptide as defined above.

The X may be a formula selected from the group consisting of: $(P_E)_{12}$, $(P_E)_4G$ $(P_E)_4G$ $(P_E)_4$, $(PP_E)_{12}$, $(PPP_E)_{12}$, $(P_U)_{12}$ and $(PPP_U)_{12}$, wherein P is proline;
G is glycine;
$P_E$ is

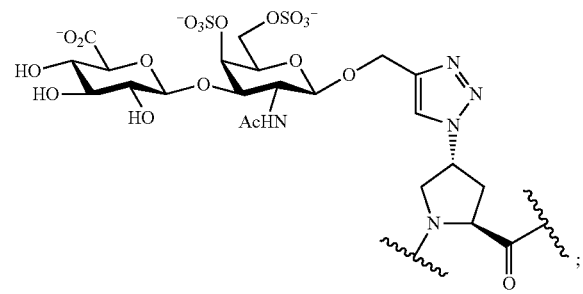

and
$P_U$ is

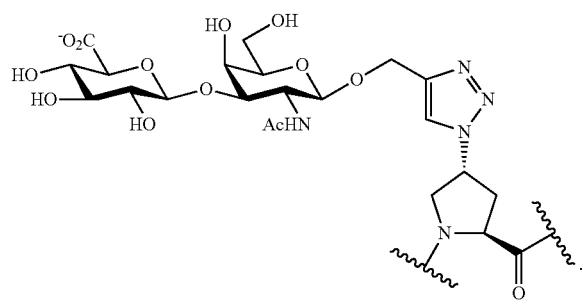

In one embodiment, the glycopeptide may further comprise a lipid. The lipid may be a fatty acid, glycerolipid, glycerophospholipid, sphingolipid, saccharolipid, polyketide, a sterol lipid, a prenol lipid, or the like.

In a second aspect, there is provided a method of synthesising a glycopeptide as defined above, comprising attaching one or more carbohydrate molecules to a polyproline backbone. The carbohydrate molecules may be alkyne-functionalised while the polyproline backbone may be azido-functionalised as discussed above.

In one embodiment of the method, the one or more carbohydrate molecules are attached to the polyproline backbone via a click reaction. The click reaction may be conducted in DMSO at ambient temperature for about 7 days in the presence of copper(I) idode, N,N-diisopropylethylamine (DIPEA) and tris[(1-benzyl-1H-1,2,3-triazol-4-yl)methyl]amine (TBTA) under argon atmosphere. Other suitable methods for attaching the carbohydrate molecules to the polyproline backbone that are known in the art may be used.

The method may further comprise the steps of:
(i) precipitating the reaction mixture resulting from the click reaction from a THF/methanol mixture;
(ii) converting the reaction mixture into their sodium salt form; and
(iii) purifying the salt by size-exclusion chromatography.

In one embodiment, the carbohydrate molecules are alkyne-functionalised chondroitin sulfate disaccharides. The alkyne-functionalised chondroitin sulfate disaccharides may be synthesised by:
(i) converting tricholoroacetimidate 8

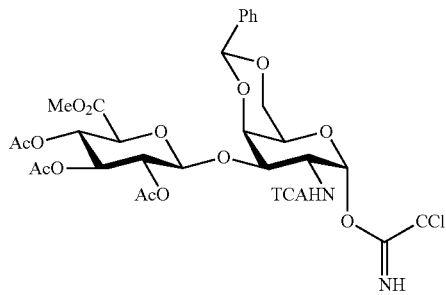

to the fully protected disaccharide 9

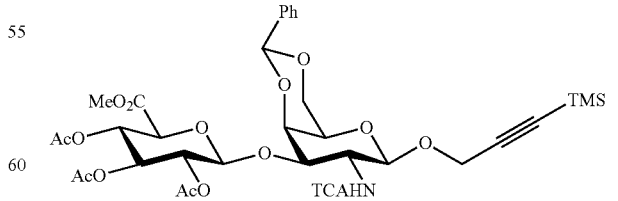

using trimethylsilyl triflate;
(ii) reducing N-trichloroactyl group to N-acetyl congener with n-tributylstannane and AIBN by radical-mediated reduction to yield the acetamide 10

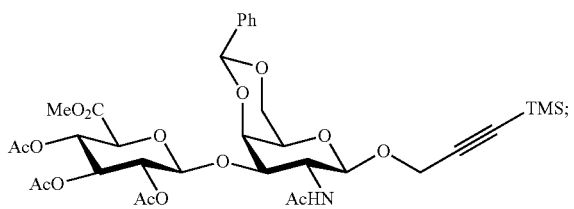

(iii) hydrolysing the benzylidene acetal followed by removing the TMS group to produce the diol 11

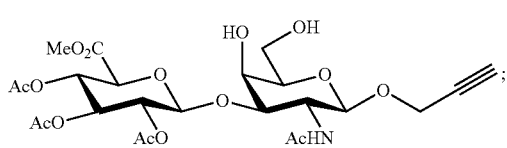

(iv) optionally treating the diol 11 with SO₃ trimethylamine complex; and (v) treating the resultant mixture with LiOOH and NaOH.

The polyproline backbone may be synthesised using protein synthesis methods that are known in the art such as via solid-phase peptide synthesis (for example using Fmoc or Boc as the protecting group(s)), or solution-phase peptide synthesis.

In one embodiment, the method comprises synthesizing the polyproline backbone via solution-phase peptide synthesis. The solution-phase peptide synthesis may comprise the steps of:

(i) coupling the Boc protected amino acid with amino acid methyl ester using O-(Benzotriazol-1-yl)-N,N,N',N'-tetramethyluronium tetrafluoroborate (TBTU) as the coupling reagent;

(ii) removing Boc and methyl ester protective groups of the resulting peptides prior to the next coupling reactions by treatment with a $CF_3CO_2H/CH_2Cl_2$ mixture and aqueous NaOH, respectively;

(iii) repeating steps (i) and (ii) until the desired polyproline derivates are obtained; and (iv) purifying the polyproline derivatives by flash column chromatography on silica or reverse phase HPLC.

In a third aspect, there is provided a glycopeptide as defined above for use in therapy.

In a fourth aspect, there is provided a method of treating a patient in need of a target-specific therapy, comprising the administration of a glycopeptide as defined above. Exemplary target-specific therapy in which a glycopeptide as defined above may be useful includes, but is not limited to, cancer therapy, HIV-therapy, and therapy against diseases such as neurodegenerative diseases (e.g. Parkinson's disease, Alzheimer's disease, etc.), bone diseases, cartilage diseases, immunological diseases (e.g. rheumatoid arthritis, osteoporosis), inflammatory diseases, and infections such as bacterial infections, viral infections, and fungal infections.

In a fifth aspect, there is provided a target-specific therapeutic agent comprising a glycopeptide as defined above. Exemplary target-specific therapeutic agents in which a glycopeptide as defined above may be useful include, but are not limited to, anti-cancer agents, anti-HIV agents, anti-inflammatory agents, anti-bacterial agents, anti-viral agents, anti-fungal agents, antibiotics, neuronal promoters, or the like.

In a sixth aspect, there is provided a glycopeptide as defined above for use as target-specific biopolymers. Exemplary target-specific biopolymers in which a glycopeptide as defined above may be useful include, but are not limited to, anticoagulants (such as anticoagulant heparin mimetics), modulators of physiological activity (such as modulators of chemokine activity with clinical relevance to diseases such as atherosclerosis, cancer, and autoimmune disorders), anti-dengue agents, anti-malarial agents, or the like.

In a seventh aspect, there is provided a glycopeptide as defined above for use in GAG-based pharmaceutics. Exemplary GAG-based pharmaceutics in which a glycopeptide as defined above may be useful include, but are not limited to, anticoagulants (such as anticoagulant heparin mimetics), modulators of physiological activity (such as modulators of chemokine activity with clinical relevance to diseases such as atherosclerosis, cancer, and autoimmune disorders), anti-dengue agents, anti-malarial agents, or the like.

In an eighth aspect, there is provided a glycopeptide as defined above for use as diagnostic tools. Exemplary diagnostic tools in which a glycopeptide as defined above may be useful include, but are not limited to, a diagnostic tool for cancer, infection (e.g. bacterial, viral or fungal infection), substance abuse, or the like.

In a ninth aspect, there is provided a method of controlling the binding affinity of a glycopeptide to one or more binding molecules, comprising attaching one or more carbohydrate molecules at pre-determined positions along a polyproline backbone. The polyproline backbone may comprise (4R)-azidoproline (Azp) as discussed above. In one embodiment, the polyproline backbone is of the following general formula (I):

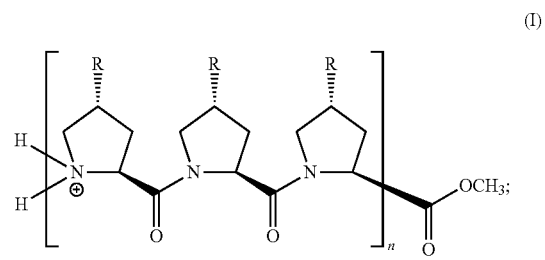

wherein R is H or N₃, and n is a positive integer. The n may be at least 1, as discussed above. The polyproline backbone may be rigid, or semi-flexible. In one embodiment of the method of controlling the binding affinity of a glycopeptide to one or more binding molecules, the carbohydrate molecules are attached at pre-determined positions along the polyproline backbone. For example, the carbohydrate molecules may be attached at equal distances from each other along the polyproline backbone and along the same face of the polyproline backbone as discussed above.

In a tenth aspect, there is provided a polyproline backbone, comprising (4R)-azidoproline (Azp). The polyproline backbone may be used in manufacturing a glycopeptide comprising carbohydrate molecules at pre-determined positions along the backbone as discussed above.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

DETAILED DESCRIPTION OF DRAWINGS

Examples

Non-limiting examples of the invention, including the best mode, and a comparative example will be further described in greater detail by reference to specific Examples, which should not be construed as in any way limiting the scope of the invention.

Example 1—General Methods

Unless otherwise stated, reactions were performed in flame-dried glassware under argon atmosphere and using dry solvents. All commercially obtained reagents were used as received unless otherwise noted. Thin layer chromatography (TLC) was performed using E. Merck silica gel 60 F254 precoated plates (0.25 mm). Visualization of the developed chromatogram was performed by UV, cerium ammonium molybdate or ninhydrin stain as necessary. Merck silica gel 60 (particle size 0.040-0.063 mm) was used for flash chromatography. Gel filtration chromatography (Sephadex G-15 ultrafine) was used in order to achieve purification of the glycopeptides.

$^1$H NMR and proton decoupling experiments were recorded on a Bruker AVIII (400 MHz) spectrometer and are reported in parts per million (δ) relative to CDCl$_3$ (7.26 ppm), CD$_3$OD (4.87 ppm), and D$_2$O (4.80 ppm). Data for the $^1$H NMR spectra are reported as follows: chemical shift (5 ppm), multiplicity (s=singlet, bs=broad singlet, d=doublet, t=triplet, q=quartet, m=multiplet), coupling constant in Hz, and integration. $^{13}$C NMR spectra were obtained on a Bruker AVIII (100 MHz) spectrometer and are reported in terms of chemical shift. Mass spectra were obtained from Chemical, Molecular and Materials Analysis Centre at the National University of Singapore.

3-Trimethylsilylpropargyl O-(methyl 2,3,4-tri-O-acetyl-β-D-glucopyranosyluronate)-(1→3)-4,6-O-benzylidene-2-deoxy-2-trichloroacetamido-β-D-galactopyranoside 9

Figure 1:
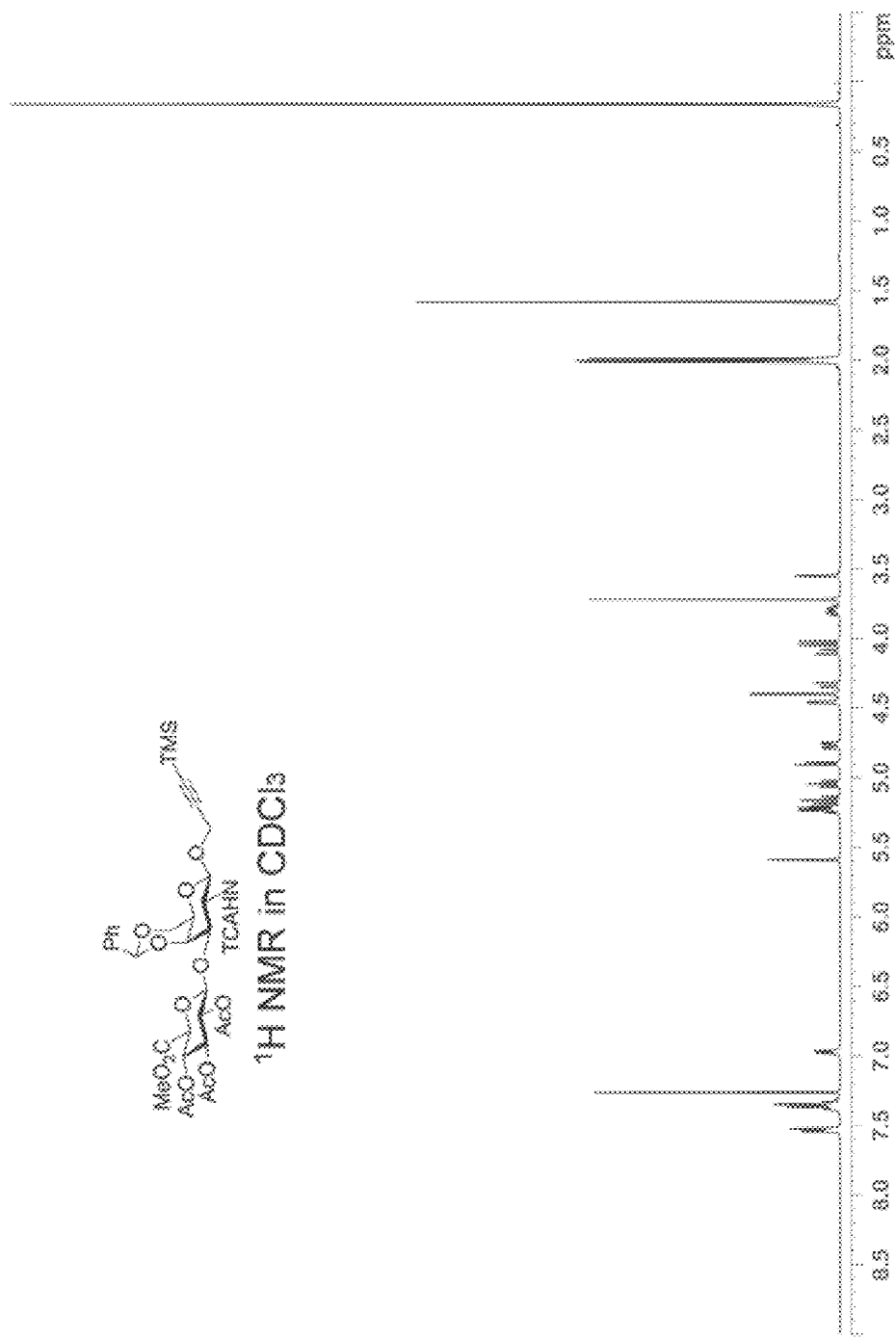
FIG. 1 shows the $^1$H NMR spectra of the fully protected disaccharide 9, after conversion from trichloroacetimidate 8 in one embodiment of the method of synthesizing the glycopeptide as defined above as depicted in the schematic of FIG. 30.
Figure 2:
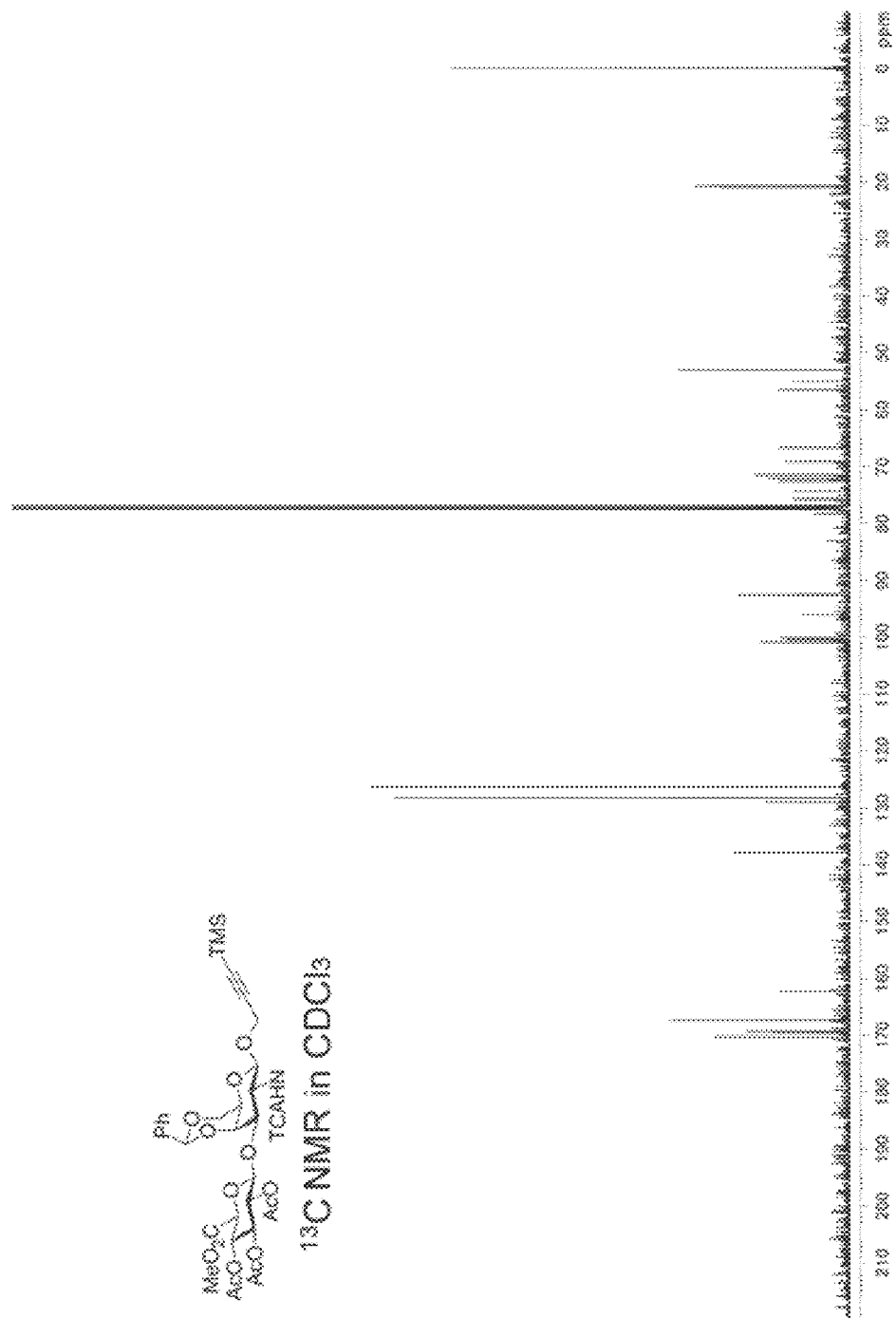
FIG. 2 shows the $^{13}$C NMR spectra of the fully protected disaccharide 9, after conversion from trichloroacetimidate 8 in one embodiment of the method of synthesizing the glycopeptide as defined above as depicted in the schematic of FIG. 30.

Donor 8 (0.500 g, 0.573 mmol) was co-evaporated with toluene (3×5 mL) and dried under vacuum overnight. To a solution of 8 and 3-trimethylsilylpropargyl alcohol (0.425 mL, 2.863 mol) in dry CH$_2$Cl$_2$ (7.35 mL) was added 4 Å powdered molecular sieves. The reaction was stirred at room temperature for 30 min, cooled to −78° C., and then stirred for an additional 30 min. Trimethylsilyl trifluoromethanesulfonate (0.227 mM in CH$_2$Cl$_2$, 0.115 mmol, 500 µL) at −78° C. was added to the reaction dropwise. The reaction was warmed to −15° C., stirred for 2 hrs, and quenched with triethylamine. The reaction mixture was filtered through Celite and concentrated to afford yellow syrup. The product was purified by flash chromatography (1%→2% 2-propanol:CH$_2$Cl$_2$) to afford slightly impure 9 as a light yellow solid. The impure 9 was then purified one more time by flash chromatography (2%→5% THF:[2:1 hexanes:CH$_2$Cl$_2$]) to afford pure 9 (0.295 g, 61%) as a white solid. R$_f$=0.45 (6:3:1 CH$_2$Cl$_2$:hexanes:THF). $^1$H NMR (400 MHz, CDCl$_3$): δ 7.53 (m, 2H, ArH), 7.38-7.33 (m, 3H, ArH), 6.97 (d, J=6.8 Hz, 1H, NH), 5.59 (s, 1H, PhCH), 5.23 (d, J=8.2 Hz, 1H, H-1'), 5.23 (t, J=9.4 Hz, 1H, H-4), 5.16 (t, J=8.8 Hz, 1H, H-3), 5.04 (t, J=7.8 Hz, 1H, H-2), 4.90 (d, J=7.5 Hz, 1H, H-1), 4.77 (dd, J=11.1, J=3.4 Hz, 1H, H-3'), 4.46 (d, J=3.3 Hz, 1H, H-4'), 4.40 (s, 2H, CH$_2$—C≡C), 4.33 (d, J=12.4 Hz, 1H, H-6'), 4.10 (d, J=11.6 Hz, 1H, H-6'), 4.03 (d, J=9.7 Hz, 1H, H-5), 3.83-3.77 (m, 1H, H-2'), 3.72 (s, 3H, OCH$_3$), 3.55 (s, 1H, H-5'), 2.01 (s, 3H, C(O)CH$_3$), 2.01 (s, 3H, C(O)CH$_3$), 2.00 (s, 3H, C(O)CH$_3$), 1.99 (s, 3H, C(O)CH$_3$), 0.16 (s, 3H, SiCH$_3$); $^{13}$C NMR (100 MHz, CDCl$_3$): δ 170.20, 169.57, 169.32, 167.32, 162.27, 137.80, 128.99, 128.24, 126.33, 100.83, 100.40, 100.17, 96.10, 92.54, 92.48, 75.76, 74.22, 72.57, 72.12, 71.40, 69.22, 69.14, 66.76, 56.53, 55.03, 53.04, 20.97, 20.72, 20.63, −0.06; ESI MS: m/z calcd for [C$_{34}$H$_{42}$Cl$_3$NO$_{15}$Si+Na]$^+$: 860.1287, obsd 860.1296. The $^1$H NMR spectrum of 9 is shown in FIG. 1, and its $^{13}$C NMR spectrum is shown in FIG. 2.

3-Trimethylsilylpropargyl O-(methyl 2,3,4-tri-O-acetyl-β-D-glucopyranosyluronate)-(1→3)-4,6-O-benzylidene-2-deoxy-2-acetamido-β-D-galactopyranoside 10

Figure 3:
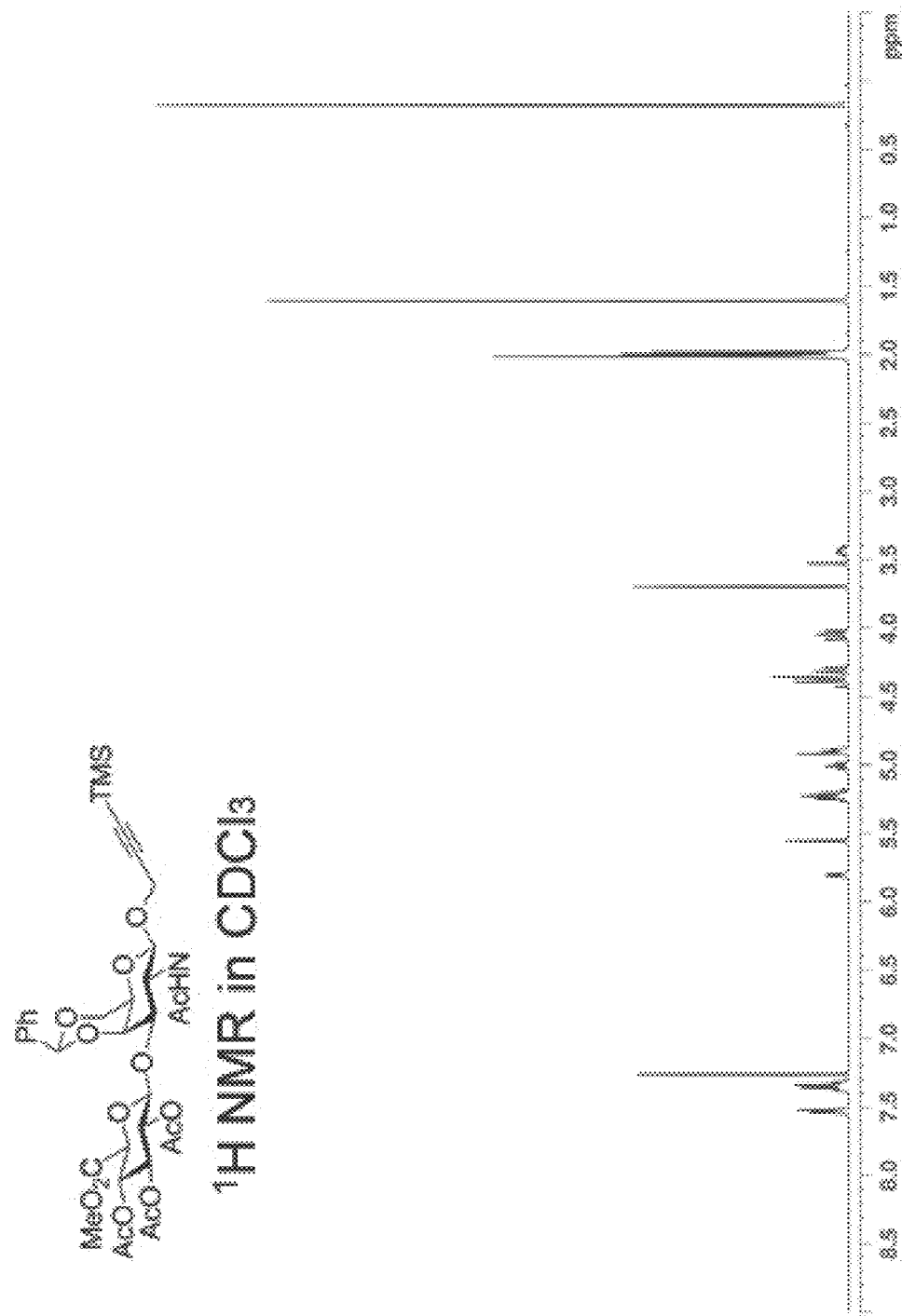
FIG. 3 shows the $^1$H NMR spectra of the acetamide 10 after radical-mediated reduction of N-trichloroacytl group to N-acetyl congener with n-tributylstannane and AIBN in one embodiment of the method of synthesizing the glycopeptide as defined above as depicted in the schematic of FIG. 30.
Figure 4:
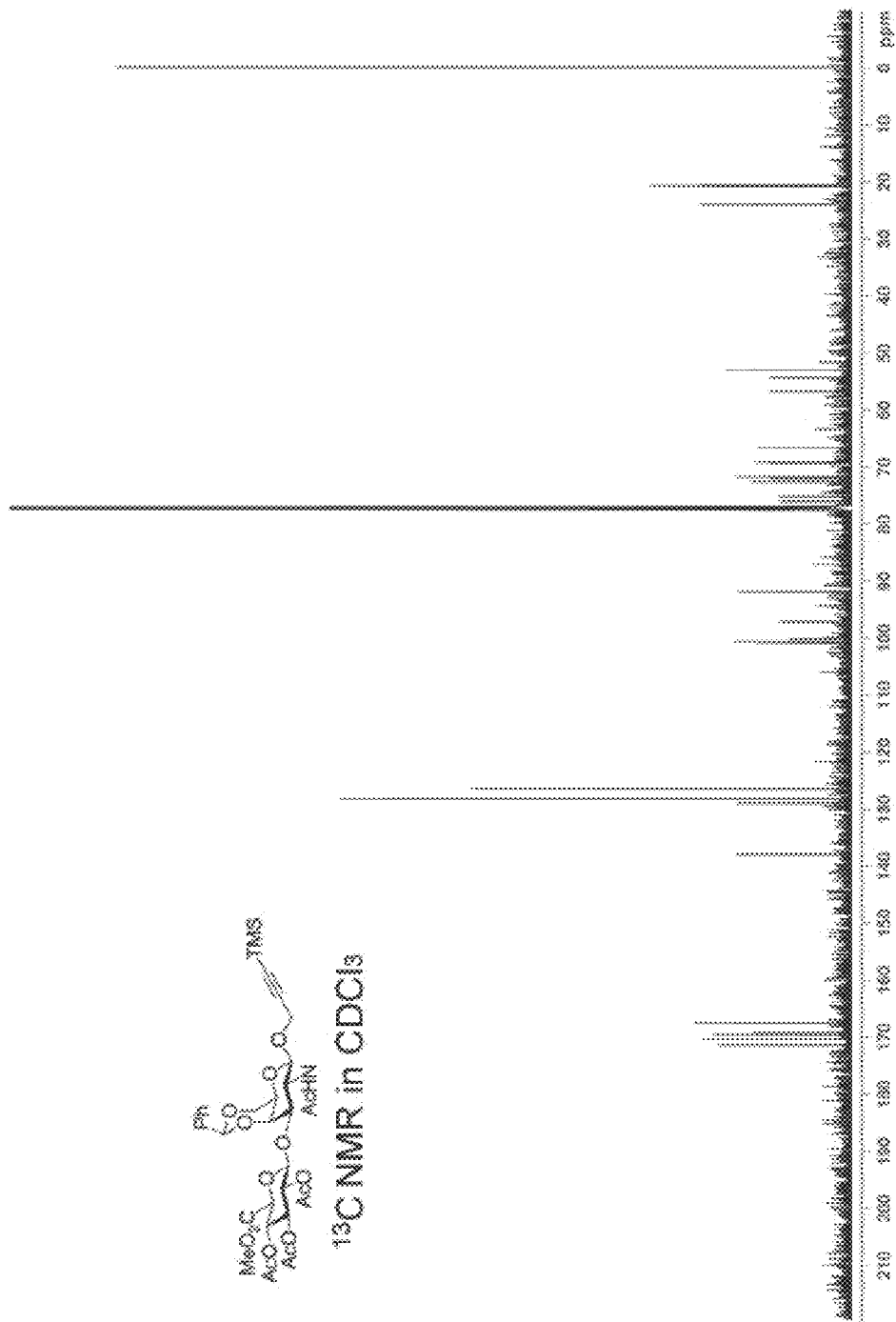
FIG. 4 shows the $^{13}$C NMR spectra of the acetamide 10 after radical-mediated reduction of N-trichloroacytl group to N-acetyl congener with n-tributylstannane and AIBN in one embodiment of the method of synthesizing the glycopeptide as defined above as depicted in the schematic of FIG. 30.

Reduction of the trichloroacetamide group was performed using a procedure modified from Bélot et. al.[1] Disaccharide 9 (0.353 g, 0.421 mmol) was dissolved in toluene (8.7 mL), and tributylstannane (1132 µL, 4.21 mmol) and 2,2'-azobisisobutyronitrile (34.5 mg, 0.211 mmol) were added. After stirring at room temperature for 30 min, the reaction mixture was heated to 80° C. and stirred for an additional 4 h 30 min. The reaction was then cooled to room temperature and concentrated to afford a white solid. The product was purified by flash chromatography (3→11% THF:CH$_2$Cl$_2$) to afford the desired acetamide (0.281 g, 91%) as a white solid. R$_f$=0.25 (4% THF:CH$_2$Cl$_2$). $^1$H NMR (400 MHz, CDCl$_3$): δ 7.53 (m, 2H, ArH), 7.37-7.32 (m, 3H, ArH), 5.81 (d, J=6.6 Hz, 1H, NH), 5.56 (s, 1H, PhCH), 5.25-5.18 (m, 3H, H-3, H-4, H-1'), 5.01 (t, J=7.7 Hz, 1H, H-2), 4.92-4.88 (m, 2H, H-1, H-3'), 4.43-4.36 (m, 3H, H-4', CH$_2$—C≡C), 4.30 (d, J=12.5 Hz, 1H, H-6'), 4.08-4.02 (m, 2H, H-5, H-6'), 3.70 (s, 3H, OCH$_3$), 3.53 (s, 1H, H-5'), 3.47-3.41 (m, 1H, H-2'), 2.02 (s, 6H, NHC(O)CH$_3$, C(O)CH$_3$), 2.00 (s, 3H, C(O)CH$_3$), 1.98 (s, 3H, C(O)CH$_3$), 0.18 (s, 3H, SiCH$_3$); $^{13}$C NMR (100 MHz, CDCl$_3$): δ 171.31, 170.29, 169.59, 169.18, 167.47, 137.90, 128.92, 126.37, 100.85, 100.81, 100.57, 97.07, 91.88, 75.98, 75.16, 72.52, 72.03, 71.74, 69.29, 69.18, 66.60, 56.75, 54.31, 52.98, 23.98, 20.86, 20.75, 20.65, −0.07; ESI MS: m/z calcd for [C$_{34}$H$_{45}$NO$_{15}$Si+Na]$^+$: 758.2456, obsd 758.2469. The $^1$H NMR spectrum of 10 is shown in FIG. 3, and its $^{13}$C NMR spectrum is shown in FIG. 4.

2-Propargyl-O-(methyl 2,3,4-tri-O-acetyl-β-D-glucopyranosyluronate)-(1→3)-2-deoxy-2-acetamido-β-D-galactopyranoside 11

The acetamide (0.353 g, 0.480 mmol) was dissolved in AcOH/water (4:1, 3.0 mL) and stirred at 80° C. After 30 min, the reaction mixture was cooled and concentrated. The resulting concentrate was co-evaporated with toluene (3×3 mL) for the complete removal of AcOH.

Figure 5:
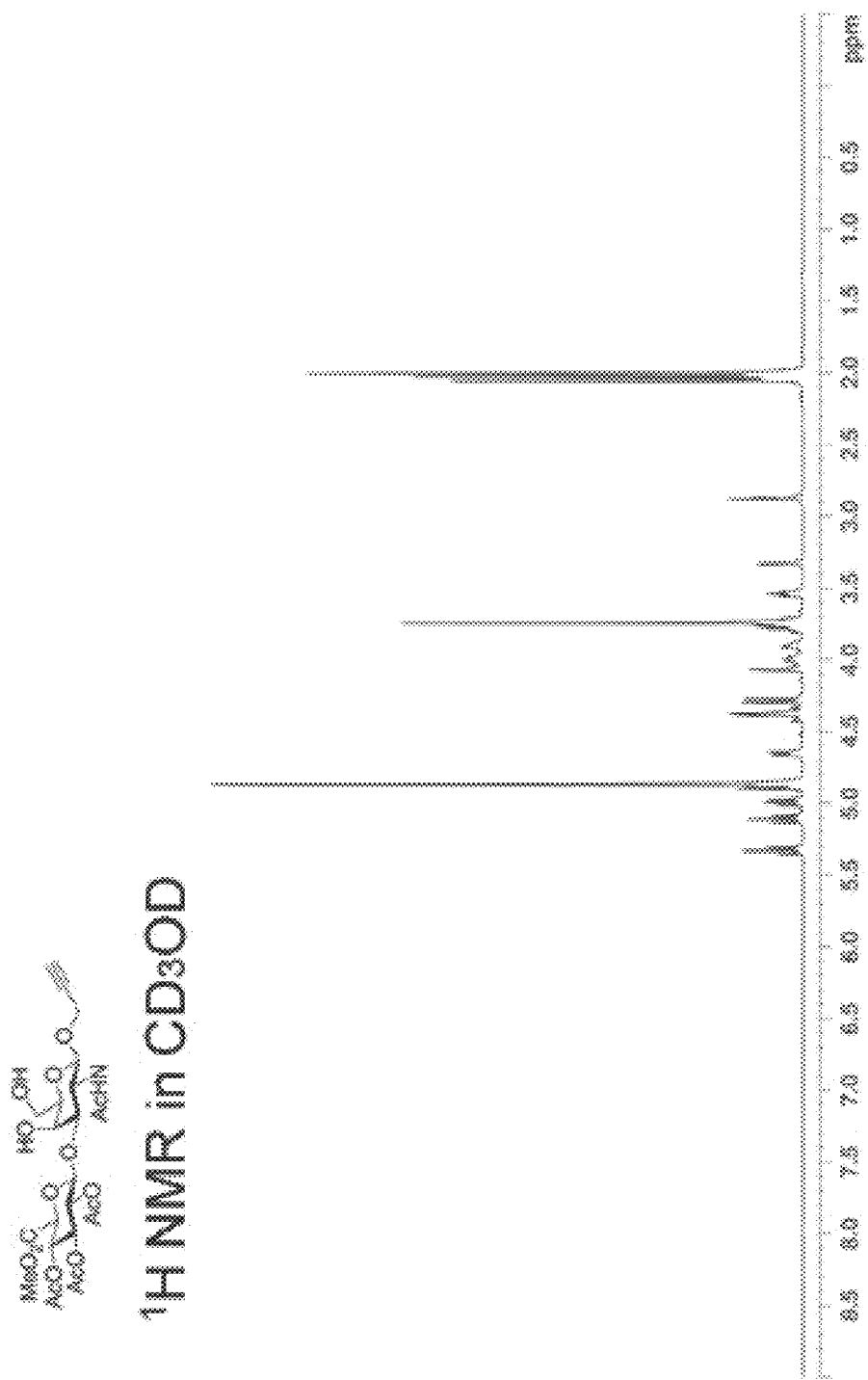
FIG. 5 shows the $^1$H NMR spectra of the diol 11 after hydrolysis of the benzylidene acetal of 10 followed by removal of the TMS group in one embodiment of the method of synthesizing the glycopeptide as defined above as depicted in the schematic of FIG. 30.
Figure 6:
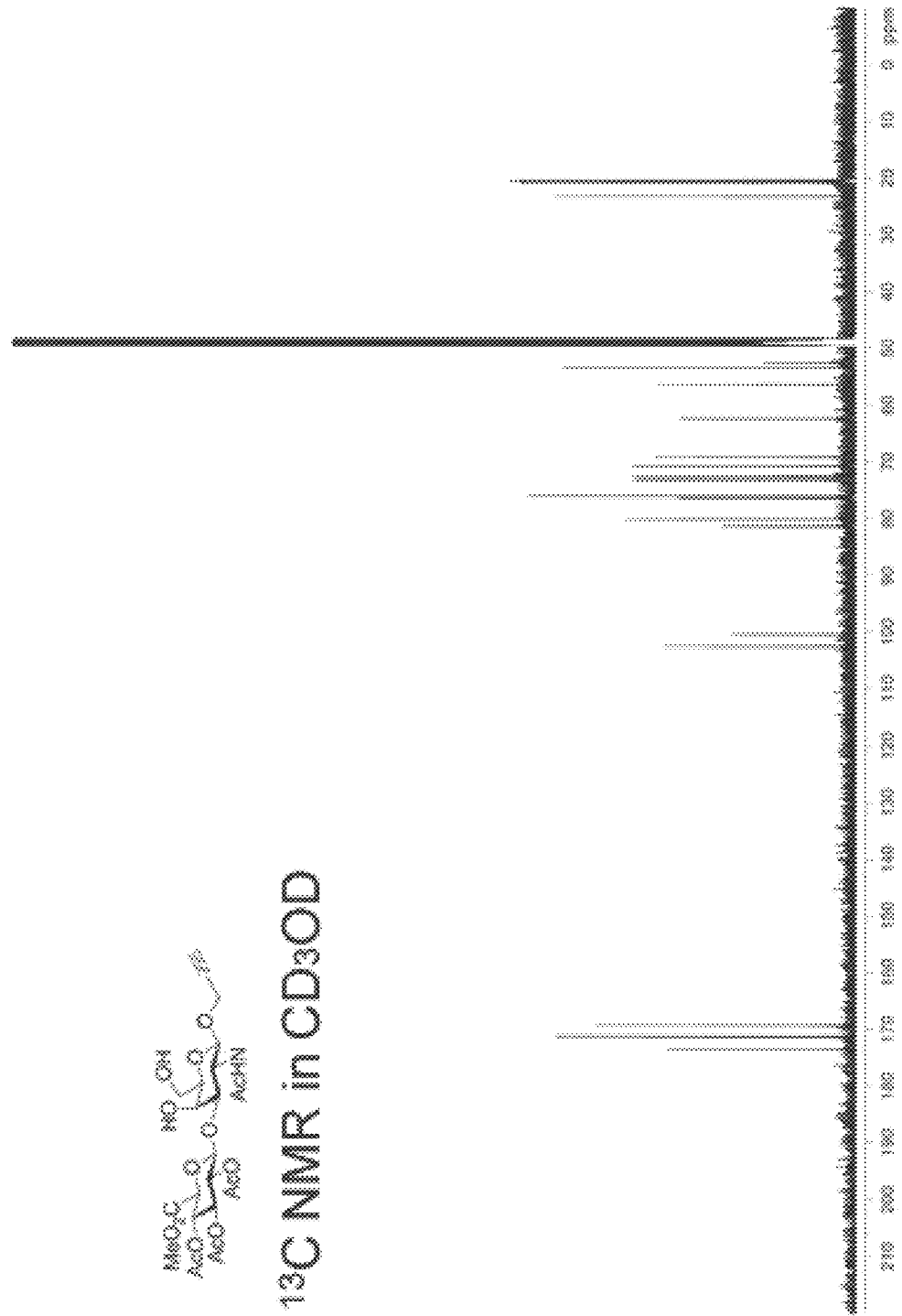
FIG. 6 shows the $^{13}$C NMR spectra of the diol 11 after hydrolysis of the benzylidene acetal of 10 followed by removal of the TMS group in one embodiment of the method of synthesizing the glycopeptide as defined above as depicted in the schematic of FIG. 30.

To a solution of crude diol (0.242 g, 0.374 mmol) in THF (3.7 mL) was added TBAF (1 M solution in THF, 18.8 mmol, 448 µL) and the mixture stirred at 0° C. for 1.5 hr. At this time the addition of Amberlyst IR-120 resin was made and the reaction stirred for a further 30 min. After filtration, the mixture was concentrated to afford a light yellow solid. The residue was purified via flash chromatography (5→7% MeOH:CH$_2$Cl$_2$) to afford the desired compound (0.147 g, 53%) as a white solid. $R_f$=0.30 (10% MeOH:CH$_2$Cl$_2$). $^1$H NMR (400 MHz, CD$_3$OD): δ 5.35 (t, J=6.6 Hz, 1H, H-3), 5.11 (t, J=9.8 Hz, 1H, H-4), 5.00 (dd, J=8.0 Hz, J=9.4 Hz, 1H, H-2), 4.91 (d, J=8.0 Hz, 1H, H-1), 4.66 (d, J=8.2 Hz, 1H, H-1'), 4.43-4.37 (m, 2H, CH$_2$—C≡C), 4.29 (d, J=10.0 Hz, 1H, H-5), 4.07 (bs, 1H, H-4'), 4.00-3.98 (m, 1H, H-2'), 3.91-3.89 (m, 1H, H-3'), 3.81-3.72 (m, 2H, H-6'), 3.75 (s, 3H, OCH$_3$), 3.54 (t, J=5.8 Hz, 1H, H-5'), 2.87 (t, J=2.32 Hz, 1H, C≡CH), 2.06 (s, 3H, NHC(O) CH$_3$), 2.03 (s, 3H, C(O)CH$_3$), 2.01 (s, 3H, C(O)CH$_3$), 2.00 (s, 3H, C(O)CH$_3$); $^{13}$C NMR (100 MHz, CD$_3$OD): δ 173.41, 171.48, 171.21, 169.31, 102.60, 100.50, 81.36, 80.14, 76.47, 76.13, 73.45, 72.95, 72.57, 70.84, 69.17, 62.40, 56.43, 53.41, 52.56, 23.40, 20.97, 20.77, 20.49, 20.41; ESI MS: m/z calcd for [C$_{24}$H$_{33}$NO$_{15}$+Na]$^+$: 598.1748, obsd 598.1760. The $^1$H NMR spectrum of 11 is shown in FIG. 5, and its $^{13}$C NMR spectrum is shown in FIG. 6.

2-Propargyl O-(sodium-β-D-glucopyranosyluronate)-(1→3)-2-deoxy-2-acetamido-β-D-galactopyranoside 12

Figure 7:
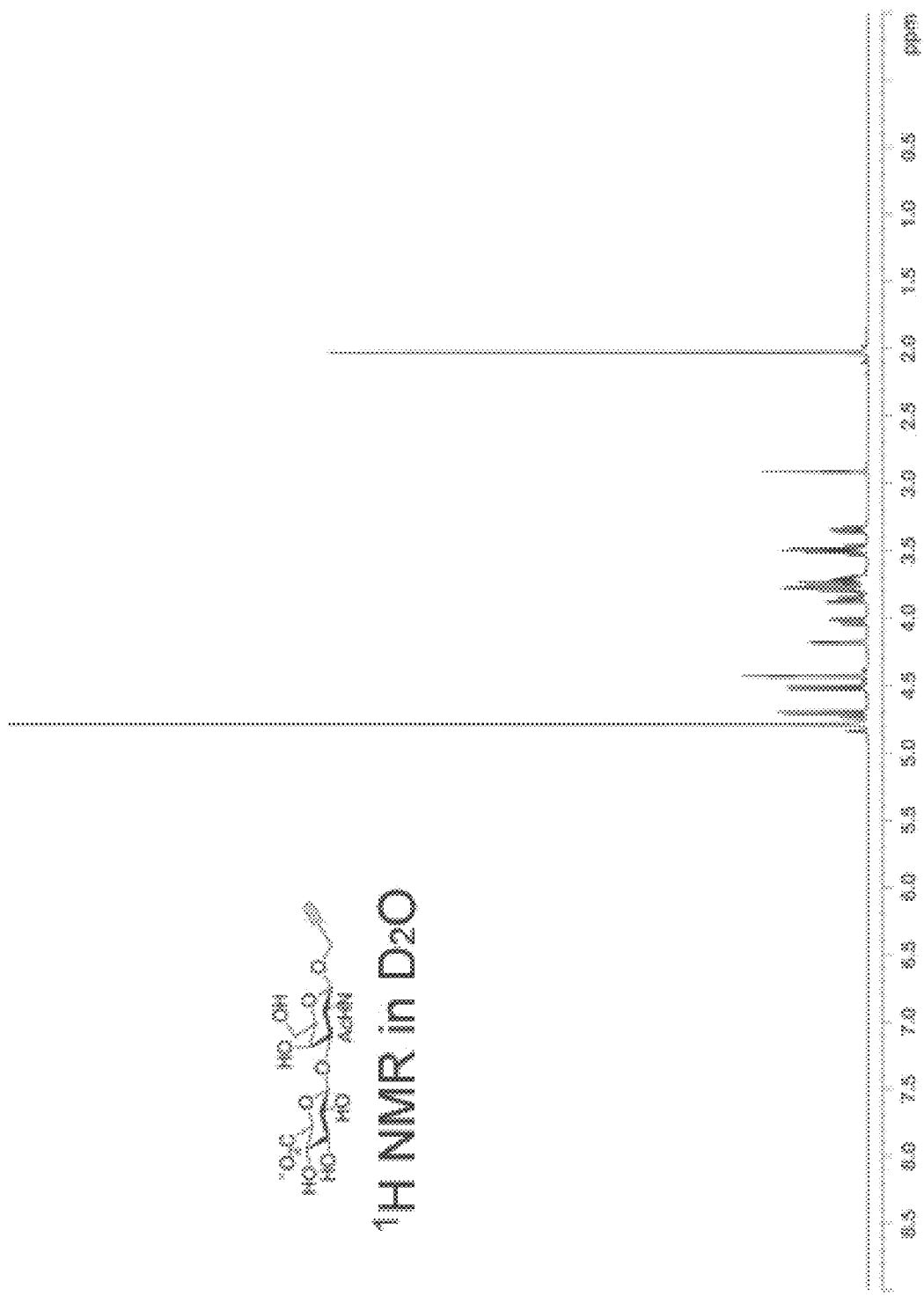
FIG. 7 shows the $^1$H NMR spectra of the unsulfated disaccharide 12 after deprotection of 11 in one embodiment of the method of synthesizing the glycopeptide as defined above as depicted in the schematic of FIG. 30.
Figure 8:
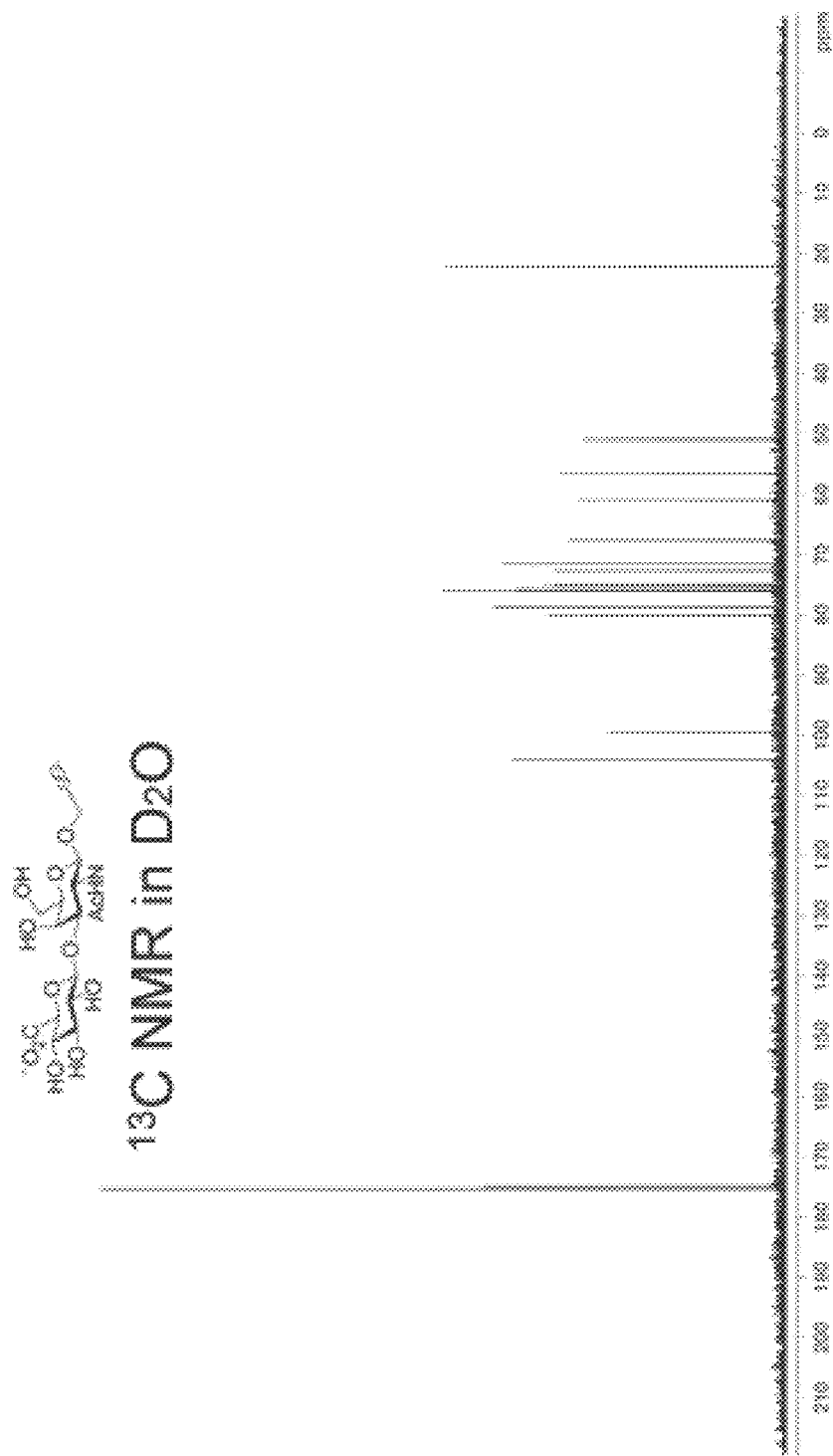
FIG. 8 shows the $^{13}$C NMR spectra of the unsulfated disaccharide 12 after deprotection of 11 in one embodiment of the method of synthesizing the glycopeptide as defined above as depicted in the schematic of FIG. 30.

Compound 11 (40 mg, 0.0695 mmol) was dissolved in THF (684 μL) and H$_2$O (388 μL) and cooled to 0° C. To this were added 1 M aq. LiOH (270 μL) and 30% H$_2$O$_2$ (135 μL). The reaction stirred at 0° C. for 1 hr and at room temperature for 12 hr. At this time, 4 M NaOH (203 μL) and MeOH (1008 μL) were added and the reaction stirred for another 12 hr.[2] It was neutralized with Amberlyst IR-120 resin, filtered, and lyophilized to afford an orange solid. The product was purified by Sephadex G-15 (100% H$_2$O) and lyophilized to afford 12 as a white solid (28.7 mg, 95%). $^1$H NMR (400 MHz, D$_2$O): δ 4.70 (d, J=8.6 Hz, 1H, H-1'), 4.52 (d, J=7.8 Hz, 1H, H-1), 4.44-4.42 (m, 2H, CH$_2$—C≡C), 4.18 (d, J=3.1 Hz, 1H, H-4'), 4.02 (dd, J=10.9, J=9.8 Hz, 1H, H-2'), 3.86 (dd, J=10.8, J=3.2 Hz, 1H, H-3'), 3.81-3.69 (m, 4H, H-5, H-5', H-6', H-6'), 3.53-3.46 (m, 2H, H-3, H-4), 3.37-3.32 (m, 1H, H-2), 2.91 (t, J=2.4 Hz, 1H, C≡CH), 1.94 (s, 3H, NHC(O)CH$_3$); $^{13}$C NMR (100 MHz, D$_2$O): δ 175.38, 174.93, 104.10, 99.57, 80.11, 78.84, 78.83, 76.07, 75.85, 75.25, 75.01, 72.64, 71.68, 67.67, 60.98, 56.56, 50.94, 22.25; ESI MS: m/z calcd for [C$_{17}$H$_{25}$NO$_{12}$-H]$^-$ 434.1299, obsd 434.1308. The $^1$H NMR spectrum of 12 is shown in FIG. 7, and its $^{13}$C NMR spectrum is shown in FIG. 8.

Figure 9:
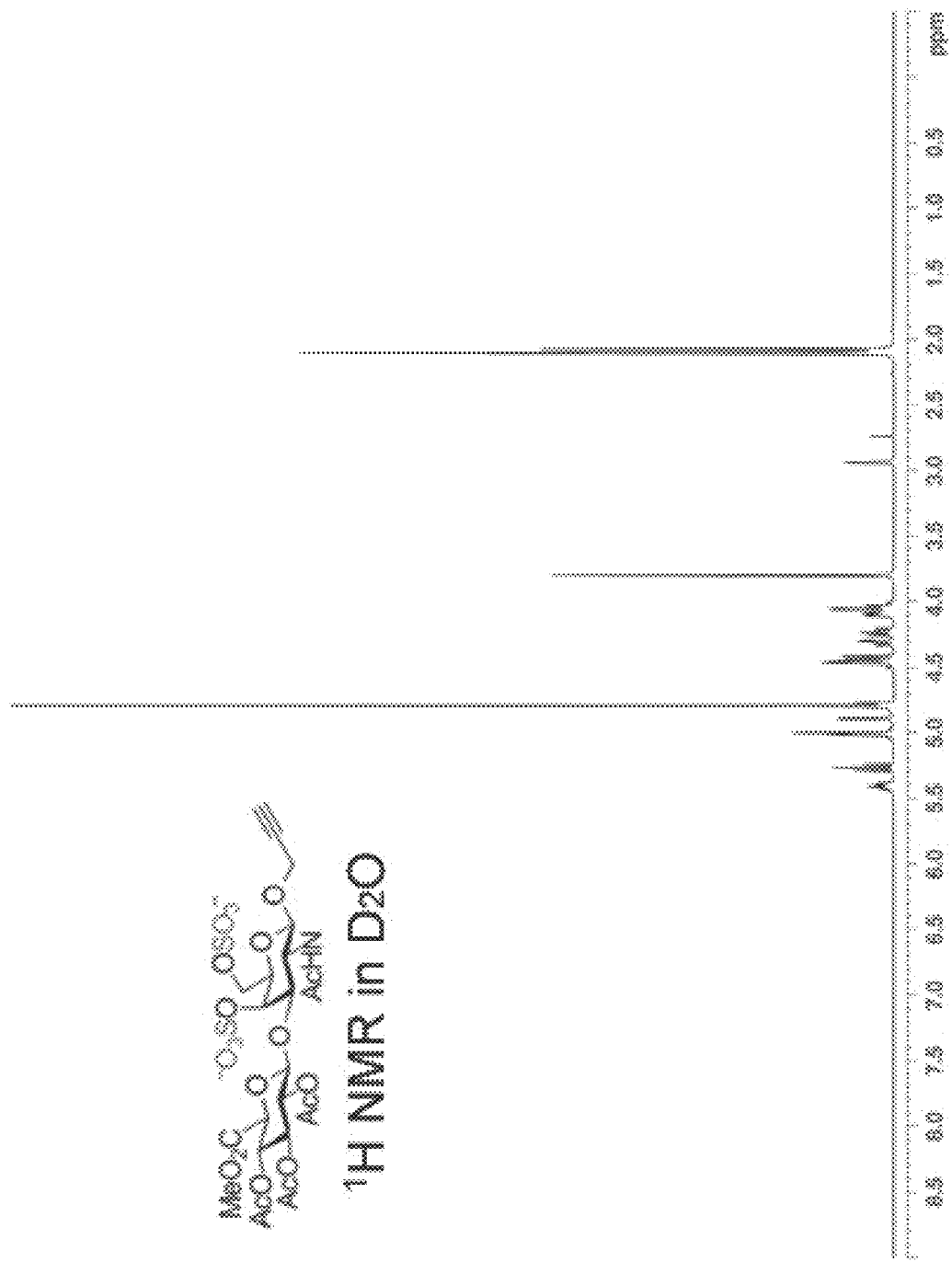
FIG. 9 shows the $^1$H NMR spectra of the sulfate motif after treatment of 11 with $SO_3$.trimethylamine complex in one embodiment of the method of synthesizing the glycopeptide as defined above as depicted in the schematic of FIG. 30.
Figure 10:
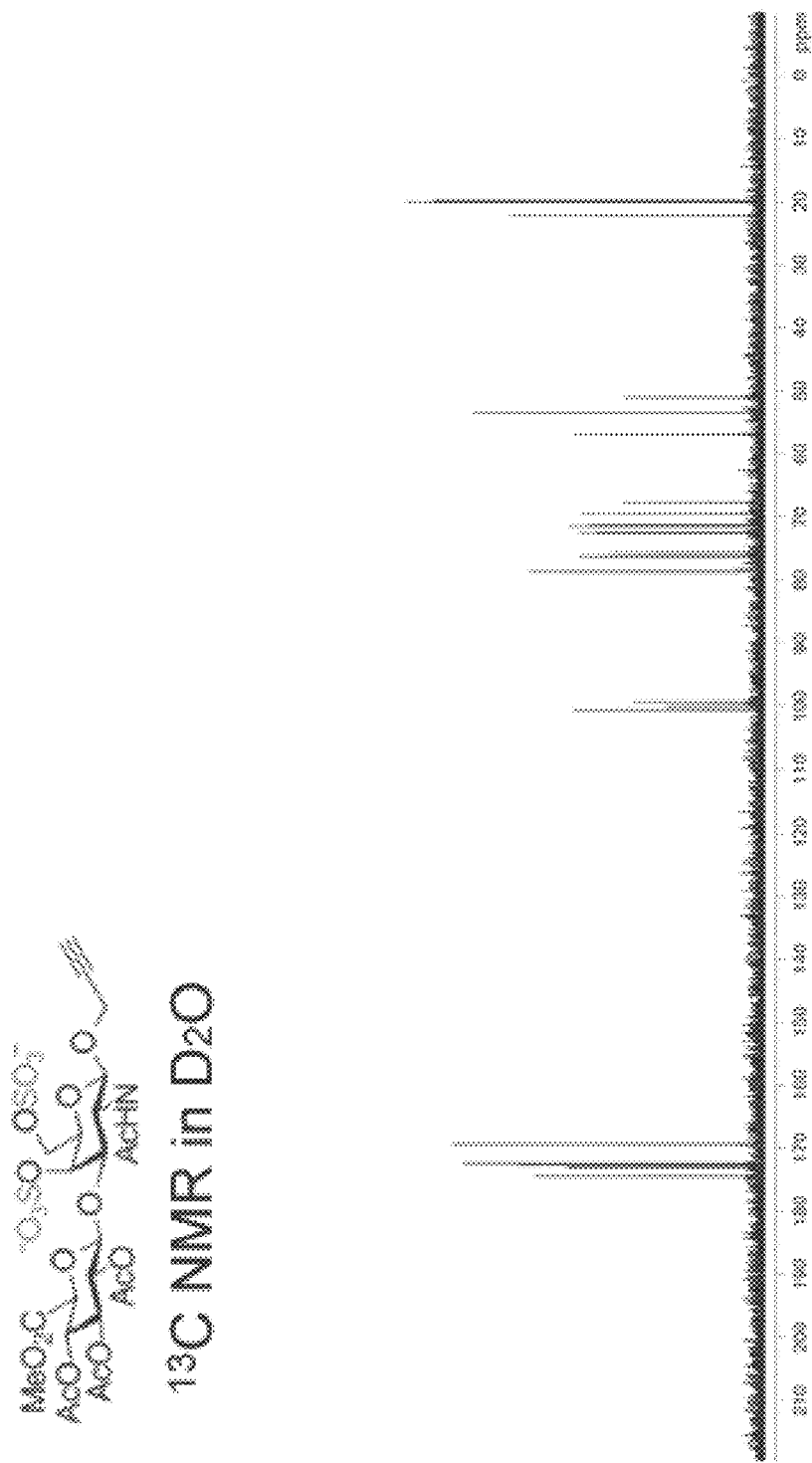
FIG. 10 shows the $^{13}$C NMR spectra of the sulfate motif after treatment of 11 with $SO_3$.trimethylamine complex in one embodiment of the method of synthesizing the glycopeptide as defined above as depicted in the schematic of FIG. 30.

2-Propargyl O-(methyl 2,3,4-tri-O-acetyl-β-D-glucopyrano syluronate)-(1→3)-4,6-di-O-sodium sulfonato-2-deoxy-2-acetamido-β-D-galactopyranoside To a solution of diol 11 (0.050 g, 0.087 mmol) in DMF (3.9 mL) was added sulfur trioxide trimethylamine complex (SO$_3$.TMA) (0.305 g, 2.17 mmol). The reaction mixture was stirred at 50° C. overnight and then cooled to room temperature. The product was purified on Sephadex LH-20 (50% MeOH:CH$_2$Cl$_2$), followed by silica gel chromatography (5%→20% MeOH:CH$_2$Cl$_2$) to afford a sulfated disaccharide (0.053 g, 82%) as a white solid. $R_f$=0.20 (20% MeOH:CH$_2$Cl$_2$). $^1$H NMR (400 MHz, D$_2$O): δ 5.43-5.39 (m, 1H, H-3), 5.27 (t, J=9.9 Hz, 1H, H-4), 5.02-5.00 (m, 2H, H-1, H-2), 4.89 (bs, 1H, H-4'), 4.78 (d, J=8.6 Hz, 1H, H-1'), 4.46 (dd, J=4.0, J=2.4 Hz, 2H, CH$_2$—C≡C), 4.42 (d, J=9.9 Hz, 1H, H-5), 4.32 (dd, J=11.5, J=3.4 Hz, 1H, H-6'), 4.26-4.21 (m, 1H, H-6'), 4.11-4.01 (m, 3H, H-2', H-3', H-5'), 3.80 (s, 3H, OCH$_3$), 2.85 (bs, 1H, C≡CH), 2.11 (s, 3H, NHC(O)CH$_3$), 2.10 (s, 6H, C(O)CH$_3$, C(O)CH$_3$), 2.07 (s, 3H, C(O)CH$_3$); $^{13}$C NMR (100 MHz, D$_2$O): δ 174.45, 173.01, 172.70, 172.43, 169.34, 100.59, 100.00, 99.27, 78.72, 78.70, 76.34, 76.29, 75.73, 72.52, 72.39, 71.44, 71.32, 69.43, 67.67, 56.91, 53.50, 51.09, 22.23, 20.15, 20.00, 19.92; ESI MS: m/z calcd for [C$_{24}$H$_{33}$NO$_{21}$S$_2$-H]$^-$: 734.0908, obsd 734.0903. The $^1$H NMR spectrum of the sulfated disaccharide is shown in FIG. 9, and its $^{13}$C NMR spectrum is shown in FIG. 10.

2-Propargyl O-(sodium-β-D-glucopyranosyluronate)-(1→3)-4,6-di-O-sodium sulfonato-2-deoxy-2-acetamido-β-D-galacto pyranoside 13

Figure 11:
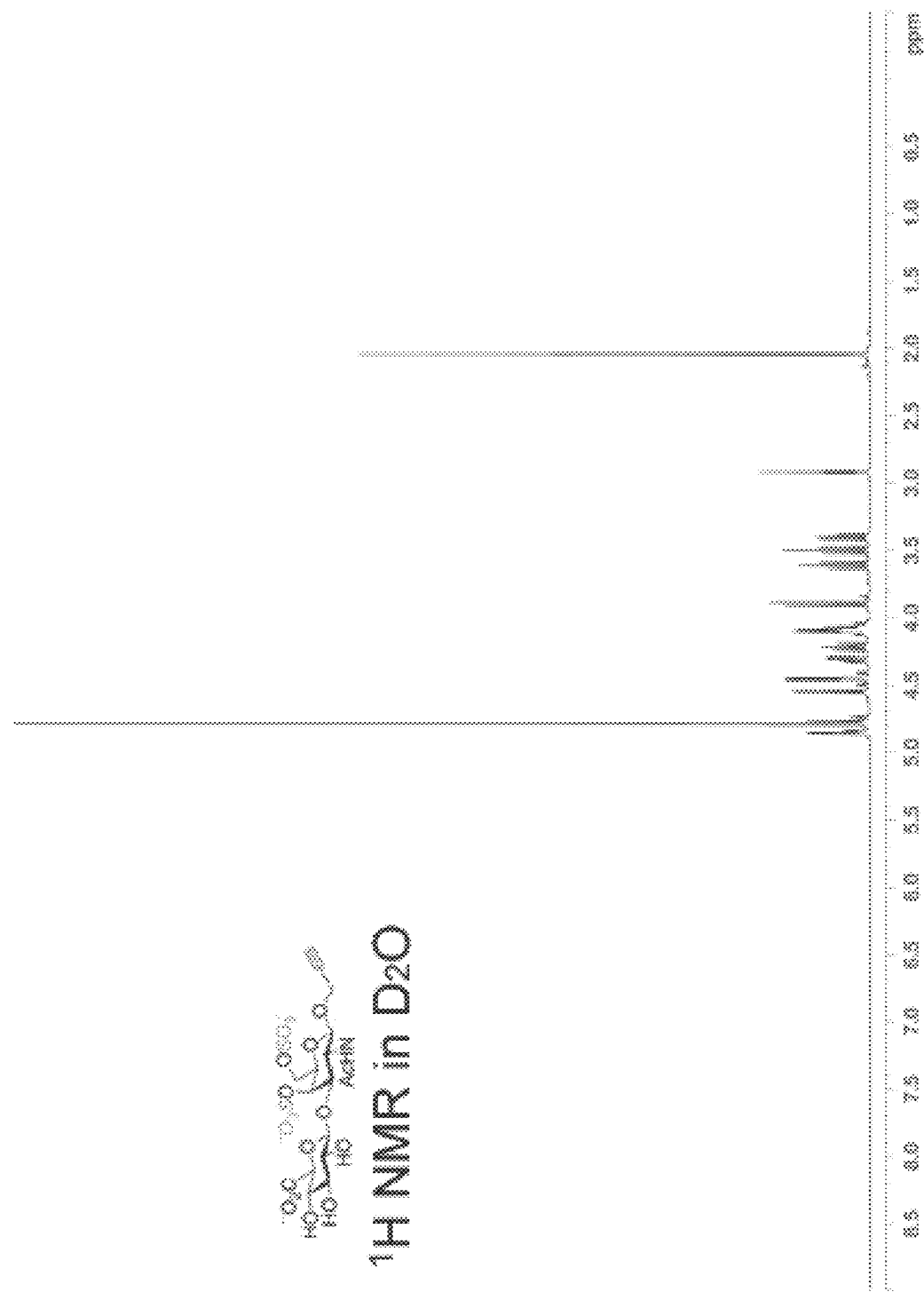
FIG. 11 shows the $^1$H NMR spectra of the desired CS-E disaccharide 13 after sequential treatment of LiOOH and NaOH in one embodiment of the method of synthesizing the glycopeptide as defined above as depicted in the schematic of FIG. 30.
Figure 12:
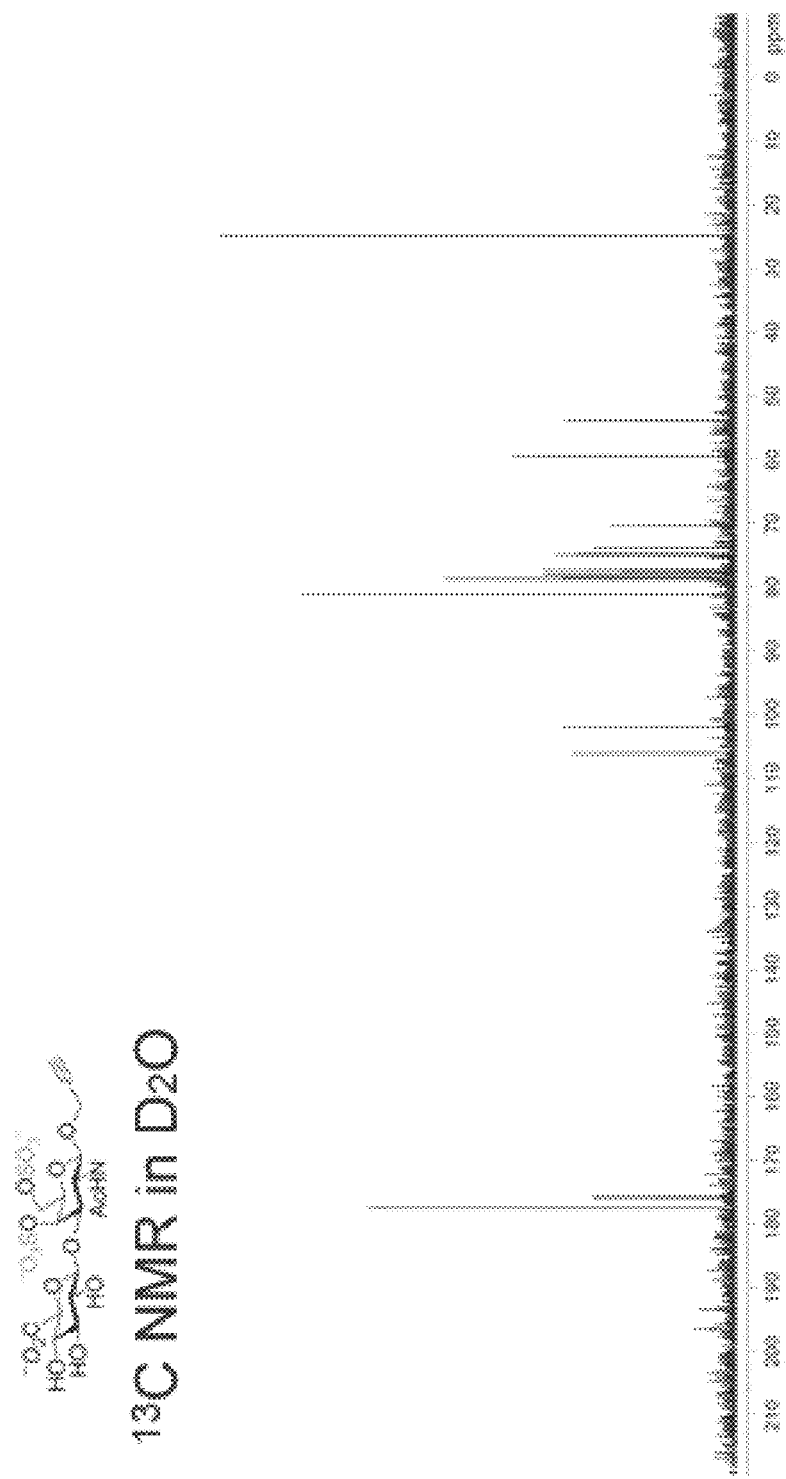
FIG. 12 shows the $^{13}$C NMR spectra of the desired CS-E disaccharide 13 after sequential treat of LiOOH and NaOH in one embodiment of the method of synthesizing the glycopeptide as defined above as depicted in the schematic of FIG. 30.

The sulfated compound (185 mg, 0.251 mmol) was dissolved in THF (684 μL) and H$_2$O (338 μL) and cooled to 0° C. To this were added 1 M aq. LiOH (270 μL) and 30% H$_2$O$_2$ (135 μL). The reaction was stirred at 0° C. for 1 hr and at room temperature for 12 hr. At this time, 4 M aq. NaOH (203 μL) and MeOH (1008 μL) were added and the reaction was stirred for another 12 hr. It was then neutralized with Amberlyst IR-120 resin, filtered, and lyophilized to afford an orange solid. The product was purified by Sephadex G-15 (100% H$_2$O) and lyophilized to afford 13 as a white solid (136 mg, 91%). $^1$H NMR (400 MHz, D$_2$O): δ 4.86 (d, J=2.4 Hz, 1H, H-4'), 4.78 (d, J=9.0 Hz, 1H, H-1'), 4.70 (d, J=7.8 Hz, 1H, H-1), 4.45 (dd, J=4.1, J=2.4 Hz, 2H, CH$_2$—C≡C), 4.31 (dd, J=11.4, J=3.3 Hz, 1H, H-6'), 4.24-4.19 (m, 1H, H-6'), 4.13-4.04 (m, 3H, H-2', H-3', H-5'), 3.90 (d, J=9.8 Hz, 1H, H-5), 3.61 (t, J=9.1 Hz, 1H, H-4), 3.50 (t, J=9.3 Hz, 1H, H-3), 3.40 (dd, J=9.4, J=7.8 Hz, 1H, H-2), 2.92 (t, J=2.4 Hz, 1H, C≡CH), 2.04 (s, 3H, NHC(O) CH$_3$); $^{13}$C NMR (100 MHz, D$_2$O): δ 177.46, 175.82, 106.10, 101.93, 81.26, 78.75, 78.60, 78.07, 77.57, 77.44, 74.95, 74.83, 73.81, 70.30, 59.45, 53.93, 24.81; ESI MS: m/z calcd for [C$_{17}$H$_{25}$NO$_{18}$S$_2$-H]$^-$: 594.0435, obsd 594.0429. The $^1$H NMR spectrum of 13 is shown in FIG. 11, and its $^{13}$C NMR spectrum is shown in FIG. 12.

General Procedure for Solution Phase Peptide Synthesis:

In a typical solution phase peptide synthesis, Boc-Peptide (1)-OH (1.0 equiv.) was dissolved in DMF (final concentration was adjusted to 0.1M). H-Peptide(2)-OCH$_3$ (1.1 equiv.), TBTU (1.1 equiv.), and DIPEA (5.0 equiv.) were then added to the solution. The reaction mixture was stirred at room temperature until the reaction completed. After the completion, the solvent removed in vacuo to afford a yellow solid. Purification of this solid by either flash column chromatography on silica or reverse phase HPLC afforded Boc-Peptide(1)-Peptide(2)-OCH$_3$.

General Method for Boc Group Deprotection of Boc-Peptide (1)-Peptide (2)-OCH$_3$ Boc-Peptide(1)-Peptide(2)-OCH$_3$ was dissolved in CH$_2$Cl$_2$/TFA (1:1) at 0° C., and stirred for 2 hrs. After the completion, the solvent was removed by blowing a slow stream of nitrogen gas and then diethyl ether was added to give H-Peptide(1)-Peptide(2)-OCH$_3$ quantitatively as a white precipitate.

General Procedure for Methyl Group Deprotection of Boc-Peptide(1)-Peptide (2)-OCH$_3$:

To a solution of Boc-Peptide(1)-Peptide(2)-OCH$_3$ (1.0 equiv.) in THF/MeOH (1:1, final concentration was adjusted to 0.05M) was added aq. NaOH (2.0 equiv.) and sonicated for 5 min. At this time, the same volume of CH$_2$Cl$_2$ was added and the reaction was stirred for additional 2 hrs. It was then neutralized with Amberlyst IR-120 resin, filtered, and evaporated in vacuo to afford H-Peptide(1)-Peptide(2)-OCH$_3$ quantitatively.

Figure 13:
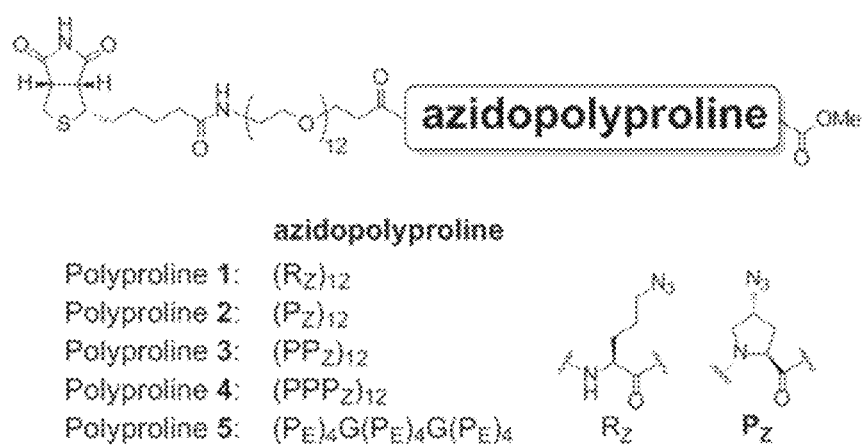
FIG. 13 shows the general structure of biotin-$PEG_{12}$-azidopolyproline-$OCH_3$, and formulae for exemplary polyprolines 1 to 5.
Figure 14:
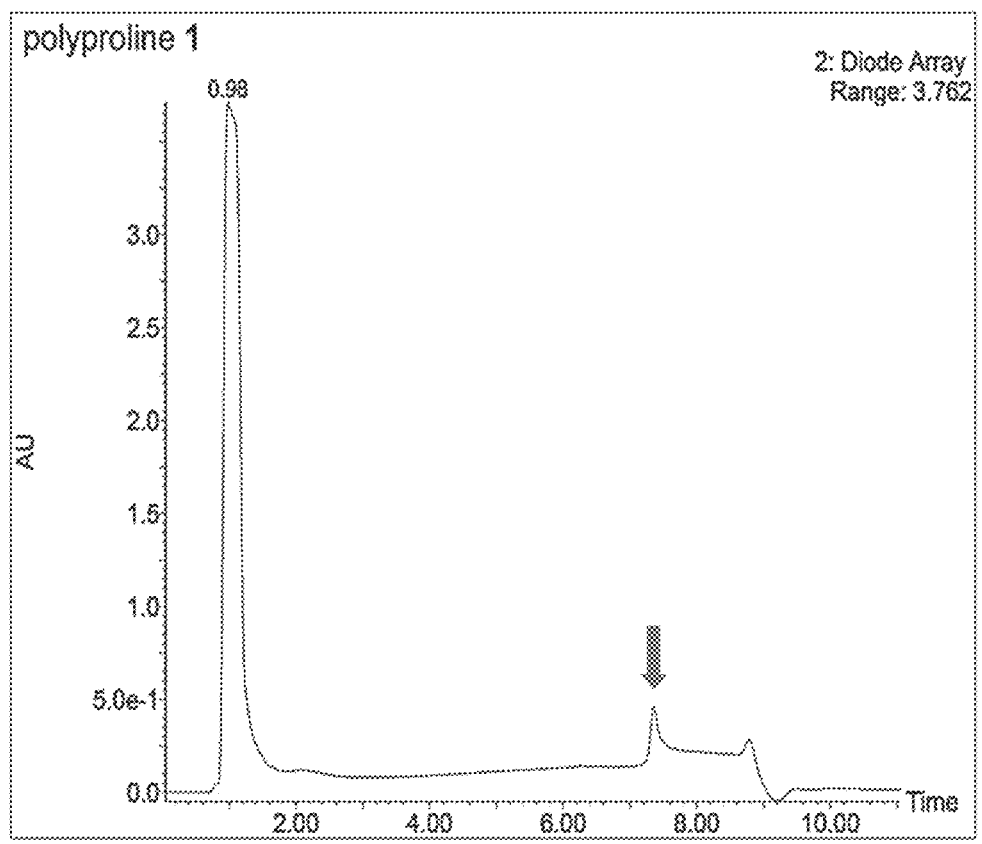
FIG. 14 shows the analytical HPLC traces (top) and ESI mass data (bottom) of polyproline 1.
Figure 14:
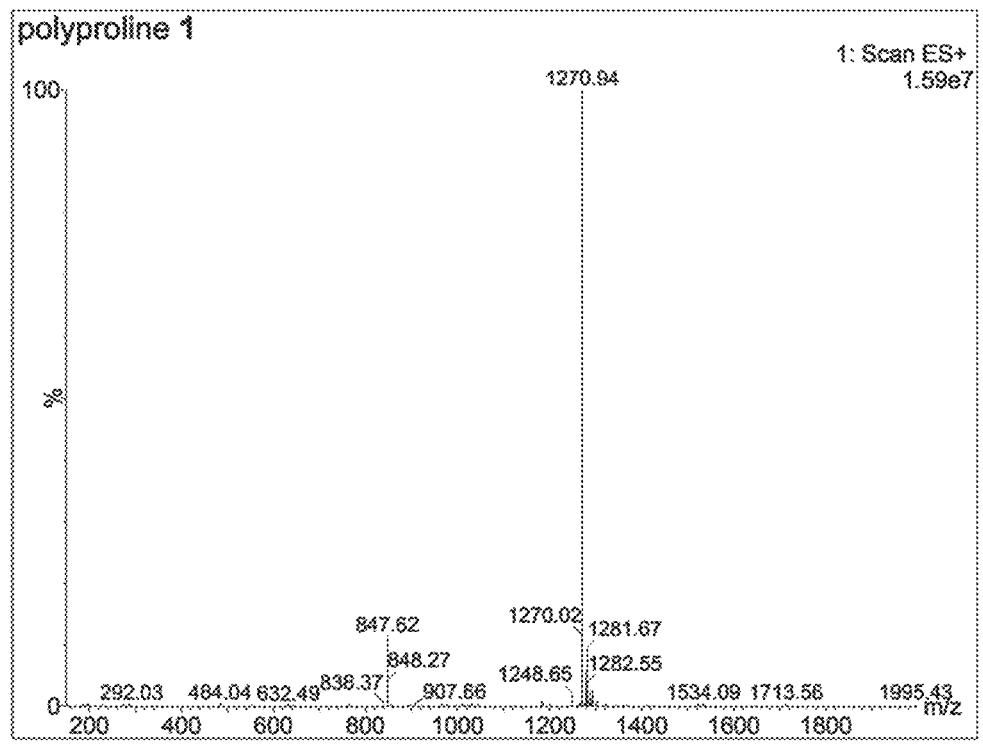
Figure 15:
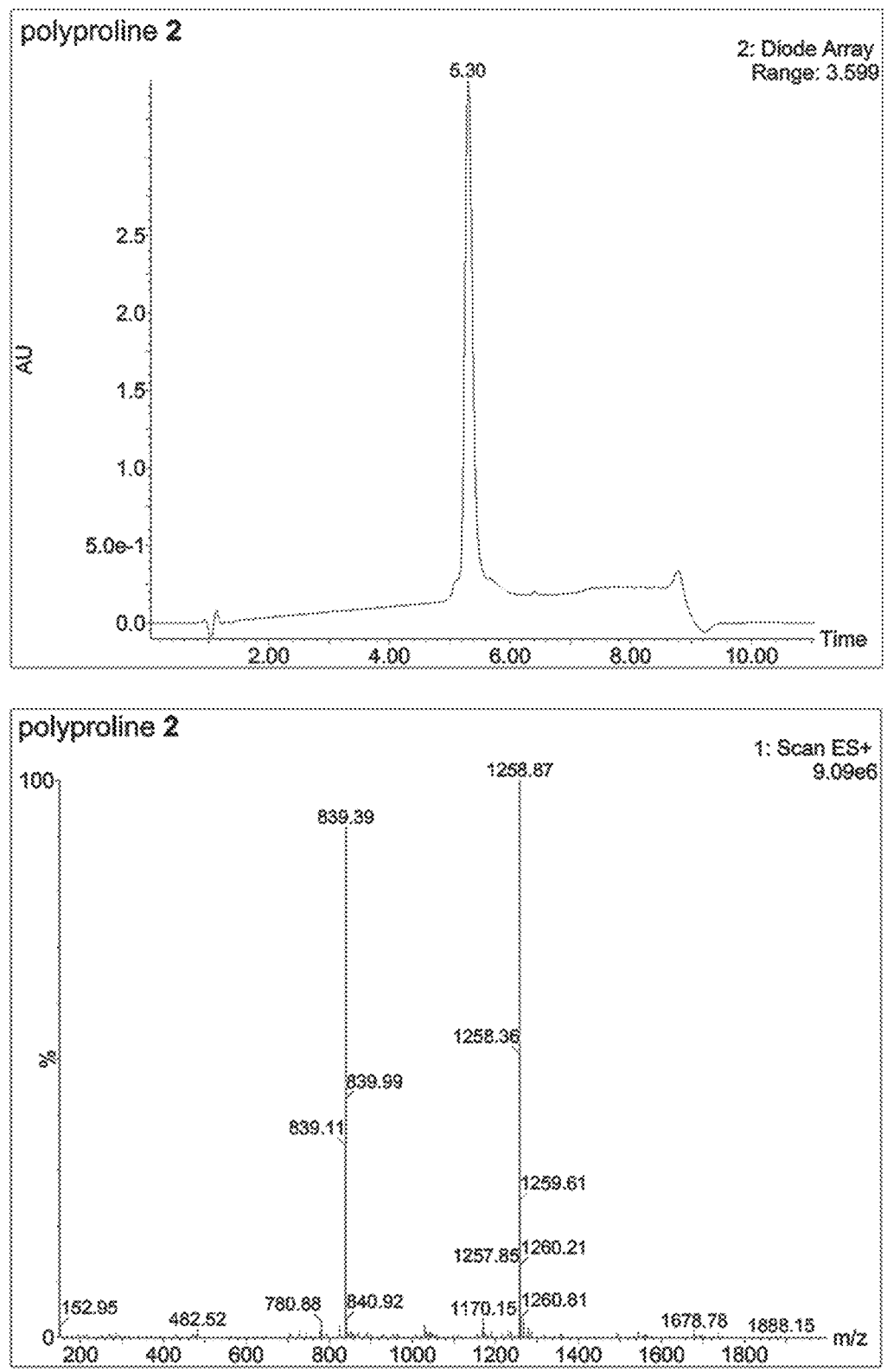
FIG. 15 shows the analytical HPLC traces (top) and ESI mass data (bottom) of polyproline 2.
Figure 16:
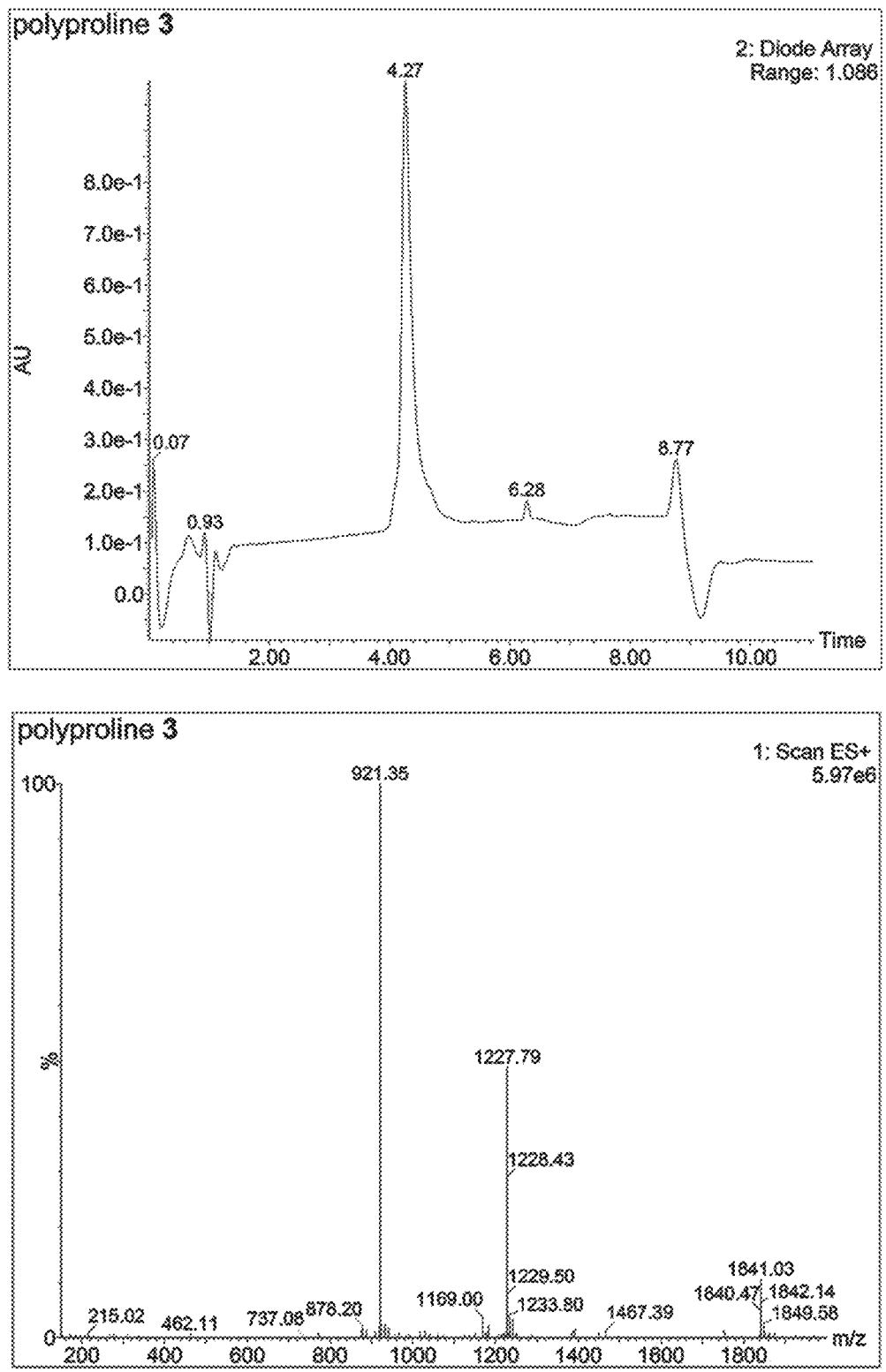
FIG. 16 shows the analytical HPLC trace (top) and ESI mass data (bottom) of polyproline 3.
Figure 17:
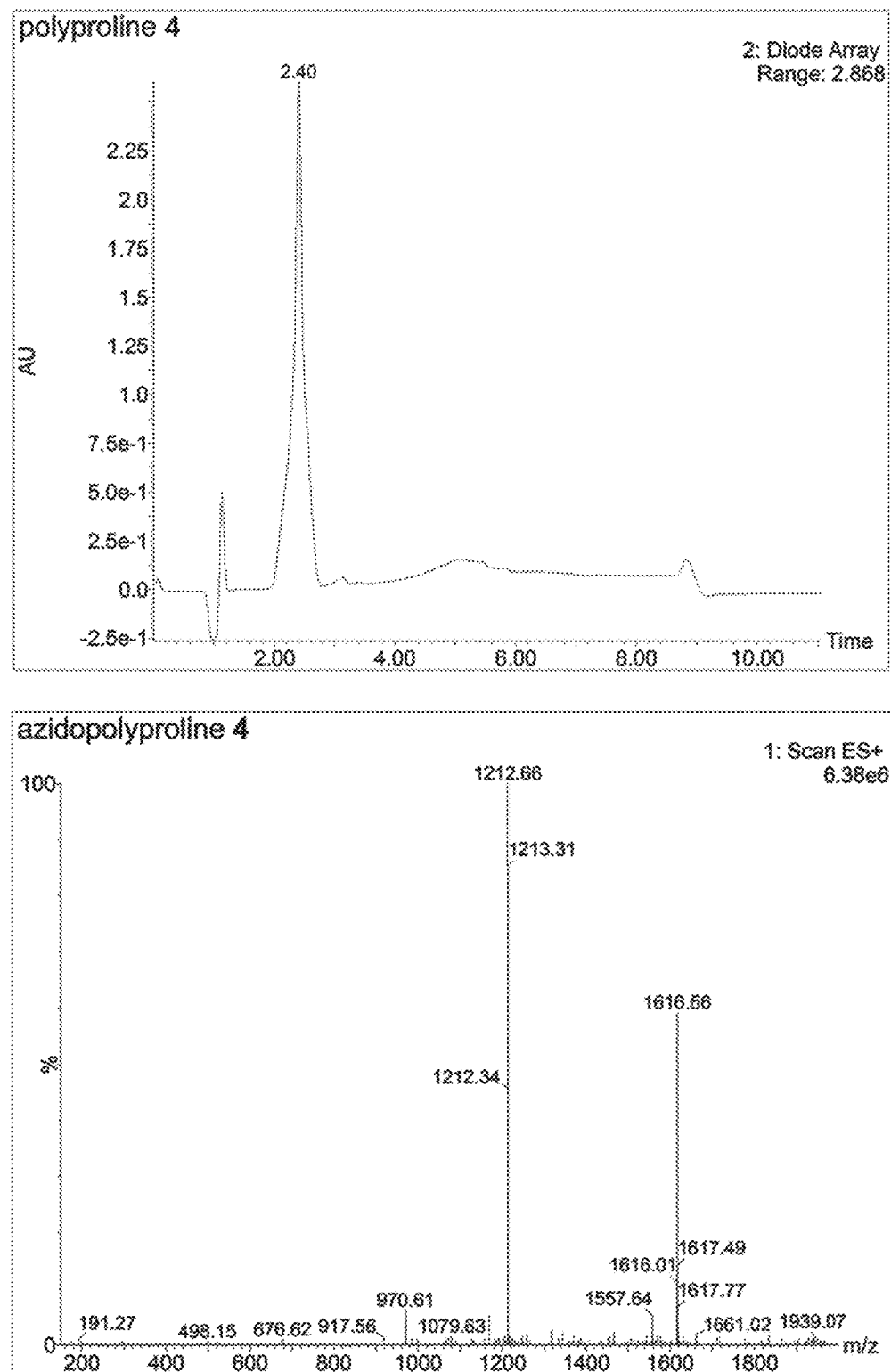
FIG. 17 shows the analytical HPLC traces (top) and ESI mass data (bottom) of polyproline 4.
Figure 18:
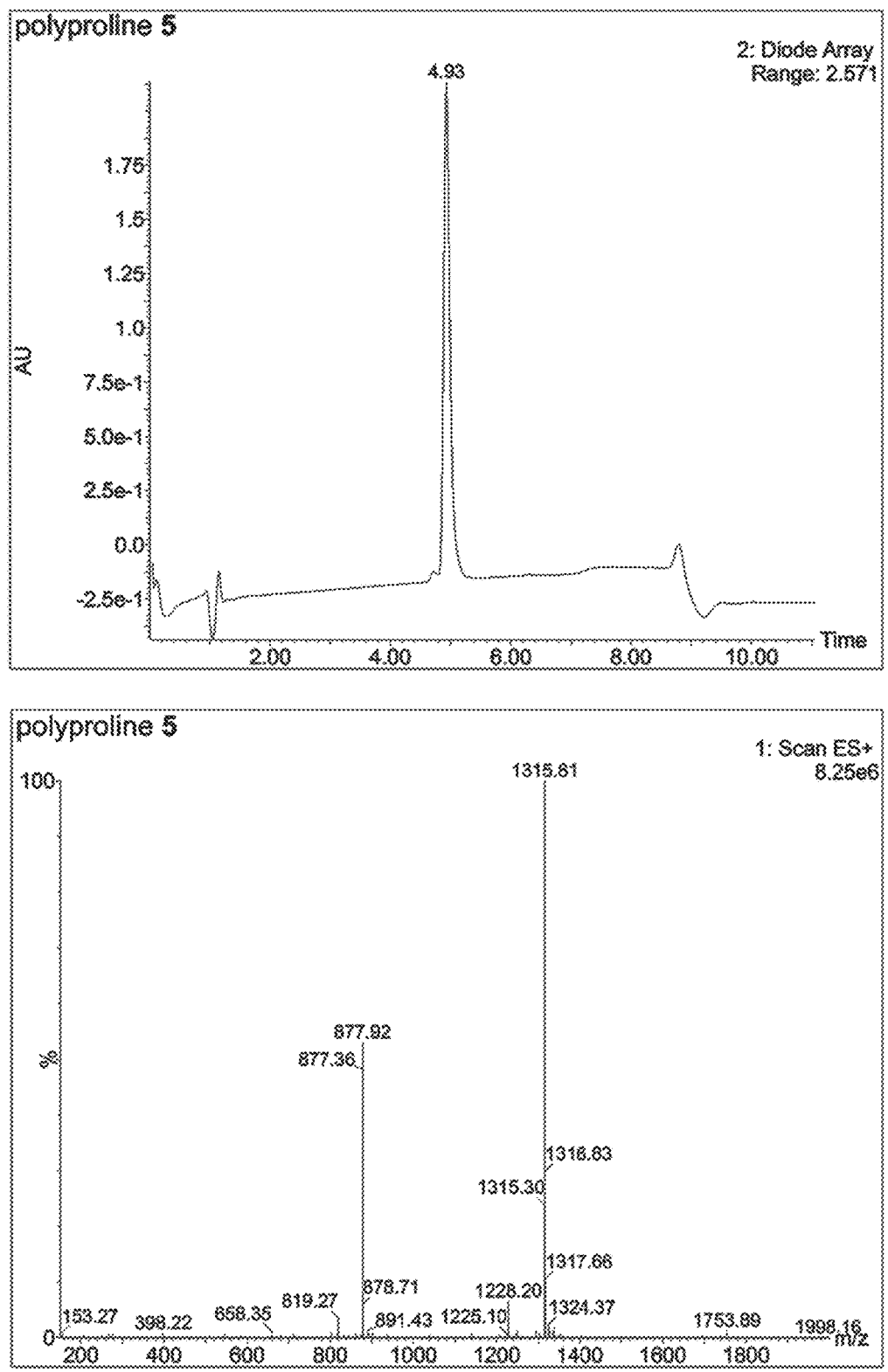
FIG. 18 shows the analytical HPLC traces (top) and ESI mass data (bottom) of polyproline 5.

General Procedure for the Synthesis of Biotin-PEG$_{12}$-Azidopolyproline-OCH$_3$:

To a solution of H-Azidopolyproline-OCH$_3$ (1.0 equiv.) in DMSO (final concentration was adjusted to 0.1M) were added EZ-link NHS-PEG$_{12}$-Biotin (1.2 equiv., from Thermo Scientific) and DIPEA (5.0 equiv.), and stirred overnight at room temperature. After the completion, the solvent was removed in vacuo to afford a yellow sticky solid. Purification of this solid by reverse phase HPLC afforded biotin-PEG$_{12}$-azidopolyproline-OCH$_3$. The structures of the biotin-PEG$_{12}$-azidopolyproline-OCH$_3$ are shown in FIG. 13. The analytical HPLC conditions for biotin-PEG$_{12}$-azidopolyproline-OCH$_3$ are set out below in Table 1, while the ESI-MS data of biotin-PEG$_{12}$-azidopolyproline-OCH$_3$ are set out below in Table 2. The analytical HPLC traces and ESI mass data of polyprolines 1 to 5 are shown FIGS. 14 to 18, respectively.

TABLE 1

Analytical HPLC conditions for biotin-PEG$_{12}$-azidopolyproline-OCH$_3$.

| Biotin-PEG$_{12}$-azido poliproline-OCH$_3$ | HPLC condition* | Retention time |
| --- | --- | --- |
| Polyproline 1 | 5-60% A over 8 min | 7.35 min |
| Polyproline 2 | 5-60% A over 8 min | 5.30 min |
| Polyproline 3 | 5-60% A over 8 min | 4.27 min |
| Polyproline 4 | 5-60% A over 8 min | 2.40 min |
| Polyproline 5 | 5-60% A over 8 min | 4.93 min |

*A: CH$_3$CN/0.1% TFA, B: H$_2$O/0.1% TFA.

TABLE 2

ESI-MS Data of biotin-PEG$_{12}$-azidopolyproline-OCH$_3$.

| Biotin-PEG$_{12}$-azido poliproline-OCH$_3$ | MS, calculated | ESI-MS, observed |
| --- | --- | --- |
| Polyproline 1 | 2538.29 | 1270.94 ([M + 2H]$^{2+}$), 847.62 ([M + 3H]$^{3+}$) |
| Polyproline 2 | 2514.11 | 1258.87 ([M + 2H]$^{2+}$), 839.39 ([M + 3H]$^{3+}$) |
| Polyproline 3 | 3678.74 | 1841.03 ([M + 2H]$^{2+}$), 1227.79 ([M + 3H]$^{3+}$), 921.35 ([M + 4H]$^{4+}$) |
| Polyproline 4 | 4843.37 | 1616.56 ([M + 3H]$^{3+}$), 1212.66 ([M + 4H]$^{4+}$) |
| Polyproline 5 | 2628.15 | 1315.81 ([M + 2H]$^{2+}$), 877.92 ([M + 3H]$^{3+}$) |

General Procedure for the Synthesis of Glycopeptides Via Click Reaction:

In a typical click reaction, a small vial was charged with alkyne-functionalized CS disaccharides (total 15.6 equiv., 1.3 equiv. per azide), biotin-PEG$_{12}$-azidopolyproline-OMe (1.0 equiv.), Tris[(1-benzyl-1H-1,2,3-triazol-4-yl)methyl] amine (TBTA, 0.3 equiv. per azide), and a small stir bar under argon atmosphere. The mixture was dissolved in degassed DMSO, and the desired amount of copper (I) iodide (0.3 mol % per azide) stock solution in DMSO and DIPEA (48 equiv.) were added. The reaction mixture was then stirred at room temperature for 7 days. The consumption of biotin-PEG$_{12}$-azidopolyproline-OCH$_3$ was monitored by analytical reverse phase HPLC equipped with C-18 column. After the completion, anhydrous THF/MeOH (9:1) was added to give a white precipitate (TBTA and DIPEA can be removed as the glycopeptides and excess CS-disaccharides are insoluble at this condition). The white precipitate was dissolved in 200 μL of 6M aq. NaCl and purified by Sephadex G-15 column (100% H$_2$O) to afford desired glycopeptides as white solids upon lyophilization.

Figure 19:
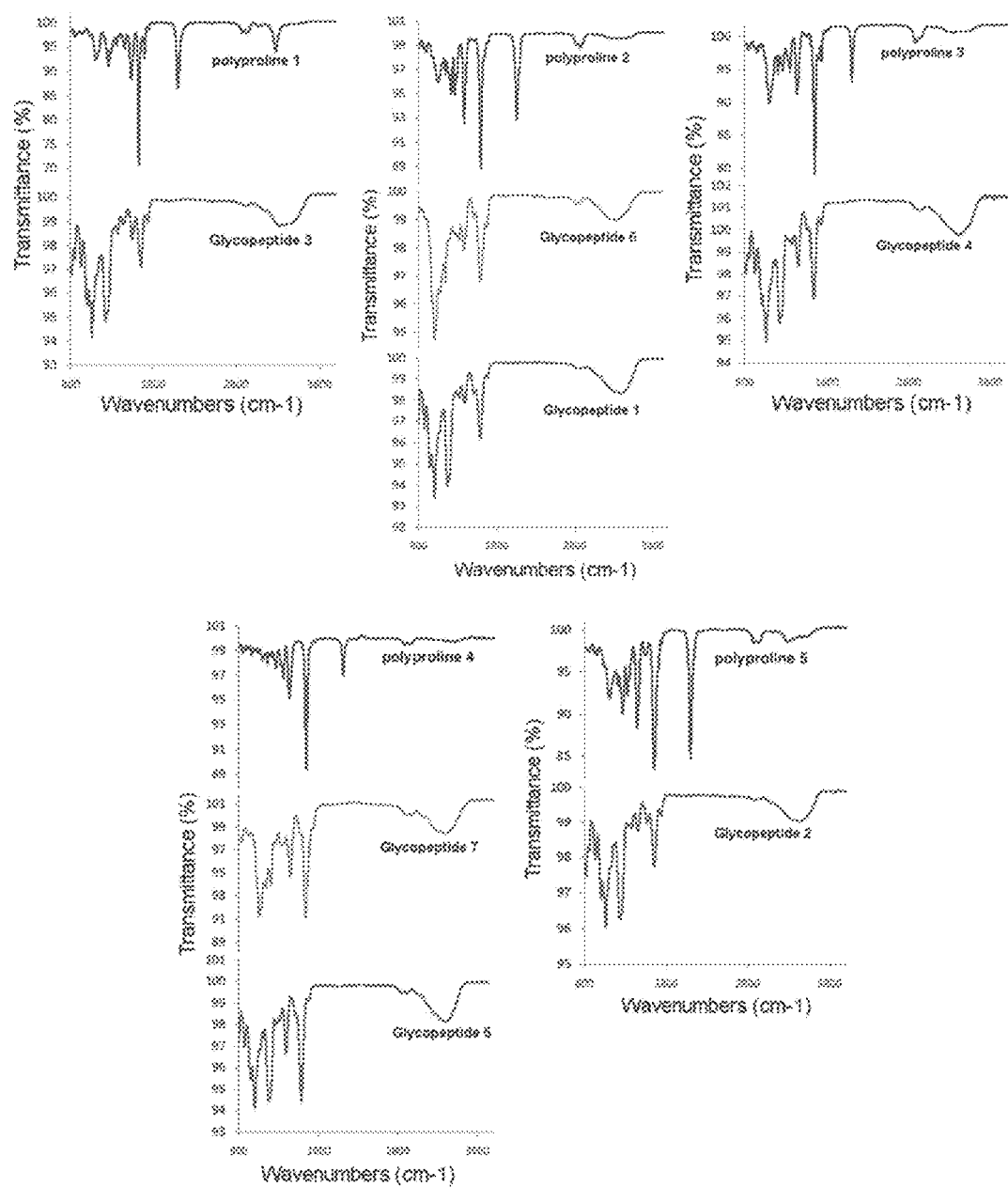
FIG. 19 shows the FT-IR spectra of exemplary polyprolines 1 to 5 and glycopeptides 1 to 7. The disappearance of the azide band in the spectra of the glycopeptides indicates completion of coupling of the CS-disaccharides to the polyproline backbone.
Figure 20:
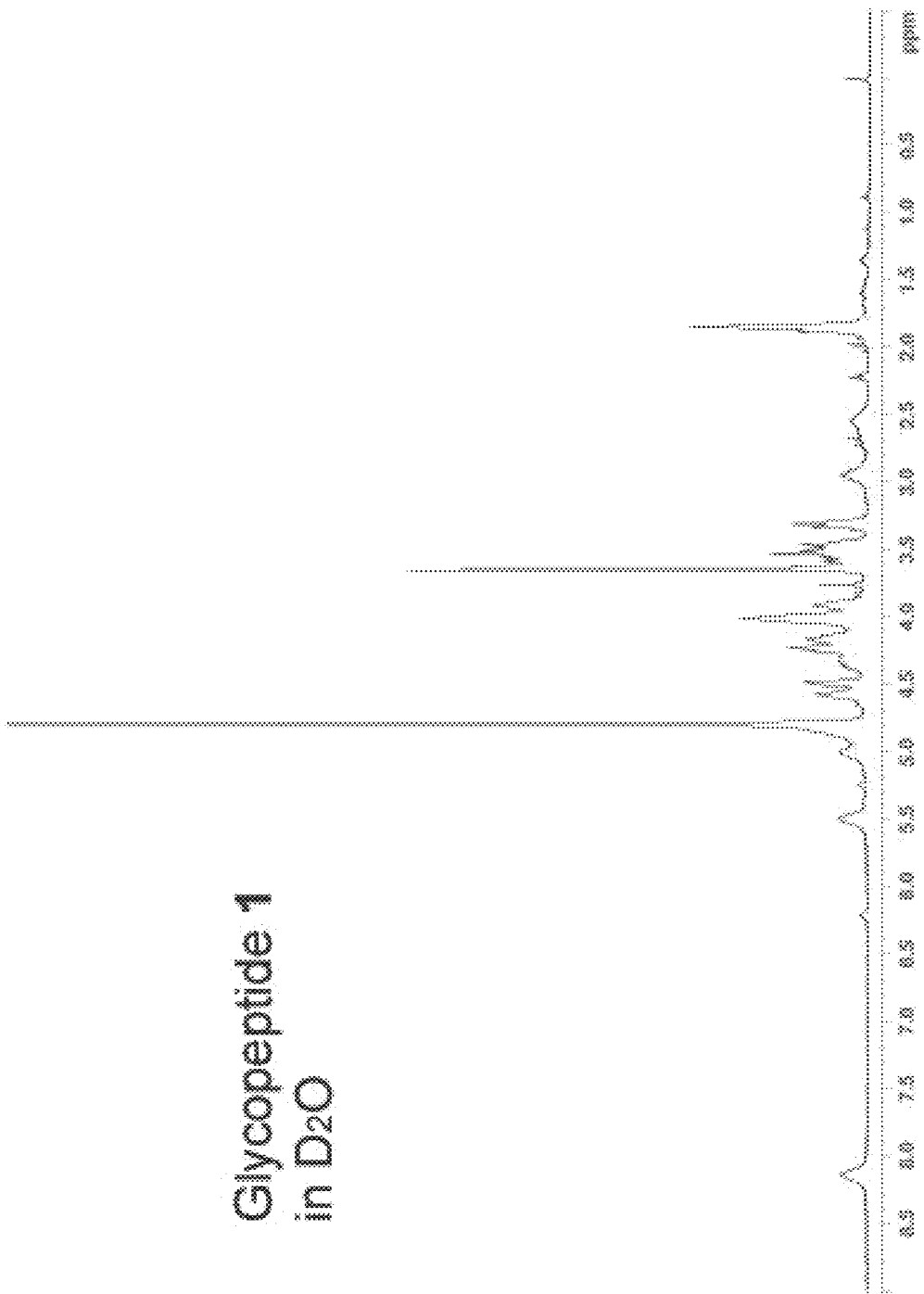
FIG. 20 shows the $^1$H NMR spectrum of glycopeptide 1.
Figure 21:
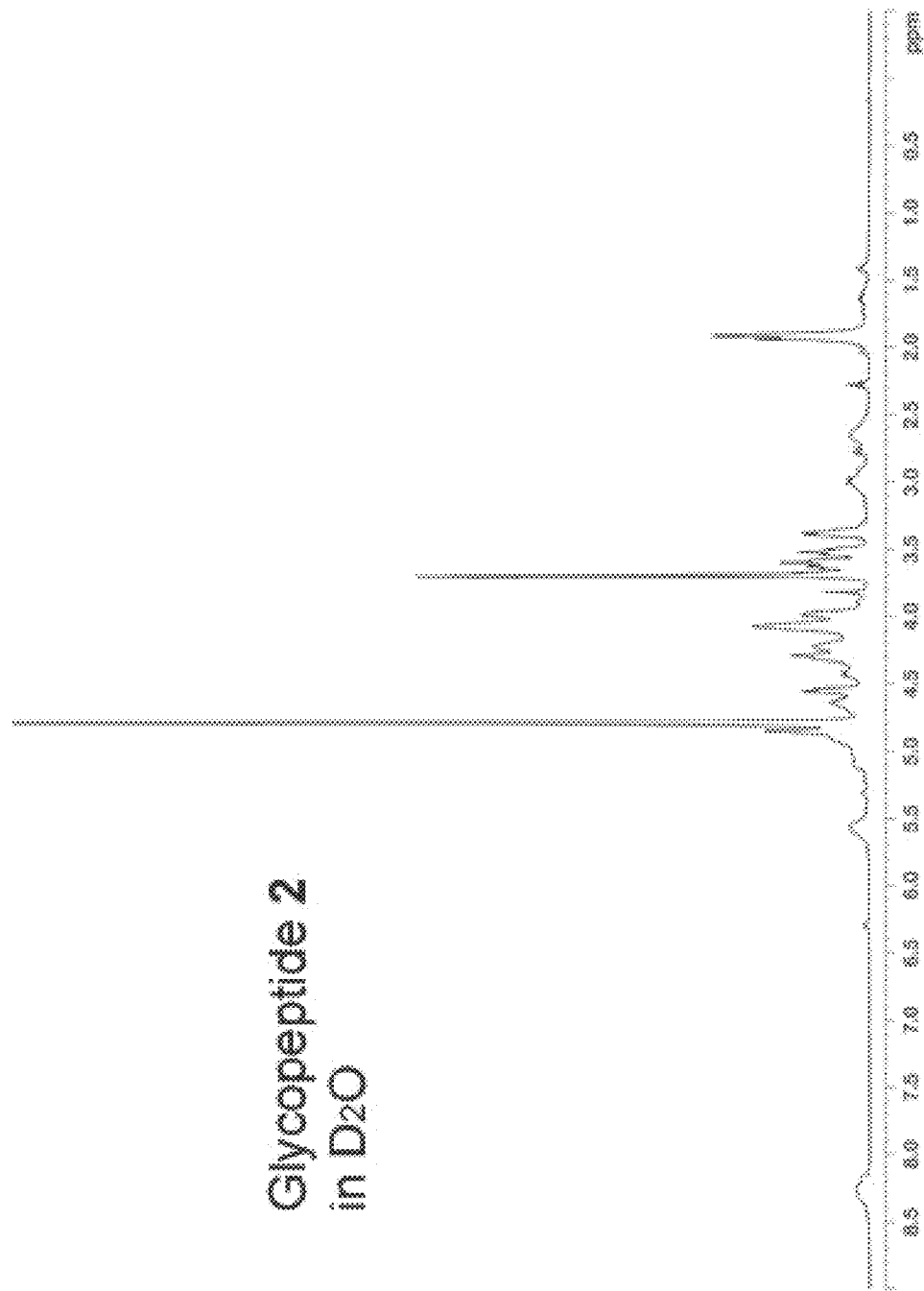
FIG. 21 shows the $^1$H NMR spectrum of glycopeptide 2.
Figure 22:
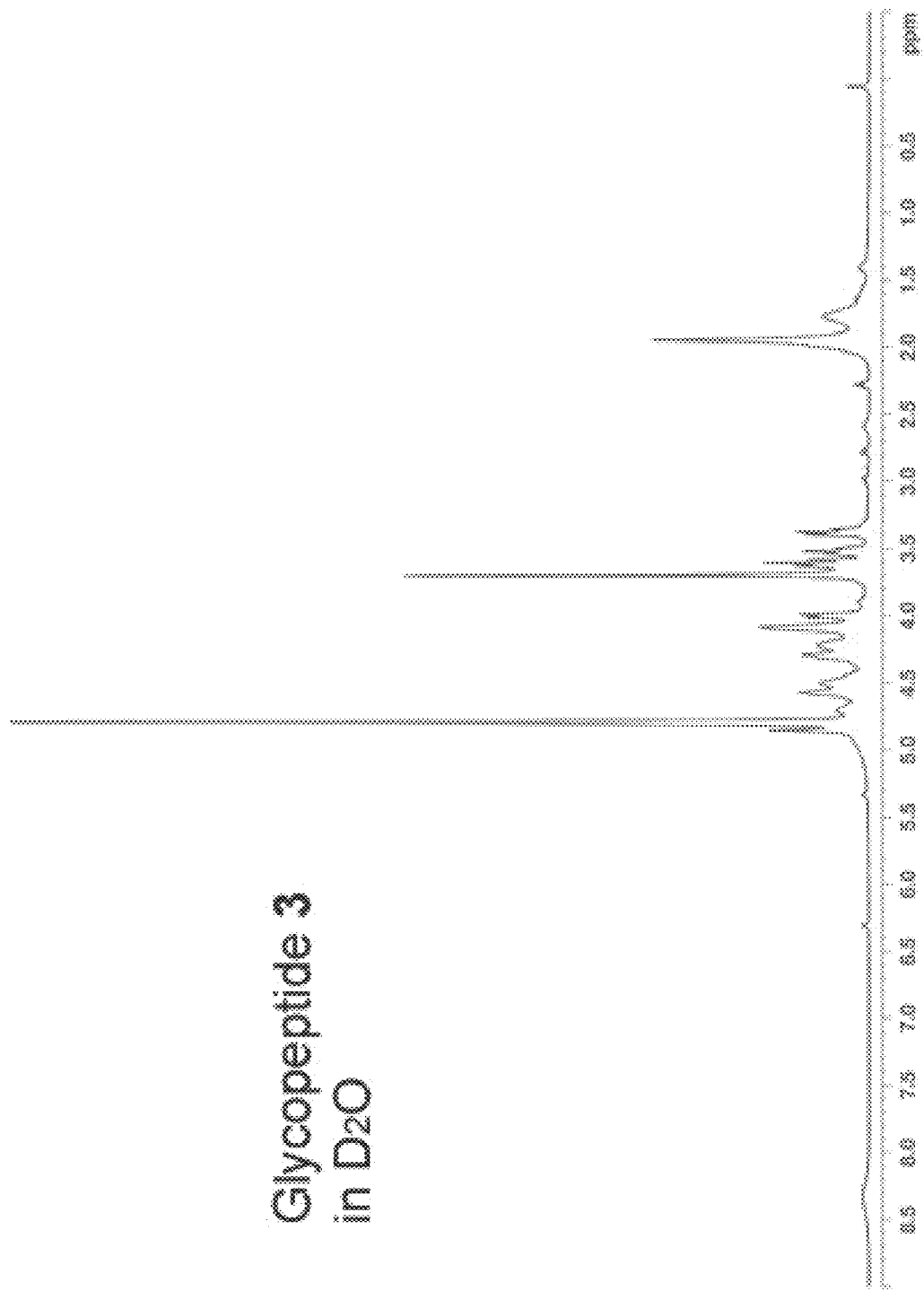
FIG. 22 shows the $^1$H NMR spectrum of glycopeptide 3.
Figure 23:
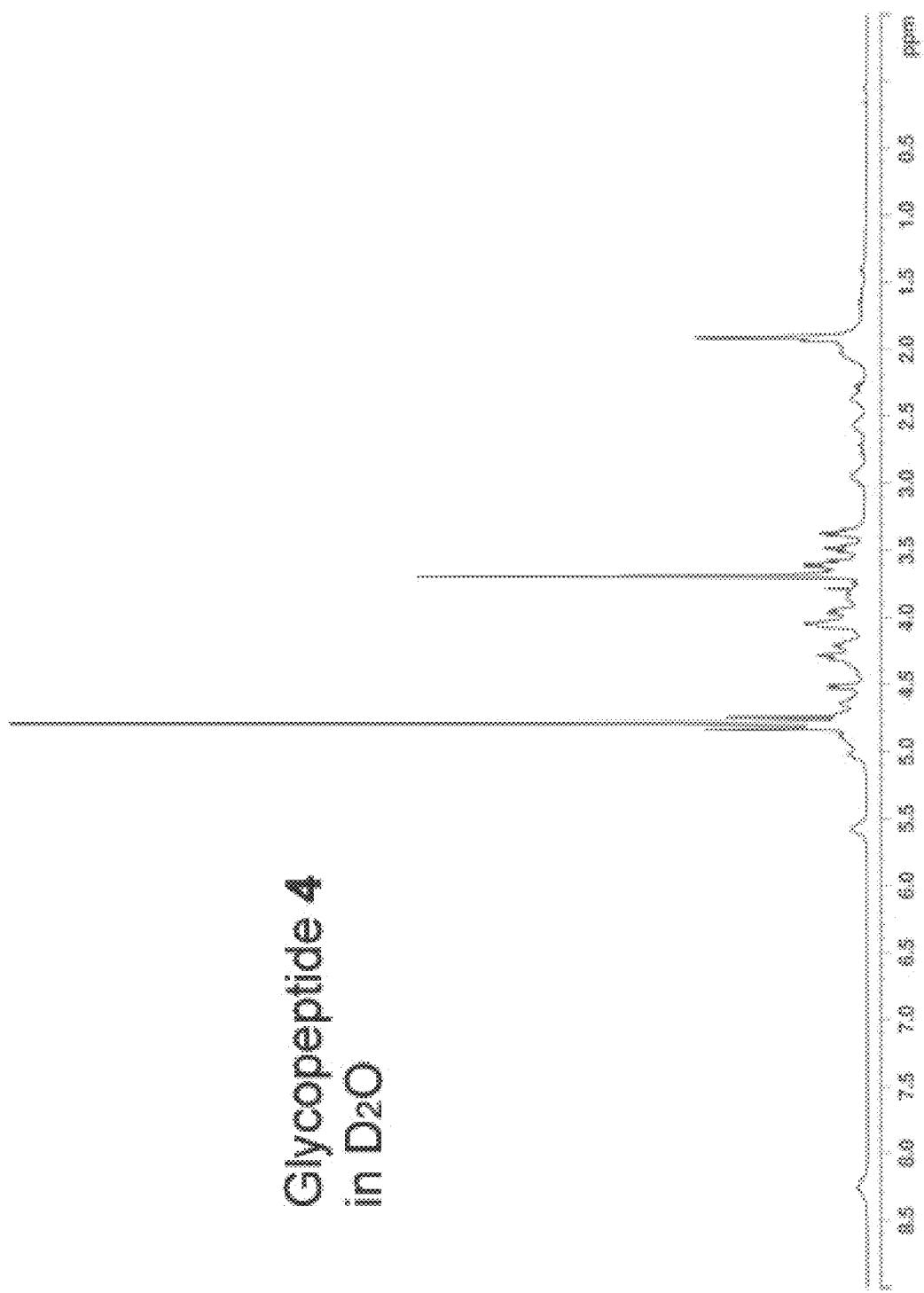
FIG. 23 shows the $^1$H NMR spectrum of glycopeptide 4.
Figure 24:
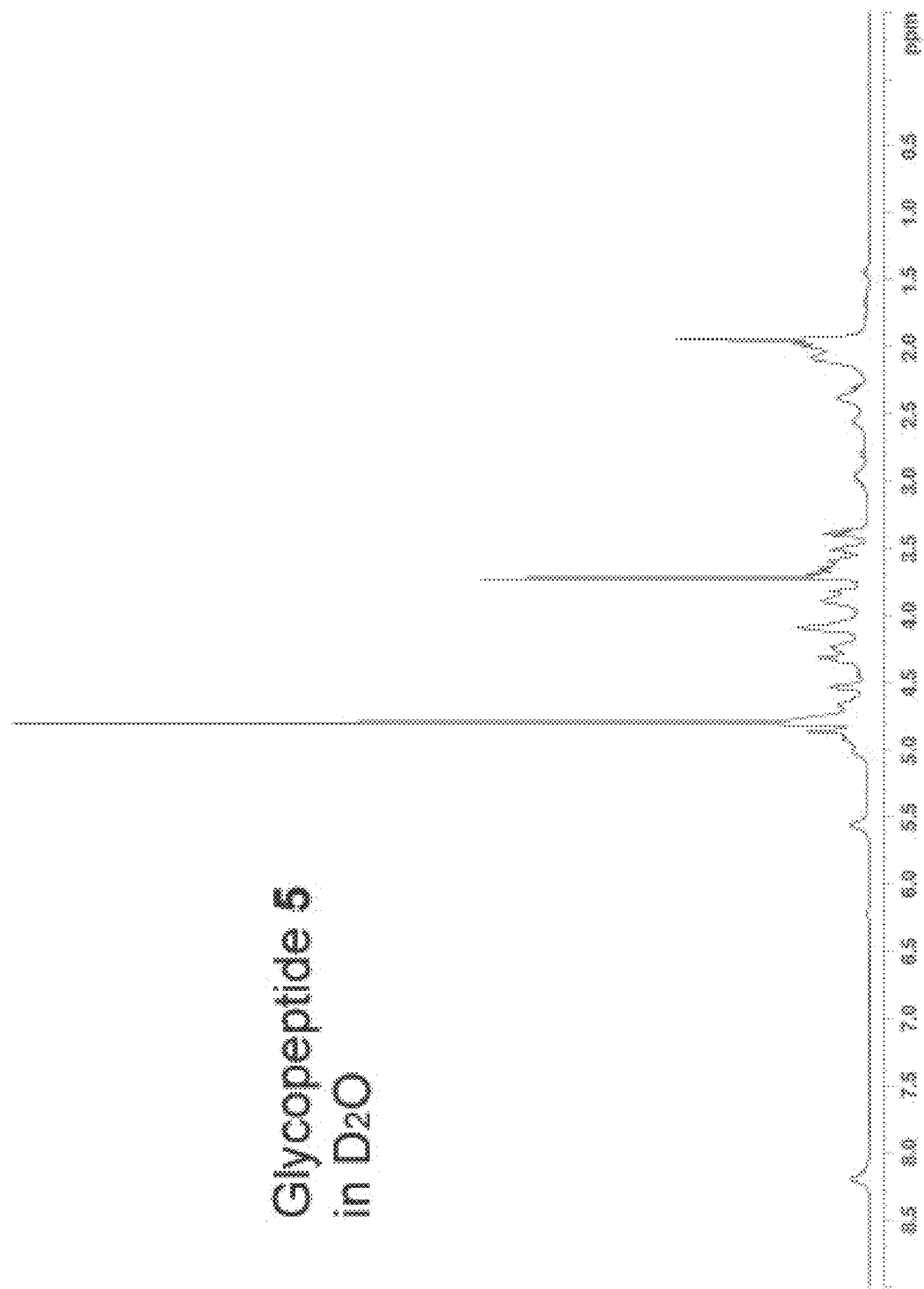
FIG. 24 shows the $^1$H NMR spectrum of glycopeptide 5.
Figure 25:
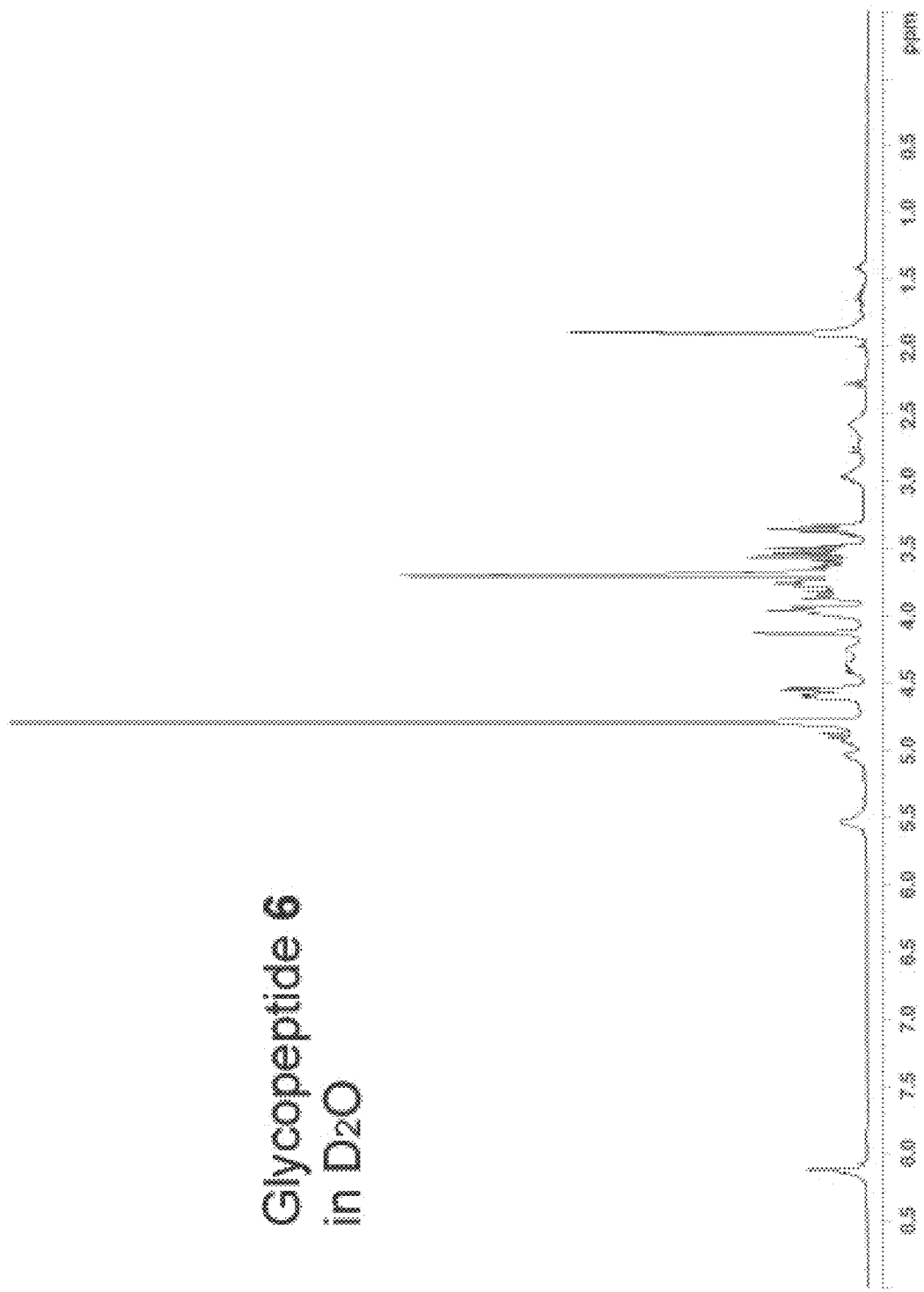
FIG. 25 shows the $^1$H NMR spectrum of glycopeptide 6.
Figure 26:
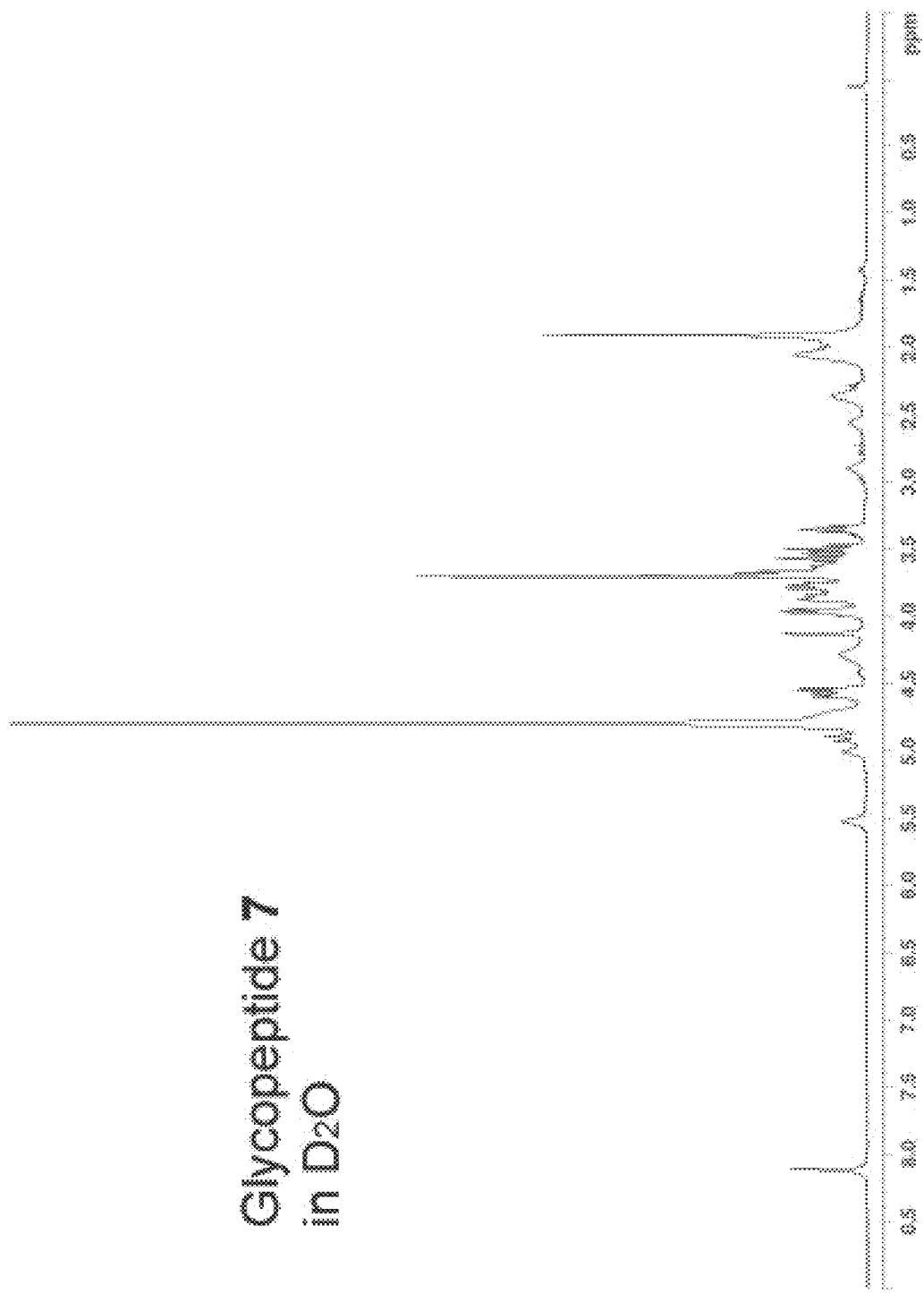
FIG. 26 shows the $^1$H NMR spectrum of glycopeptide 7.

FTIR was used to monitor the azide vibrational band (~2100 cm$^{-1}$) for the completion of the click coupling reaction. Fourier transform infrared spectroscopy (FTIR) was carried out using a Perkin Elmer FTIR Spectrum 100 between 4000 and 800 cm$^{-1}$ at a spectral resolution of 4 cm$^{-1}$, and the number of scans was 4. Samples were placed on a germanium stage and pressed before every measurement. The disappearance of the azide band in the spectra of the glycopeptides indicated the completion of the coupling reactions (FIG. 19). The $^1$H NMR spectra of glycopeptides 1 to 7 are shown in FIGS. 20 to 26.

Figure 27:
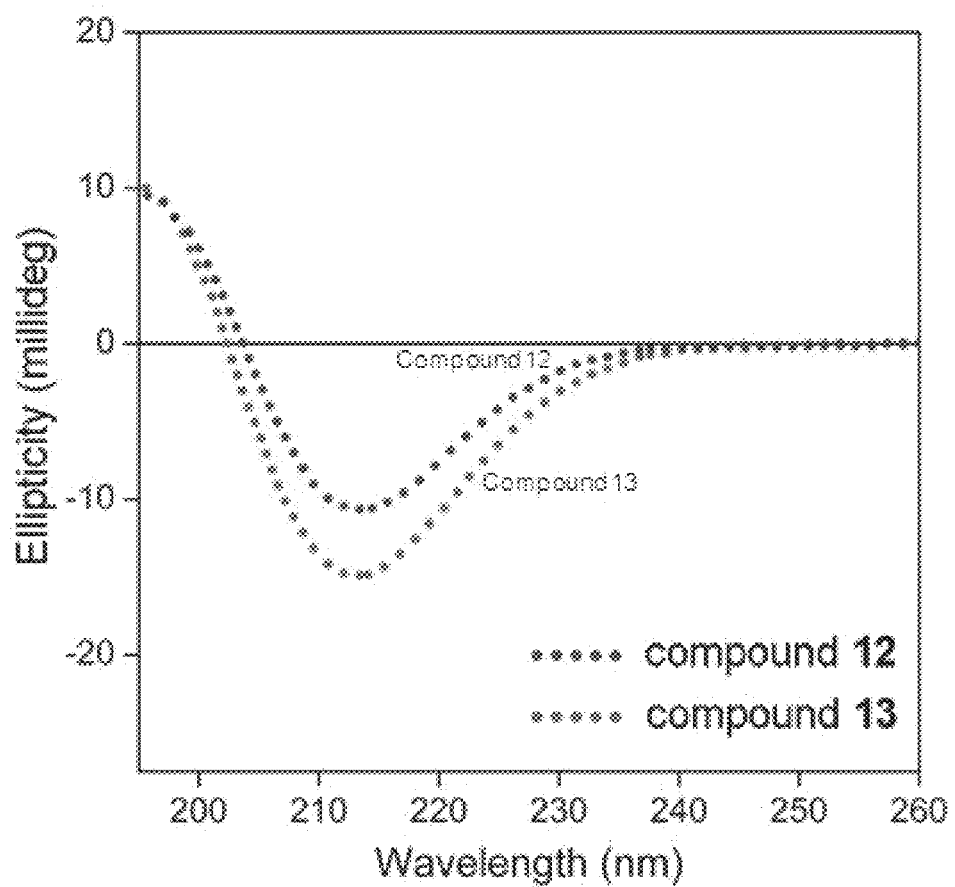
FIG. 27 shows the CD spectra of compounds 12 and 13 (2.4 mM) at 25° C.
Figure 28:
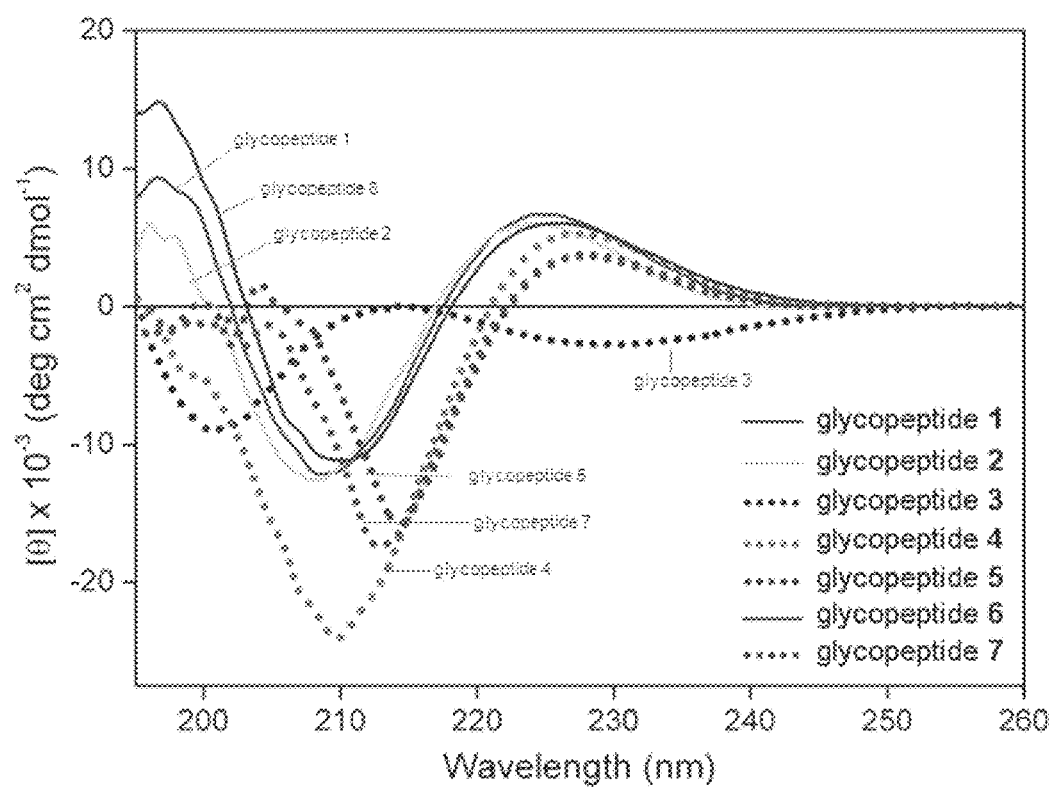
FIG. 28 shows the CD spectra of glycopeptides 1 to 7 (0.2 mM) at 25° C.

Circular Dichroism Analysis:

CD spectra were recorded on an Aviv 410 circular dichroism spectrometer equipped with temperature controller. Glycopeptide solutions at concentrations of 200 μM (2.4 mM for compounds 12 and 13) were used. All sample solutions made in 10 mM sodium phosphate-dibasic buffer, pH 7.0, were equilibrated for 24 hrs at 4° C. and then 1 hr at room temperature before CD measurements. Cells of 1 mm path length were used. Spectra were recorded from 260 to 190 mm at 25° C. Mean residue ellipticity [θ] was calculated as follows;

$$[\theta] = \theta/(10 \cdot N \cdot c \cdot l)$$

θ represents the ellipticity in millidegrees, N the number of amino acid residues, c the molar concentration in mol·L$^{-1}$, and l the cell path length in cm. The CD spectra of compounds 12 and 13 are shown in FIG. 27, while the CD spectra of glycopeptides 1 to 7 are shown in FIG. 28.

Enzyme-Linked Immunosorbent Assay (ELISA):

The new plate was rinsed three times with PBS containing 0.05% Tween 20 and one time with PBS before the experiment. 100 μL of biotinylated glycopeptide solutions (0.5 μM) were added to required wells in the Pierce Streptavidin Coated High Binding Capacity plates (#15501), and incubated overnight at room temperature. After immobilization of glycopeptides, the plates were rinsed three times with PBS containing 0.05% Tween 20 and one time with PBS. The surface was then blocked with 125 μL of 3% BSA in PBS for 1 hr, followed by rinsing three times with PBS containing 0.05% Tween 20 and one time with PBS. 100 μL of varying concentrations (0 nM, 10 nM, 20 nM, 30 nM, 40 nM, 50 nM and 60 nM) of NGF in PBS containing 1% BSA was added to the wells and incubated for 2 hrs at 37° C. The surface was rinsed three times with PBS containing 0.05% Tween 20 and one time with PBS.

Washing was done three times with pH 4.0 10 mM Sodium acetate buffer containing 0.05% Tween 20 and 0.5M NaCl for 10 min. The plate was then rinsed five times with 200 L of PBS 0.05% Tween 20. Following that, the plate was washed one time with 10 mM TBS 0.05% Tween 20 and 0.5M NaCl for 10 min. The wells were rinsed three times with PBS 0.05% Tween 20 and one time with PBS.

The wells were then incubated with anti-NGF labeled with HRP in PBS containing 1% BSA. Absorbance signal was then developed with 100 μL of TMB Substrate from Thermo Scientific Pierce (#0034021) for 20 to 30 min before quenching with 100 μL of 2M H2SO4. Absorbance at 450 nm was then measured.

Surface Plasmon Resonance:

Affinity measurements were performed using a Biacore T100 system (GE Heathcare). The CM5 sensor chip was used for all measurements. At first, the instrument was primed with HBS-EP+ (GE Heathcare) buffer. Then, 700RU of streptavidin was immobilized on all flow cells. A 1:1 mixture of 0.4 M EDC and 0.1 M NHS was used to activate the flow cells, and 0.008 mg/mL streptavidin solution reconstituted in Acetate 5.0 buffer (GE Healthcare) was injected. Blocking of the remaining activated groups was done with a 1 M solution of ethanolamine (pH 8.5). Flow cell 1 (or 3) was used as a reference to subtract nonspecific binding, drift, and the bulk refractive index, while flow cell 2 (or 4) was further immobilized with glycol-peptide samples of varying structures. Biotinylated glycopeptides (20 nM) were dissolved in HBS-EP+ buffer and were injected to flow cell 2 (or 4) at 30 µL/min until the baseline response increased by 104 or 127 RU. The instrument was then primed using running buffer (HBS-EP+). NGF was dissolved in HBS-EP+ buffer to produce a 185 nM stock solution, which was serially diluted to produce a concentration series down to 11 nM. For a given affinity measurement, these series of peptide solutions were successively injected into the flow cells for 240 seconds of contact time and 800 seconds of dissociation time using a flow rate of 50 µL/min at 25° C. Flow cells were regenerated by 2.5 M MgCl2 at 30 µL/min for 30 seconds after injection of each protein solutions.

Example 2—Design of Glycopeptides

Figure 29:
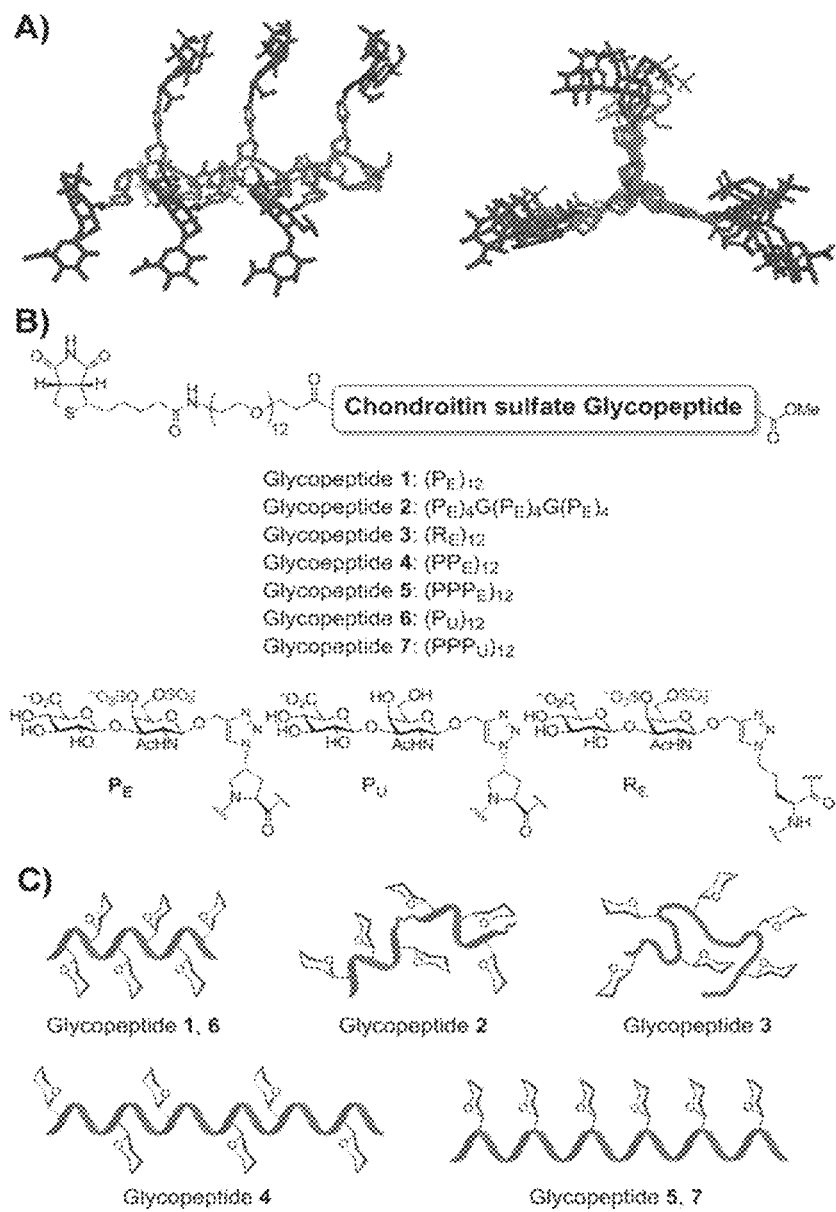
FIG. 29 shows (A) a model of an oligoproline PPII helix with CS-E disaccharides, (B) structures of modified polyproline glycopeptides 1 to 7 containing CS disaccharides, and (C) configurations of carbohydrate display of glycopeptides 1 to 7.

CS disaccharide monomers were incorporated into the PPII helix by click reaction of azido groups with alkynes bearing CS disaccharide moieties[3c]. Furthermore, a minimum spacer length between proline and sugar units allowed us the maximal positional control of carbohydrate units. Finally, biotin-conjugated $PEG_{12}$ were introduced at the end of peptide chain to facilitate the surface attachment (FIGS. 29A and 29B).

Seven glycopeptides were designed on the basis of above considerations. These were:
 i) two glycopeptides (1 and 2) containing CS-E disaccharide motifs at all faces of helix with/without backbone flexibility;
 ii) one glycopeptide (3) containing a completely flexible backbone;
 iii) one glycopeptide (4) containing equally distributed CS-E disaccharides along the helix backbone but more space as compared to 1;
 iv) one glycopeptide (5) displaying all CS-E disaccharides along one face of PPII helix; and
 v) two control glycopeptides containing unsulfated CS disaccharide moieties (6 and 7).

All CS-E glycopeptides differ only subtly in their orientation of functional motifs but have the same number of CS-E disaccharides. A comparison of the relative protein binding activity of 1 and 4 would allow for the evaluation of the importance of the distance between pendant groups. Inclusion of glycine residues on polyproline as in 2 was envisioned to introduce chain flexibility. Finally, glycopeptide 5 affords insight into not only the role of saccharide density but also the arrangement of active motifs (FIGS. 29B and 29C).

Example 3—Preparation of CS Glycopeptides 1-7

Figure 30:
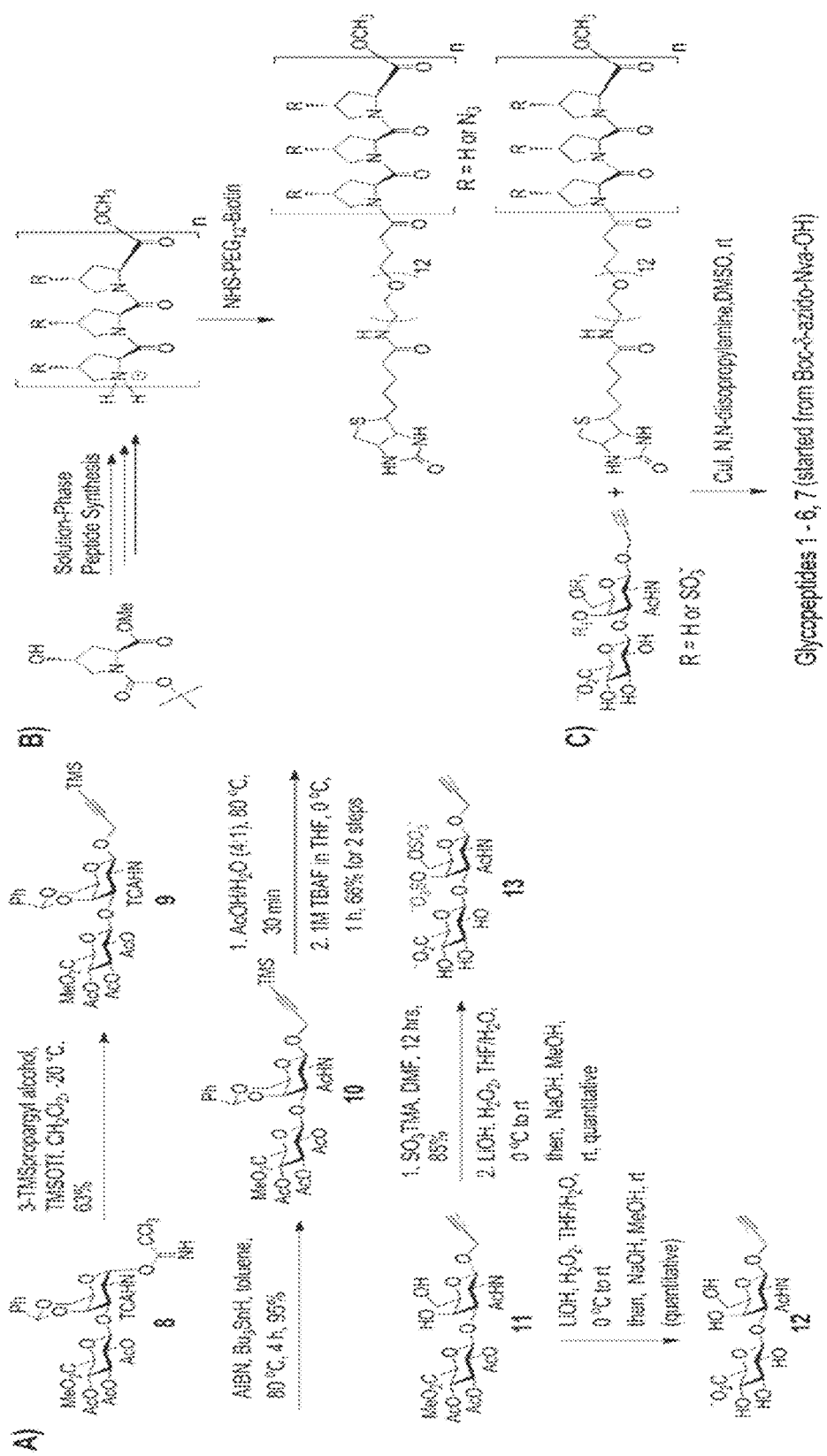
FIG. 30 shows (A) a schematic of the synthesis of alkyne-functionalized CS disaccharides, (B) the synthesis of biotinylated azido polyprolines, and (C) the click reaction for the synthesis of glycopeptides 1 to 7.

Studies began with the synthesis of biologically active CS-E and unsulfated CS disaccharide units containing alkyne functionality (FIG. 30). Briefly, the trichloroacetimidate 8[4] was converted to the fully protected disaccharide 9 mediated by trimethylsilyl triflate in good yield and stereoselectivity. Notably, terminal alkyne was protected to avoid free-radical hydrostannation.[5] With the key intermediate in hand, the study was continued with the deprotection-sulfation steps. Radical-mediated reduction of N-trichloroactyl group to N-acetyl congener with n-tributylstannane and AIBN yielded the acetamide 10. Hydrolysis of the benzylidene acetal followed by removal of the TMS group afforded the diol 11. Treatment of 11 with $SO_3$.trimethylamine complex delivered the sulfate motif efficiently. The desired CS-E disaccharide 13 was successfully elaborated by sequential treatment of LiOOH and NaOH. Deprotection of 11 under the similar conditions furnished the unsulfated disaccharide 12.

As the typical Fmoc chemistry on solid-phase resulted in very low coupling efficiency, all polyproline derivatives containing azides were prepared via standard solution-phase peptide synthesis. Boc-protected amino acid was coupled with amino acid methyl ester using O-(Benzotriazol-1-yl)-N,N,N',N'-tetramethyluronium tetra fluoroborate (TBTU) as the coupling reagent. Boc and methyl ester protective groups of resulting peptides were removed prior to the next coupling reactions by treatment of $CF_3CO_2H/CH_2Cl_2$ mixture and aqueous NaOH, respectively. Couplings and deprotections were repeated until the desired polyproline derivatives were obtained. All peptides were purified to homogeneity by flash column chromatography on silica or reverse phase HPLC and characterized by mass spectroscopy.

With CS disaccharides and polyproline derivatives in hand, the next focus was on synthesizing glycopolymers via conjugating the alkyne-functionalized CS disaccharides to the azido-functionalized polyprolines. The click reactions were conducted in DMSO at ambient temperature for 7 days in the presence of copper(I) idode, N,N-diisopropylethylamine (DIPEA), and tris[(1-benzyl-1H-1,2,3-triazol-4-yl) methyl]amine (TBTA) under argon atmosphere. The complete conversion of azido groups into 1,2,3-triazoles was monitored by FT-IR and $^1H$ NMR spectroscopy (see FIG. 19 and NMR spectra shown in FIGS. 20 to 26).[6] While the FT-IR spectra of azido-polyprolines revealed the presence of a strong vibrational band at 2100 $cm^{-1}$, which is characteristic of azide moieties, the disappearance of the azide band in the spectra of the glycopeptide derivatives clearly demonstrated the completion of the coupling reactions. Moreover, $^1H$ NMR spectra revealed the new signals from CS disaccharides. In addition, the characteristic peak at 8.2 ppm after the click reaction indicated the formation of 1,2,3-triazole linkage. Both FT-IR and $^1H$ NMR spectra, hence, fully demonstrated the efficiency of click reaction for the disaccharides. The resulting reaction mixtures were precipitated from THF/methanol mixture and then converted to their sodium salts. Purification by size-exclusion chromatography furnished the desired CS glycopeptides 1-7.

Example 4—Circular Dichroism Studies

With the glycopeptides successfully prepared, circular dichroism (CD) studies were performed to investigate the PPII helix stability of the glycopeptides. Although several reports have suggested that polyprolines can be efficiently functionalized while retaining PPII conformations,[3b,3c,3d] an attempt was made to validate whether the bulky and highly charged pendant groups could induce the conformational change of backbones, thereby making it difficult to position functional groups at desired sites. For these studies, the peptide solutions (400 µM) were incubated at 4° C. for 24 h to allow for complete folding and measured at room temperature. In order to examine the backbone conformation of glycopeptides, CD signals of corresponding CS disaccharides (see FIG. 27)[7] were subtracted from those of glycopeptides. The CD traces (displayed in FIG. 28) show that, while the CD spectrum of 3 exhibited a random coil conformation as expected, other glycopeptides adopt a polyproline type II helical profile with a maximum positive band at 224-228 nm and minimum negative band at 208-213 nm, as is typically observed for a PPII helix.[8] These data confirm that inclusion of CS disaccharides to polyproline does not affect the fold of the backbone, and the polyproline scaffold maintains the native structure even with anionic groups along the same face of the helix.

Example 5—ELISA

Figure 31:
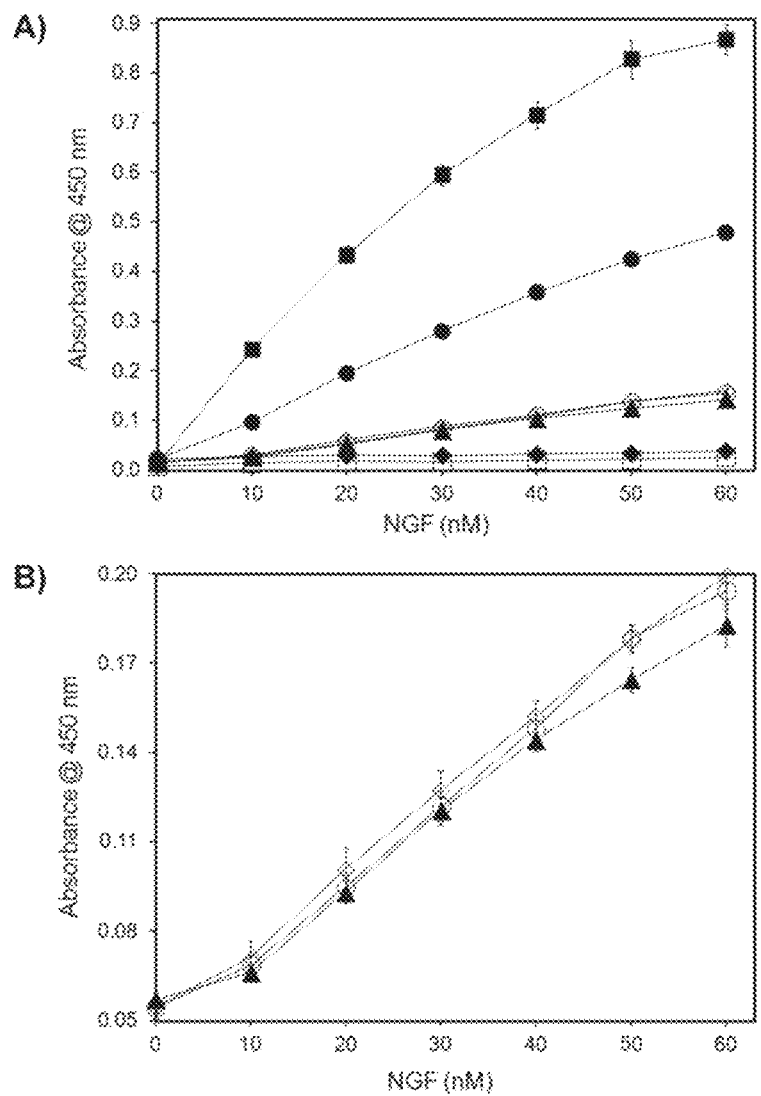
FIG. 31 shows (A) the comparison of the binding affinities of glycopeptides 1 to 7 to NGF at various concentrations, and (B) an expanded view of glycopeptides 1 to 3 from FIG. 31(A); ◇1, ▲2, ○3, ●4, ■5, □6, ◆7. All data presented as mean±SD of triplicates.

To evaluate the ability of the glycopeptides to interact with protein receptors, the binding affinity of each agent with nerve growth factor (NGF), which is known to bind CS-E sulfation motif selectively,[9] was examined by ELISA. For this study, glycopeptides at a constant concentration were immobilized on the streptavidin-coated 96-well plates followed by treating various concentrations of NGF into the solution as a mimic of GAG-extracellular protein interactions on the cell surface. The amount of glycopeptide-bound NGF was measured by HRP-conjugated polyclonal NGF antibody. Glycopeptides 1 and 6 served as initial compounds for this protein binding study. NGF turned out to bind to CS-E sulfated glycopeptide 1 in a concentration-dependent manner and displayed no significant binding to unsulfated glycopeptide 6 (FIG. 31A). Although 1 exhibited moderate binding affinity to NGF, these results are consistent with the previous reports in which CS-E sulfation motif provides a major binding epitope to NGF. To enhance the binding affinity, attempts were made to modify the agent 1. One expected consequence of polyproline scaffold is that rigidity of glycopeptide backbone would hamper the target protein binding as the flexibility of polymer chain is important for the interaction by accommodating the secondary structure of relevant proteins.[10] To address this problem, two compounds were prepared containing either partially flexible chain by incorporating glycine residues (2) or entirely flexible chain (3). No enhancement of binding affinity, however, was observed compared to 1, indicating that the chain flexibility is not the crucial factor in the model system (FIG. 31B).

Previous studies have shown that the binding elements density in multivalent ligands can affect the binding affinity towards the target protein.[6d,10,11] To investigate the influence of the binding epitope density, the glycopeptide 4 was synthesized. In this design, proline residues were added between CS-E conjugated prolines to introduce more space while retaining the same spatial arrangements of sugar epitopes as the initial agent 1. This modification resulted in significant increase in NGF binding affinity by approximately 2.6-fold in comparison to 1 (FIG. 31A). It is noteworthy that this phenomenon arises entirely from the distance between binding epitopes over any other factors by taking advantage of rigid polyproline property without perturbing a steric and electronic environment. Finally, all CS units were deployed at one face, while the other two faces contained proline residues, resulting in the agents 5 and 7 with a repeating PPPE or PPPU unit (FIGS. 29B and 29C). The compound 5 was the most effective binding ligand to NGF by 4.6-fold increase as compared to 1, while 7 did not exhibit any binding (FIG. 31A). Thus, the results clearly demonstrate that the spatial arrangement of the binding epitopes in multivalent ligands has considerable effects on the binding affinity towards target receptors.

Example 6—Surface Plasmon Resonance

Figure 32:
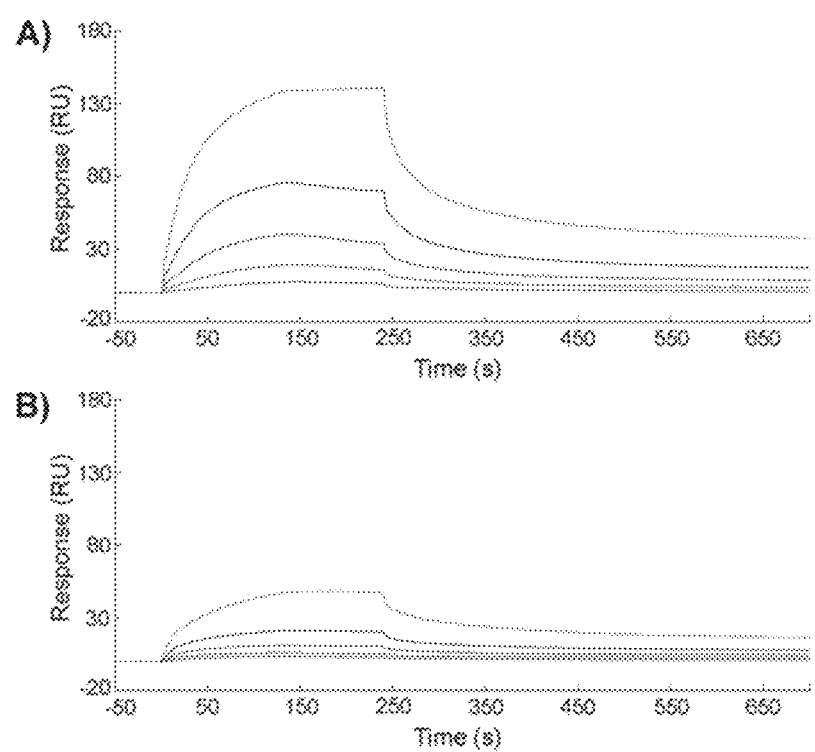
FIG. 32 shows the surface plasmon resonance of NGF binding at varying concentrations (185, 93, 46, 23, and 11 nM from top to bottom) to immobilized CS glycopeptides. The binding analysis was performed at 25° C., (A) with glycopeptide 5, and (B) with glycopeptide 1.
Figure 33:
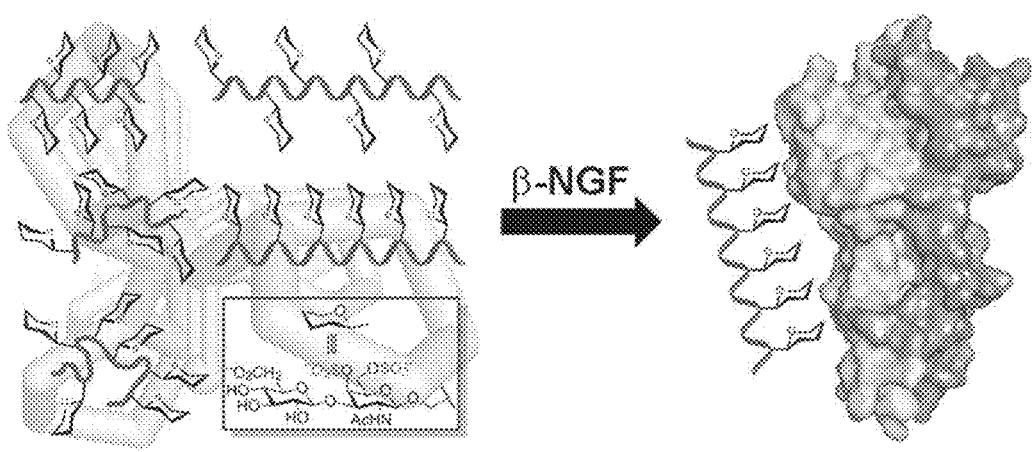
FIG. 33 shows one embodiment of the use of a glycopeptide as defined above as a glycomimetic in binding β-NGF.

Surface plasmon resonance (SPR) technology was further employed to facilitate quantitative, real-time kinetic analysis of glycopeptide-NGF interaction. Streptavidin was coated on a carboxydextran CM5 sensor chip, using EDC/NHS coupling chemistry, at a relatively low density (≈700 RU) to prevent nonspecific interactions with NGF. Biotinylated glycopeptides were then immobilized on streptavidin-coated surface at normalized levels by molecular weights,[12] 104 and 127 RU for 1 and 5, respectively. Kinetics were monitored at 25° C. by injecting various concentrations of NGF (11-185 nM) over the surface for 240 s at 50 µL·min$^{-1}$ and recording the dissociation for 800 s before the surface was regenerated with 2.5 M solution of $MgCl_2$. As shown in FIG. 32, both CS-E sulfated glycopeptides were efficiently recognized by NGF. In addition, the glycopeptide 5 gave higher overall responses than the glycopeptide 1, indicating that 5 recruits NGF more efficiently than 1. These results are consistent with those of ELISA described above. Further kinetic analysis was conducted using a two-state binding model for comprehensive understanding of this binding event. It is well known that many carbohydrate-protein binding processes are much more complex than a simple Langmuir 1:1 interaction and exhibit a two-state binding kinetics.[13] In this model, surface-bound glycopeptide binds to NGF to form an initial complex and then undergoes conformational change to form a more stable complex.[14] The complete kinetic parameters including equilibrium constants KD with standard errors in parentheses are given in Table 3 below. This kinetic analysis yielded an interesting result. A comparison of $K_D$ values revealed that the agent 5 ($K_D$=137 nM) binds to NGF more strongly than the agent 1 ($K_D$=2500 nM) by approximately 18-fold. Moreover, the kinetic result suggests that the higher binding affinity of 5 was mainly attributed to the relatively fast initial association rate ($k_{a1}$ (5)=4.65 (±0.16)×104 $M^{-1}$ $s^{-1}$) compared to 1 ($k_{a1}$ (1)=1.95 (±0.39)×103 $M^{-1}$ $s^{-1}$). This result suggests that a subtle change in binding epitope display can significantly impact the rate at which target receptor proteins are clustered. Previous investigations have focused on optimizing activity on the basis of binding epitope density by changing the ratio of biologically active to inactive monomers.[10,11] Here, it is discovered that the simple conformational change of binding motifs is sufficient to manipulate receptor-ligand interactions.

TABLE 3

Calculated (two-state kinetic model) equilibrium binding constants of glycopeptide 1 and 5 to NGF.

|  | Glycopeptide 1 | Glycopeptide 5 |
|---|---|---|
| $k_{a1}$ ($M^{-1}s^{-1}$) | 1.95 (±0.39) × $10^3$ | 4.65 (±0.16) × $10^4$ |
| $k_{d1}$ ($s^{-1}$) | 3.22 (±0.07) × $10^{-2}$ | 2.74 (±0.04) × $10^{-2}$ |
| $k_{a2}$ ($M^{-1}s^{-1}$) | 3.62 (±0.04) × $10^{-3}$ | 1.97 (±0.02) × $10^{-3}$ |
| $k_{d2}$ ($s^{-1}$) | 6.43 (±0.13) × $10^{-4}$ | 6.00 (±0.17) × $10^{-4}$ |
| $K_D$ (M) | 2.50 × $10^{-6}$ | 1.37 × $10^{-7}$ |

Example 7—Glycopeptides for Use as Biological Mimetics

Neurotrophins are a family of proteins that play important roles in the central nervous system to ensure proper brain functions. In particular, nerve growth factor (NGF) is critical for the survival and differentiation of certain neurons. It is distributed in many parts of the brain such as substantia nigra, basal forebrain and brain stem. Deprivation of NGF in these areas can lead to neuronal death and eventually neurodegenerative disorders including Parkinson's disease and Alzheimer's disease. To maintain neuronal survival and neurite outgrowth, NGF binds to a transmembrane receptor TrkA, induces receptor phosphorylation and activates the downstream signaling pathway. Interaction between NGF and TrkA requires glycosaminoglycan (GAG) chondroitin sulfate, which facilitates the formation of a stable complex. Glycopeptides that mimic the natural GAGs with binding specificity and affinity as well as biological activities in various systems were designed and synthesized.

Experimental Procedures

Cell Culture

Rat pheochromocytoma (PC12) cells were maintained in T75 tissue culture flask in complete RPMI 1640 growth medium containing 10% heat-inactivated horse serum (HI-HS), 5% fetal bovine serum (FBS) and 1% penicillin/streptomycin. Stock cultures from liquid nitrogen were grown at 37° C. with 5% $CO_2$ in a humidified chamber for 72 hr before experiments.

Preparation of Glass Coverslips 13 mm glass coverslips were submerged in 65% nitric acid for at least three days. The coverslips were washed with distilled water, 70% ethanol and 100% ethanol 3× each for 30 minutes with gentle rocking. The coverslips were dried in the cell culture hood overnight with UV sterilization. For coating, 60 μl of laminin solution (25 μg/ml in sterile PBS) was added to each coverslip, followed by 2 hr incubation at 37° C. The coverslips were rinsed 3× with PBS and dried in the hood before use.

Neurite Outgrowth Assay

PC12 cells were seeded on laminin-coated coverslips at a density of 100 cells/mm$^2$ in RPMI 1640 differentiation medium containing 1% HI-HS. Cells were allowed to attach to the surface for 1 hr at 37° C. The coverslips were transferred to 24-well plates and the cells were incubated with fresh differentiation medium for 1 hr. Glycopeptides were incubated with NGF in differentiation medium for 1 hr at room temperature before adding to the cells together. At the end of culture period, the cells were fixed with 4% formaldehyde solution for 15 minutes at room temperature and rinsed 2× with PBS. All experiments were repeated three times and done in duplicate each time. For each treatment, 400-500 randomly selected single cells were counted. The percentage of neurite-bearing cells was determined by counting the number of cells with neurite length at least one cell body long.

Western Blotting

PC12 cells were seeded on laminin-coated coverslips at a density of 300 cells/mm$^2$ and one coverslip was used for each treatment (~40,000 cells in total). Cells were starved in differentiation medium for 12-18 hr before use. For glycopeptide treatment, cells were incubated with fresh differentiation medium containing 10 μM glycopeptide for 1 hr at 37° C. To induce TrkA phosphorylation, cells were treated with NGF at a final concentration of 4 ng/ml for 5 minutes at 37° C. Cells were washed with ice cold PBS and lysed using RIPA lysis buffer containing protease and phosphatase inhibitors. The protein samples were separated on 4-12% SDS-PAGE gel and transferred to nitrocellulose membrane. Membranes were blocked for 1 h at room temperature and probed with anti-TrkA Ab (1:1500) and anti-pTrkA Ab (1:1500) overnight at 4° C., followed by 2 hr incubation with horseradish peroxidase-conjugated secondary antibodies. Enhanced chemiluminescence system was used for detection. The bands were quantified using the ImageJ program and the ratio of phosphor-TrkA to total TrkA was calculated and expressed as arbitrary units (a.u.).

Results

PPPE12 Promotes NGF-Mediated Neurite Outgrowth in PC12 Cells

Figure 34:
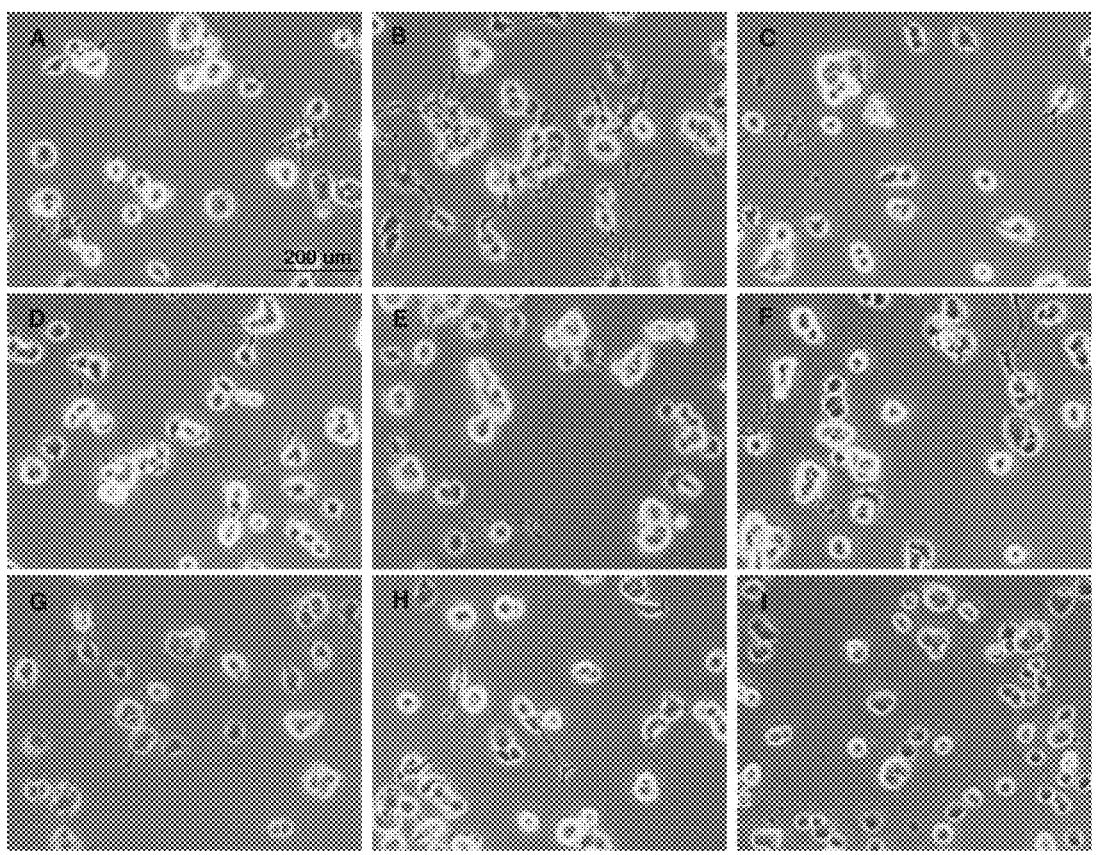
FIG. 34 demonstrates the effects of the glycopeptides 1 to 7 on NGF-induced neurite outgrowth in PC12 cells. Cells were grown in the presence or absence of NGF (4 ng/ml) and different glycopeptides (10 μM) for 72 hr. (A) Control/NGF only; (B) glycopeptide 5; (C) glycopeptide 7; (D) CS-E polysaccharide; (E) glycopeptide 1; (F) glycopeptide 4; (G) Semi-Flexible glycopeptide 2; (H) Random Coil glycopeptide 3; (I) glycopeptide 5 only.
Figure 35:
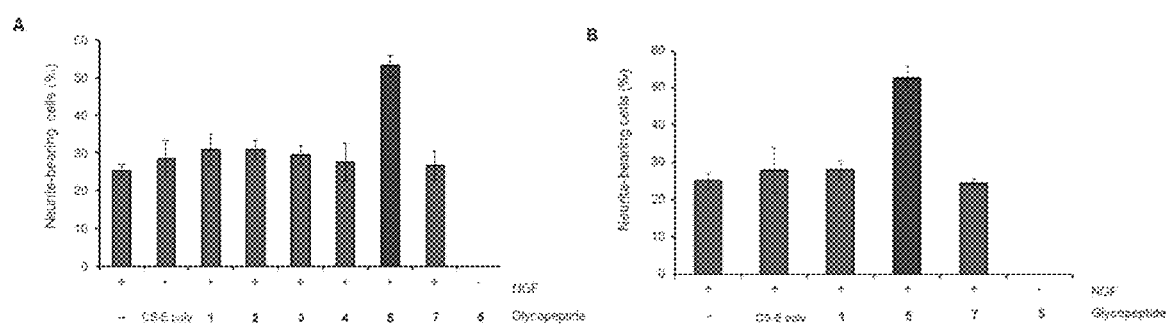
FIG. 35 demonstrates the quantification of neurite-bearing cells for two sets of experimental conditions. Left: 4 ng/ml NGF and 10 μM glycopeptide, grown for 3 days. Right: 2 ng/ml NGF and 6 μM glycopeptide, grown for 5 days and media with complete supplements were changed at day 3. Data are average ±SD values from three separate experiments for each condition.

When PC12 cells were exposed to NGF in serum-free medium, extension of neurites was observed. Treatment of single-facial glycopeptide 5 significantly promoted neurite outgrowth compared to the control whereas other designs such as the equally distributed glycopeptide 1 and unsulfated glycopeptide 7 displayed no effect (FIG. 34). In the absence of NGF, PC12 cells treated with glycopeptide 5 only remained round-shaped and undifferentiated, indicating that the glycopeptide functions through the NGF-mediated pathway. Percentage of neurite-bearing cells was also greatly increased with the glycopeptide 5 treated samples (FIG. 35).

TrkA Phosphorylation is Enhanced with PPPE12 Treatment

Figure 36:
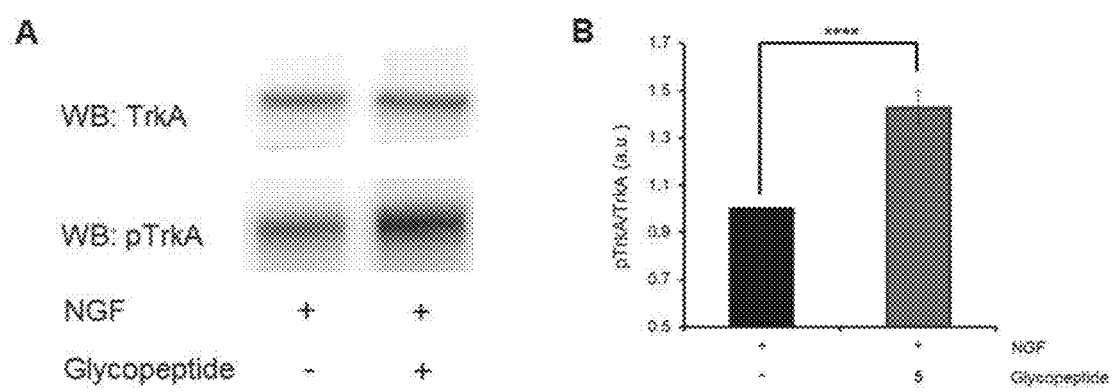
FIG. 36 shows that glycopeptide 5 enhances NGF-mediated TrkA activation in PC12 cells. The ratio for the NGF-treated control sample is normalized to 1. Data are average±SD values from five separate experiments for each condition (****$p<0.0001$).

The role of glycopeptide 5 in the NGF/TrkA pathway was examined by monitoring TrkA activation using Western blot. The addition of glycopeptide 5 increased NGF-induced TrkA phosphorylation by ~40% compared to the control sample (FIG. 36). This finding further supports the cell culture data that the single-facial glycopeptide can act as a neuronal promoter in NGF-induced PC12 differentiation process.

Glycopeptide 5 Facilitates the Formation of a Stable NGF/TrkA Complex

Figure 37:
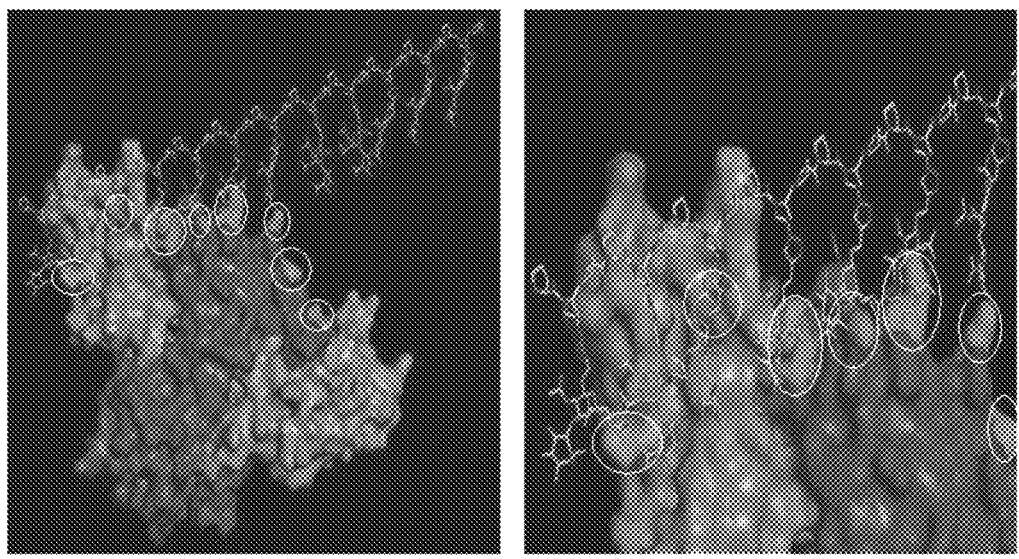
FIG. 37 shows the predicted glycopeptide 5 binding site with NGF/TrkA complex (basic residues are circled in white).

Protein modeling studies were conducted to investigate the binding between glycopeptide 5 and NGF/TrkA complex. According to the crystal structure of NGF/TrkA complex, there are 6 basic residues arranged linearly at 10~17 Å apart (FIG. 37). Glycopeptide 5 presents 12 disaccharide units with sulfate groups at 9-11 Å apart facing the same direction. This allows for a perfect geometric fit of sulfate groups to the basic residues, which maximizes the electrostatic interactions and stabilizes the NGF/TrkA complex.

Applications

In summary, a new class of CS glycopeptides has been developed, in which the orientation of CS motifs is precisely controlled by taking advantage of rigid polyproline scaffold. The ability to manipulate multivalent interactions is significant as individual design, in spite of high charge density, showed a distinct binding affinity to target protein. Specifically, NGF exhibited the highest binding affinity to glycopeptide 5 that has all CS-E motifs along one face. Furthermore, the better binding affinity of agent 4 and 5 than 1 clearly demonstrated the influence of binding epitope on multivalent interactions without perturbing a steric and electronic environment. While the majority of research to-date has focused on optimizing activity on the basis of binding epitopes, the present invention underscores the importance of their spatial and conformational display in designing multivalent ligands. The present findings are anticipated to provide a useful tool for developing target-specific therapeutic agents, biopolymers and markers, and manipulating their functions in vivo.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

REFERENCES

1. F. Bélot and J.-C. Jacquinet, Carbohydr. Res., 2000, 326, 88.
2. H. Lucas, J. E. M. Basten, T. G. van Dinther, D. G. Meuleman, S. F. van Aelst, and C. A. A. van Boeckel, Tetrahedron, 1990, 46, 8207.
3. a) Y. A. Fillon, J. P. Anderson, J. Chmielewski, J. Am. Chem. Soc. 2005, 127, 11798-11803; b) M. Kümin, L.-S. Sonntag, H. Wennemers, J. Am. Chem. Soc. 2007, 129, 466-467; c) L. Nagel, C. Budke, R. S. Erdmann, A. Dreyer, H. Wennemers, T. Koop, N. Sewald, Chem. Eur. J. 2012, 18, 12783-12793; d) Y. A. Nagel, M. Kuemin, H. Wennemers, Chimia (Aarau) 2011, 65, 264-267.
4. A. Vibert, C. Lopin-Bon, J.-C. Jacquinet, Chem. Eur. J. 2009, 15, 9561-9578.
5. E. A. Crane, T. P. Zabawa, R. L. Farmer, K. A. Scheidt, Angew. Chem. Int. Ed. 2011, 50, 9112-9115.
6. a) Q.-H. Zhou, J.-K. Zheng, Z. Shen, X.-H. Fan, X.-F. Chen, Q.-F. Zhou, Macromolecules 2010, 43, 5637-5646; b) Z. Ge, Y. Zhou, J. Xu, H. Liu, D. Chen, S. Liu, J. Am. Chem. Soc. 2009, 131, 1628-1629; c) A. Pathigoolla, R. G. Gonnade, K. M. Sureshan, Angew. Chem. Int. Ed. 2012, 51, 4362-4366; d) S.-J. Richards, M. W. Jones, M. Hunaban, D. M. Haddleton, M. I. Gibson, Angew. Chem. Int. Ed. 2012, 51, 7812-7816.
7. M. K. Cowman, E. A. Balazs, C. W. Bergman, K. Meyer, Biochemistry 1981, 20, 1379-1385.
8. N. Helbecque, M. H. Loucheux-Lefebvre, Int. J. Pept. Protein Res: 1982, 19, 94-101.
9. C. J. Rogers, P. M. Clark, S. E. Tully, R. Abrol, K. C. Garcia, W. A. Goddard III, L. C. Hsieh-Wilson, Proc. Natl. Acad. Sci. U.S.A. 2011, 108, 9747-9752.
10. a) C. W. Cairo, J. E. Gestwicki, M. Kanai, L. L. Kiessling, J. Am. Chem. Soc. 2002, 124, 1615-1619; b) J. E. Gestwicki, C. W. Cairo, L. E. Strong, K. A. Oetjen, L. L. Kiessling, J. Am. Chem. Soc. 2002, 124, 14922-14933.
11. a) B. D. Polizzotti, R. Maheshwari, J. Vinkenborg, K. L. Kiick, Macromolecules 2007, 40, 7103-7110; b) J. N. Kizhakkedathu, A. L. Creagh, R. A. Shenoi, N. A. A. Rossi, D. E. Brooks, T. Chan, J. Lam, S. R. Dandepally, C. A. Haynes, Biomacromolecules 2010, 11, 2567-2575; c) K. Godula, C. R. Bertozzi, J. Am. Chem. Soc. 2012, 134, 15732-15742.
12. J. I. Jay, B. E. Lai, D. G. Myszka, A. Mahalingam, K. Langheinrich, D. F. Katz, P. F. Kiser, Mol. Pharm. 2010, 7, 116-129.
13. Y. E. Tsvetkov, M. Burg-Roderfeld, G. Loers, A. Ardá, E. V. Sukhova, E. A. Khatuntseva, A. A. Grachev, A. O. Chizhov, H.-C. Siebert, M. Schachner, J. Jiménez-Barbero, N. E. Nifantiev, J. Am. Chem. Soc. 2012, 134, 426-435; b) H. Furuya, R. Ikeda, Microbiology 2009, 155, 2707-2713; c) M. Futamura, P. Dhanasekaran, T. Handa, M. C. Phillips, S. Lund-Katz, H. Saito, J. Biol. Chem. 2005, 280, 5414-5422,
14. a) R. Karlsson, A. Fält, J. Immunol. Methods 1997, 200, 121-133; b) C. A. Lipschultz, Y. Li, S. Smith-Gill, Methods 2000, 20, 310-318.

The invention claimed is:

1. A glycopeptide, comprising a polyproline backbone and one or more carbohydrate molecules, wherein the polyproline backbone has the following general formula (I):

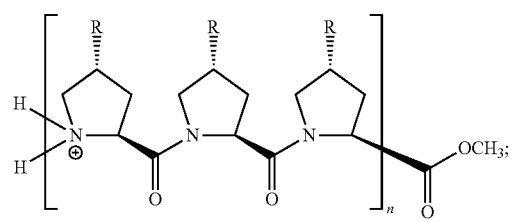

wherein R is independently H or $N_3$; wherein at least one R is $N_3$; n is 1 or more; the one or more carbohydrate molecules is selected from the group consisting of a chondroitin sulfate, a heparin, a heparan sulfate, a dermatan sulfate, a hyaluronan, and a keratan sulfate; and wherein the one or more carbohydrate molecules is alkyne-functionalized and attached to the polyproline backbone at R by forming a 1,2,3-triazole linkage when R is $N_3$.

2. The glycopeptide according to claim 1, wherein n is 8 or more.

3. The glycopeptide according claim 1, wherein the carbohydrate molecules are attached at pre-determined positions along the polyproline backbone at one or more of the following positions: at equal distances from each other along the polyproline backbone, and along the same face of the polyproline backbone.

4. The glycopeptides according to claim 1, wherein the chondroitin sulphate is selected from the group consisting of chondroitin sulfate A, chondroitin sulfate C, chondroitin sulfate D and chondroitin sulfate E.

5. The glycopeptide according to claim 1, further comprising one or more of the following: polyethylene glycol (PEG) at one end of the polyproline backbone, a biotin-conjugated PEG at one end of the polyproline backbone, and a lipid.

6. A glycopeptide comprising a polyproline backbone and one or more carbohydrate molecules having the following general formula (II):

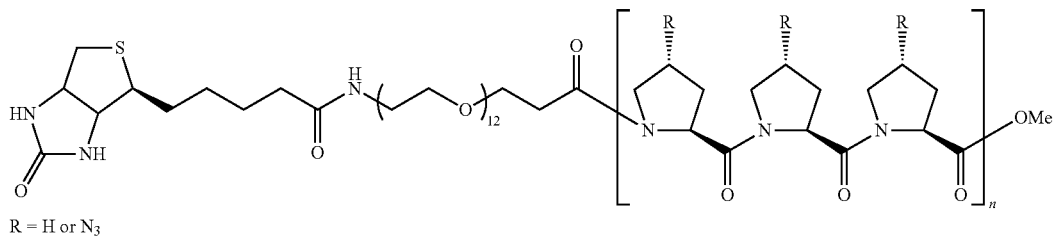

R = H or $N_3$ wherein R is independently H or $N_3$; wherein at least one R is $N_3$; n is 1 or more; the one or more carbohydrate molecules is selected from the group consisting of a chondroitin sulfate, a heparin, a heparan sulfate, a dermatan sulfate, a hyaluronan, and a keratan sulfate; and wherein the one or more carbohydrate molecules is alkyne-functionalized and attached to the polyproline backbone at R by forming a 1,2,3-triazole linkage when R is $N_3$.

7. The glycopeptide according to claim 6, wherein the polyproline backbone is a formula selected from the group consisting of: $(P_E)_4G(P_E)_4G(P_E)_4$, $(PP_E)_{12}$, $(PPP_E)_{12}$, $(PE)_{12}$, $(PP_EP_E)_6$ and $(PPP_U)_{12}$,
wherein P is proline; G is glycine;
$P_E$ is;

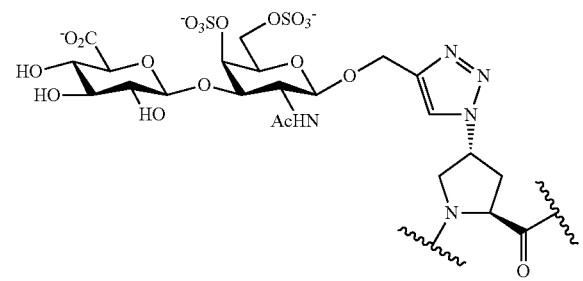

and
$P_U$ is

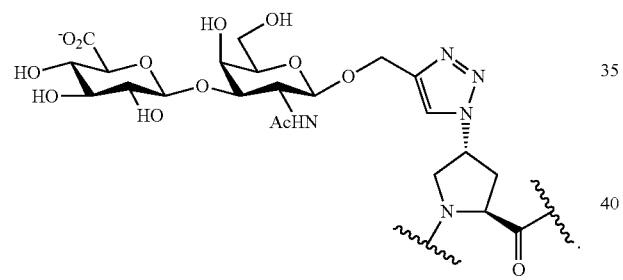

8. A method of synthesising a glycopeptide according to claim 1, comprising attaching one or more carbohydrate molecules to a polyproline backbone; wherein the one or more carbohydrate molecules is selected from the group consisting of a chondroitin sulfate, a heparin, a heparan sulfate, a dermatan sulfate, a hyaluronan, and a keratan sulfate.

9. The method according to claim 8, wherein the carbohydrate molecules are alkyne-functionalised chondroitin sulfate disaccharides.

10. The method according to claim 8, wherein the one or more carbohydrate molecules are attached to the polyproline backbone via a click reaction.

11. The method according to claim 10, comprising one or more of the following steps: conducting the click reaction in DMSO at ambient temperature for 7 days in the presence of copper (I) iodide, N,N-diisopropylethylamine (DIPEA) and tris[(1-benzyl-1H-1,2,3-triazol-4-yl)methyl]amine (TBTA) under argon atmosphere; precipitating the reaction mixture resulting from the click reaction from a THF/methanol mixture; converting the reaction mixture into their sodium salt form; and purifying the salt by size-exclusion chromatography.

12. The method according to claim 9, wherein the alkyne-functionalised chondroitin sulfate disaccharides are synthesised by:
(i) converting tricholoroacetimidate 8

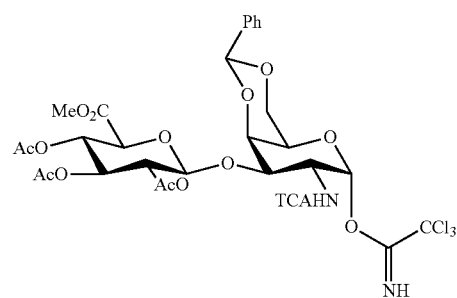

to the fully protected disaccharide 9

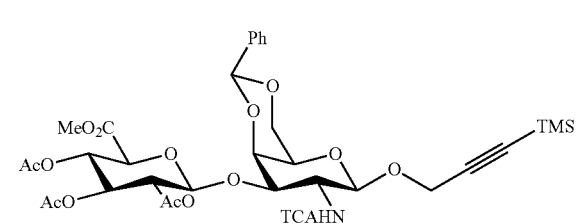

using trimethylsilyl triflate;
(ii) reducing N-trichloroactyl group to N-acetyl congener with n-tributylstannane and AIBN by radical-mediated reduction to yield the acetamide 10

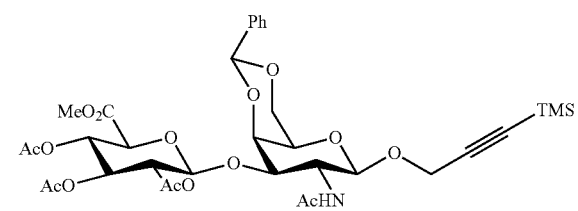

(iii) hydrolysing the benzylidene acetal followed by removing the TMS group to produce the diol 11

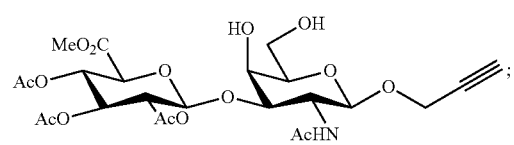

(iv) optionally treating the diol 11 with $SO_3$.trimethylamine complex; and
(v) treating the resultant mixture with LiOOH and NaOH.

13. The method according to claim 12, comprising synthesising the polyproline backbone via solution-phase peptide synthesis.

14. The method according to claim 13, wherein the solution-phase peptide synthesis comprises the steps of:

(i) coupling the Boc protected amino acid with amino acid methyl ester using O-(Benzotriazol-1-yl)-N,N,N',N'-tetramethyluronium tetrafluoroborate (TBTU) as the coupling reagent;

(ii) removing Boc and methyl ester protective groups of the resulting peptides prior to the next coupling reactions by treatment with a $CF_3CO_2H/CH_2Cl_2$ mixture and aqueous NaOH, respectively;

(iii) repeating steps (i) and (ii) until the desired polyproline derivates are obtained; and (iv) purifying the polyproline derivatives by flash column chromatography on silica or reverse phase HPLC.

15. A method of controlling the binding affinity of a glycopeptide to one or more binding molecules, comprising attaching one or more alkyne-functionalized carbohydrate molecules at pre-determined positions along an azido-functionalized polyproline backbone by forming a 1,2,3-triazole linkage; wherein the one or more carbohydrate molecules is selected from the group consisting of a chondroitin sulfate, a heparin, a heparan sulfate, a dermatan sulfate, a hyaluronan, and a keratan sulfate.

16. The method according to claim 15, wherein the polyproline backbone is one having the following general formula (I):

(I)

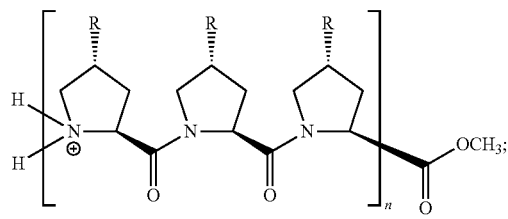

wherein R is independently H or $N_3$; wherein at least one R is $N_3$; n is 1 or more; and wherein the one or more carbohydrate molecules are attached to the polyproline backbone at R by forming a 1,2,3-triazole linkage when R is $N_3$.

17. The method according to claim 15, comprising attaching the carbohydrate molecules at pre-determined positions along the polyproline backbone at one or more of the following positions: at equal distances from each other along the polyproline backbone, and along the same face of the polyproline backbone.

18. The method according to claim 15, further comprising administering the glycopeptide to a patient in need of target-specific therapy, wherein the glycopeptide is a glycopeptide as defined in claim 1.

19. The method according to claim 18, wherein the glycopeptide binds to a target selected from the group consisting of E-selectin, L-selectin, P-selectin, nerve growth factor, growth factor, chemokine and cytokine.

20. The method according to claim 18, wherein the patient in need of a target-specific therapy is a patient suffering from a disease selected from a group consisting of cancer and neurodegenerative disease.

* * * * *